(12) United States Patent
Bocskei et al.

(10) Patent No.: US 8,153,647 B2
(45) Date of Patent: Apr. 10, 2012

(54) ARYL- AND HETEROARYL-ETHYL-ACYLGUANIDINE DERIVATIVES, THEIR PREPARATION AND THEIR APPLICATION IN THERAPEUTICS

(75) Inventors: Jozsef Zsolt Bocskei, Antony (FR); Gary McCort, Antony (FR); Hans Matter, Langenselbold (DE); Henning Steinhagen, Sulzbach (DE); Bérangère Thiers, Antony (FR)

(73) Assignee: Sanofi-Aventis, Paris (FR)

( * ) Notice: Subject to any disclaimer, the term of this patent is extended or adjusted under 35 U.S.C. 154(b) by 623 days.

(21) Appl. No.: 12/335,198

(22) Filed: Dec. 15, 2008

(65) Prior Publication Data
US 2009/0203696 A1   Aug. 13, 2009

Related U.S. Application Data

(63) Continuation of application No. PCT/IB2007/002591, filed on Jun. 13, 2007.

(30) Foreign Application Priority Data

Jun. 15, 2006   (EP) .................................... 06290979

(51) Int. Cl.
| | | |
|---|---|---|
| A01N 43/42 | (2006.01) |
| A01N 43/58 | (2006.01) |
| A01N 43/60 | (2006.01) |
| A61K 31/44 | (2006.01) |
| A61K 31/50 | (2006.01) |
| A61K 31/495 | (2006.01) |
| C07D 237/00 | (2006.01) |
| C07D 237/02 | (2006.01) |
| C07D 237/26 | (2006.01) |
| C07D 487/00 | (2006.01) |
| C07D 241/00 | (2006.01) |
| C07D 241/02 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 211/68 | (2006.01) |
| C07D 211/80 | (2006.01) |
| C07D 213/02 | (2006.01) |
| C07C 277/00 | (2006.01) |
| C07C 279/00 | (2006.01) |

(52) U.S. Cl. ........ 514/279; 514/248; 514/249; 544/224; 544/233; 544/336; 546/29; 546/194; 564/237

(58) Field of Classification Search .................. 514/279, 514/248, 249; 544/224, 233, 336; 546/29, 546/194; 564/237
See application file for complete search history.

(56) References Cited

U.S. PATENT DOCUMENTS
5,567,734 A   10/1996   Schwark et al.

FOREIGN PATENT DOCUMENTS
EP   0666252   10/2002

*Primary Examiner* — Sreeni Padmanabhan
*Assistant Examiner* — Kendra D Carter
(74) *Attorney, Agent, or Firm* — Scully, Scott, Murphy & Presser, P.C.

(57) ABSTRACT

Disclosed are compounds according to formula (I):

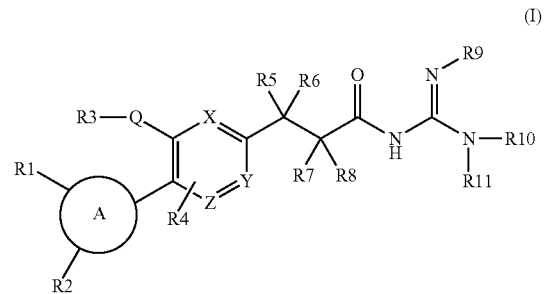

wherein A, Q, X, Y, Z, R1, R2, R3, R4, R5, R6, R7, R8, R9, R10 and R11 are as defined herein. The disclosure also relates to pharmaceutical compositions containing a compound of formula (I), to processes for preparing the compounds of formula (I), and to methods of using the compounds of formula (I).

34 Claims, No Drawings

ARYL- AND HETEROARYL-ETHYL-ACYLGUANIDINE DERIVATIVES, THEIR PREPARATION AND THEIR APPLICATION IN THERAPEUTICS

The instant invention relates to aryl- and heteroaryl-ethyl-acylguanidine derivatives, to their preparation method and to their application in therapeutics, in particular as renin inhibitors.

The renin-angiotensin system (RAS) is a key regulator of cardiovascular functions as well as for the balance of electrolytes and for maintaining body fluid volume, acting primarily by the effects of angiotensin II, an octapeptide hormone. The formation of angiotensin II involves two, main steps: renin (EC 3.4.99.19), a 340 amino acid aspartyl proteinase produced in the juxtaglomerular cells of the kidney, cleaves angiotensinogen to form the biologically inactive decapeptide angiotensin I. Renin release from the kidney and subsequent RAS activation in normotensive humans is stimulated by sodium or volume depletion, or by a reduction in blood pressure. Angiotensin I is next converted into angiotensin II by the zinc-dependent protease angiotensin-converting enzyme (ACE).

RAS activity is the principal determinant of several pathological states since angiotensin II, the major effector molecule of this system, increases blood pressure both directly by arterial vasoconstriction and indirectly by liberating the sodium-retaining hormone alderosterone from the adrenal glands, accompanied by an increase in extracellular fluid volume, as well as having growth-promoting effects on vascular, cardiac and renal tissues which contribute to end-organ damage.

The therapeutic response achieved with current RAS blockers, ACE inhibitors and angiotensin receptor blockers, although efficacious, is limited. This may indeed be possibly due to the rise in renin that these agents induce as a function of the resulting increase in angiotensin-peptides. Renin controls the initial and rate-limiting step in the RAS catalysing the cleavage of the Leu10-Val11 peptide bond of angiotensinogen, RAS resulting in angiotensin II formation. Thus inhibiting, renin completely inhibits the RAS. Along with its specificity for only one natural substrate, renin is an attractive therapeutic target.

A large number of peptidic and peptidomimetic inhibitors of human renin with various stable transition-state analogues of the scissile peptide bond have been developed since 1980. Despite their use as validation of renin as a therapeutic target, further drug development was often hampered by issues of bioavailability, duration of action or high cost of production. Thus there is a great need for new, non peptidic renin inhibitors.

Now, the Inventors have provided non peptidic renin inhibitors in the form of aryl- and heteroaryl-ethyl-acylguanidine derivatives.

The compounds according to the instant invention respond to the general formula (I):

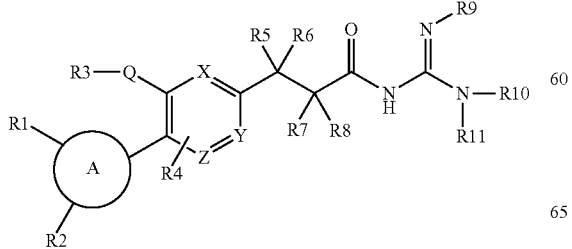

(I)

wherein:

A represents a ring chosen among a phenyl group, a heteroaryl group or a (C4-C8)cycloalkyl group, Q represents an oxygen atom or a —CH$_2$— link, X, Y and Z represent carbon or nitrogen atoms, being understood that either X, Y, Z represent carbon atoms, either one of X, Y and Z represents a nitrogen atom (resulting in a pyridinyl ring), either X and Z, or Y and Z, represent nitrogen atoms (resulting in pyrazinyl or pyridazinyl rings, respectively), R1 and R2, identical or different, are chosen among the following atoms and groups: hydrogen, halogen, hydroxyl, cyano, oxo, —CF$_3$, (C1-C6)alkyl, Alk, (C1-C6)alkoxy, (C1-C6)alkyl-O—(C1-C6)alkyl, —O—(C1-C6)alkyl-O—(C1-C6)alkyl, (C3-C8)cycloalkyl, —O—(C3-C8)cycloalkyl, —(CH$_2$)$_m$—SO$_2$—(C1-C6)alkyl with m is equal to 0, 1 or 2, benzyl, pyrazolyl, —CH$_2$-triazolyl optionally substituted by one to three (C1-C6)alkyl groups and -L-R12, wherein L represents a bond or a —CH$_2$— and/or —CO— and/or, —SO$_2$— linkage and R12 represents a (C3-C8)cycloalkyl or a group of formula (a), (b), (c), (c'), (d) or (e):

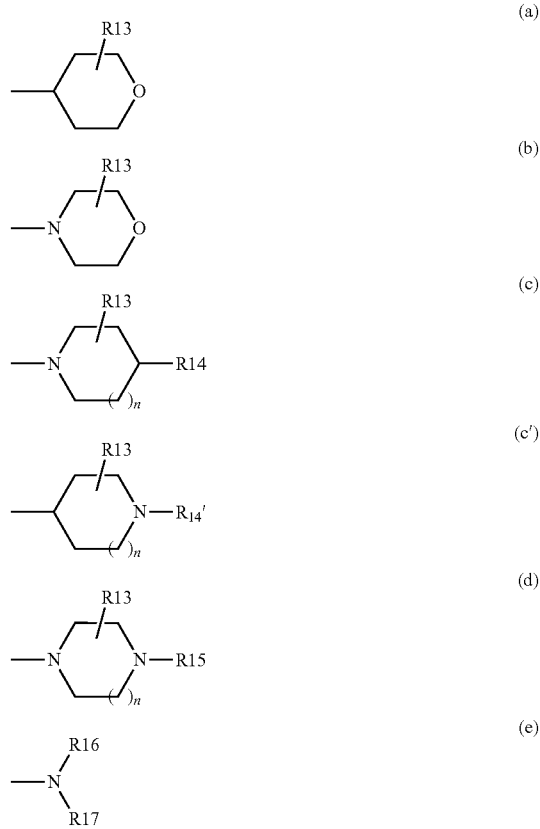

wherein:

n=0 or 1,

R13 represents one to three groups, identical or different, chosen among hydrogen and halogen atoms and hydroxyl, (C1-C4)alkyl, oxo and phenyl groups, R14 represents a hydrogen atom or is chosen among the —NR18R19, —NR18-COOR19, —NR18-Alk-R20 and —R21 groups, wherein R18, R19, R20, R21 and Alk are as defined below, or R13 and R14 together form, with the same carbon atom to which they are attached, a (C3-C8)cycloalkyl group, which is therefore present in the spiro position on the ring of formula (c), R14' represents a —CO—(C1-C6)alkyl group, R15 is chosen among the —NR18R19, -Alk, —R20, -Alk-R20, -Alk-R21, —CO-Alk, —CO—R20, —CO—R21, -Alk-CO—NR18R19, (C3-C8)cycloalkyl and —CO—(C3-C8)cycloalkyl groups, wherein R18, R19, R20, R21 and Alk are as defined below, R16 represents a hydrogen atom or an Alk group, wherein Alk is as defined below, R17 represents an -Alk, -Alk-R20 or -Alk-R21 group, wherein Alk, R20 and R21 are as defined below, —CO—(C1-C6)alkyl, —CO—(C3-C8)cycloalkyl, —CO-heterocycloalkyl groups, R18 and R19, identical or different, represent a hydrogen atom or a (C1-C6)alkyl group, R20 represents a phenyl or heteroaryl group (such as a pyridinyl, pyrazolyl, pyrimidinyl or benzimidazolyl group), which is optionally substituted with one or more halogen atoms or (C1-C6)alkyl, hydroxyl or (C1-C4) alkoxy groups, R21 represents a heterocycloalkyl group optionally substituted with one or more halogen atoms or (C1-C6)alkyl, hydroxyl or (C1-C4)alkoxy groups, and Alk represents a (C1-C6)alkyl group which is linear or branched and which is optionally substituted with one to three groups, identical or different, chosen among the halogen atoms and the hydroxyl, phenyl, (C1-C4)alkoxy and —NR18R19 groups, wherein R18 and R19 are as defined above, R3 represents a linear (C1-C10)alkyl group which is optionally substituted by one to three groups, identical or different, chosen among the halogen atoms and the (C1-C4)alkoxy groups, R4 represents a hydrogen or halogen atom or a hydroxyl, cyano, (C1-C6)alkyl or (C1-C6)alkoxy group, R5 and R6 represent, independently one from the other, a hydrogen or halogen atom or a (C1-C5)alkyl group, or R5 and R6 together form, with the carbon atom to which they are attached, a (C3-C6)cycloalkyl group, R7 and R8 represent, independently one from the other, a hydrogen atom or a (C1-C5)alkyl group, or R7 and R8 together form, with the carbon atom to which they are attached, a (C3-C6)cycloalkyl group, R9 and R10 represent, independently one from the other, a hydrogen atom or a hydroxyl, —CO—(C1-C6)alkyl or —COO—(C1-C6)alkyl group, or R9 and R10 together form a linear (C2-C3)alkylene chain, thereby forming a 5 or 6-membered ring with the nitrogen atoms to which they are attached, said alkylene chain being optionally substituted by one to three groups chosen among: (C1-C4)alkyl, (C3-C6)cycloalkyl groups in the spiro position, oxo, hydroxyl and amino groups, R11 represents a hydrogen atom or a (C1-C8)alkyl or (C3-C6)cycloalkyl group, which is optionally substituted by one to three groups chosen among: halogen atoms, hydroxyl, cyano, (C1-C6)alkoxy, —NR18R19, —COOR18, —CO—NR18R19 or pyridinyl groups, wherein R18 and R19 are as defined above.

The compounds of formula (I) can comprise one or more asymmetric carbon atoms. They can therefore exist in the form of isomers, especially optical antipods such as enantiomers or diastereoisomers. These isomers, enantiomers and diastereoisomers, as well as their mixtures, including racemic mixtures, form part of the invention.

The compounds of formula (I) can be provided in the form of a free base or in the form of addition salts with acids or with bases, which also form part of the invention.

These salts are advantageously prepared with pharmaceutically acceptable acids or bases, but salts with other acids or bases, useful for example for the purification or for the isolation of the compounds of formula (I), also form part of the invention.

The compounds of formula (I) can also be provided in the form of hydrates or of solvates, i.e. in the form of associations or combinations with one or more water or solvent molecules. Such hydrates and solvates also form part of the invention.

According to the present invention, and unless otherwise mentioned in the text, the terms below have the following meanings:

halogen atom: a fluorine, chlorine, bromine or iodine atom;

alkyl group: a saturated, linear, branched or partially cyclized aliphatic group. For example, (C1-C6)alkyl defines an alkyl group having from 1 to 6 carbon atoms. The following examples may be cited: methyl, ethyl, propyl, isopropyl, butyl, isobutyl, tertbutyl, neopentyl, pentyl, ethylcyclopropyl, etc;

cycloalkyl group: a cyclic alkyl group. For example, (C3-C8)cycloalkyl defines a cycloalkyl group having from 3 to 8 carbon atoms The following examples may be cited: cyclopropyl, cyclobutyl, cyclopentyl, cyclohexyl, etc;

heterocycloalkyl group: a saturated 5 or 6-membered ring comprising one or two heteroatoms chosen among the oxygen, nitrogen and sulphur atoms. The following examples may be cited: morpholinyl, piperidinyl, pyrrolidinyl, tetrahydrofuranyl, etc;

alkoxy group: an —O-alkyl group, wherein the alkyl group is as defined above;

alkylene chain: an alkyl group as defined above which is divalent. For example, a (C2-C3)alkylene corresponds to a —CH$_2$—CH$_2$— or —CH$_2$—CH$_2$—CH$_2$— divalent chain;

heteroaryl group: an aromatic, cyclic group comprising between 5 and 11 ring atoms chosen among carbon, nitrogen, oxygen and sulphur atoms. Heteroaryl groups may be monocyclic or bicyclic, in which case at least one of the two cyclic moieties is aromatic. Examples of monocyclic heteroaromatic groups may be the pyridinyl, pyrimidinyl, pyridazinyl, pyrazinyl, thiophenyl, thiazolyl, isothiazolyl, thiadiazolyl, oxazoyl, isoxazolyl, oxadiazolyl, pyrazolyl, triazolyl or imidazolyl groups, as well as their isomers. Examples of bicyclic heteroaromatic groups may be the benzothiophenyl, quinazolinyl, quinolinyl, benzothiazolyl, indazolyl, indolyl, benzimidazolyl, benzofuranyl, hydrobenzofuranyl, benzodioxolyl, benzoxadiazolyl, benzodioxanyl, tetrahydroisoquinoline 3,4-dihydro-1,5-benzodioxepinyl and 2,3-dihydro-1,4-benzodioxepinyl groups, as well as their isomers.

Among the compounds of formula (I) according to the present invention, the following compounds may be cited wherein A represents a ring chosen among a phenyl group or a heteroaryl group.

Among the compounds of formula (I) according to the present invention, the following compounds may be cited wherein:

A represents a phenyl, pyridinyl, pyridazinyl, pyrimidinyl, pyrazolyl, hydrobenzofuranyl, 3,4-dihydro-1,5-benzodioxepinyl, 2,3-dihydro-1,4-benzodioxepinyl, benzodioxanyl, benzodioxolyl, benzothiophenyl, indazolyl, thiophenyl or thiazolyl, benzoxadiazolyl, tetrahydroisoquinoline, benzimidazolyl group.

and/or

Q represents an oxygen atom or a —CH₂— link, and/or

X, Y and Z represent carbon atoms, and/or

R1 and R2, identical or different, represent a hydrogen or halogen atom or a hydroxyl, —CF$_3$, (C1-C6)alkyl, Alk, (C1-C6)alcoxy, (C1-C6)alkyl-O—(C1-C6)alkyl, —(CH$_2$)$_m$—SO$_2$—(C1-C6)alkyl with m is equal to 0, 1 or 2, benzyl, pyrazolyl or —CH$_2$-triazolyl group optionally substituted by one to three (C1-C6)alkyl groups, or a group of formula -L-R12, wherein L represents a bond or a —CH$_2$— and/or —CO— and/or —SO$_2$— linkage and R12 represents R12 represents a (C3-C8)cycloalkyl group or a group of formula (a), (b), (c), (c'), (d) or (e):

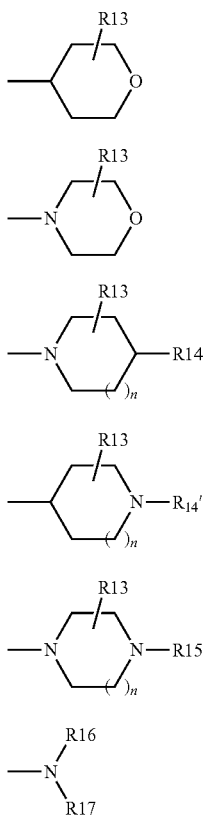

wherein:

n=0 or 1,

R13 represents one to three groups, identical or different, chosen among hydrogen and halogen atoms and (C1-C4)alkyl, oxo and phenyl groups, R14 represents a hydrogen atom or is chosen among the —NR18R19, —NR18-COOR19, —NR18-Alk-R20 and —R21 groups, wherein R18, R19, R20, R21 and Alk are as defined below, or R13 and R14 together form, with the same carbon atom to which they are attached, a (C3-C8)cycloalkyl group, which is therefore present in the spiro position on the ring of formula (c), R14' represents a —CO—(C1-C6)alkyl group, R15 is chosen among the -Alk, —R20, -Alk-R20, -Alk-R21, —CO-Alk, —CO—R20, —CO—R21, -Alk-CO—NR18R19, (C3-C8)cycloalkyl and —CO—(C3-C8)cycloalkyl groups, wherein R18, R19, R20, R21 and Alk are as defined below, R16 represents a hydrogen atom or an Alk group, wherein Alk is as defined below, R17 represents an -Alk, -Alk-R20 or -Alk-R21 group, wherein Alk, R20 and R21 are as defined below, —CO—(C1-C6)alkyl, —CO—(C3-C8)cycloalkyl, —CO-heterocycle groups R18 and R19, identical or different, represent a hydrogen atom or a (C1-C6)alkyl group, R20 represents a phenyl or heteroaryl group (such as a pyridinyl, pyrazolyl, pyrimidinyl or benzimidazolyl group), which is optionally substituted with one or more halogen atoms or (C1-C6)alkyl, hydroxyl or (C1-C4) alkoxy groups, R21 represents a heterocycloalkyl group optionally substituted with one or more halogen atoms or (C1-C6)alkyl, hydroxyl or (C1-C4)alkoxy groups, and Alk represents a (C1-C6)alkyl group which is linear or branched and which is optionally substituted with one to three groups, identical or different, chosen among the halogen atoms and the hydroxyl, phenyl, (C1-C4)alkoxy and —NR18R19 groups, wherein R18 and R19 are as defined above, and/or R3 represents a linear (C2-C8)alkyl group which is optionally substituted by one or two groups, identical or different, chosen among the halogen atoms and the (C1-C4)alkoxy groups, and/or R4 represents a hydrogen or halogen atom or a hydroxyl, cyano, (C1-C6)alkyl or (C1-C6)alkoxy group, and/or R5 and R6 represent, independently one from the other, a hydrogen or halogen atom or a (C1-C5)alkyl group, and/or R7 and R8 represent, independently one from the other, a hydrogen atom or a (C1-C5)alkyl group, or R7 and R8 together form, with the carbon atom to which they are attached, a (C3-C6)cycloalkyl group, and/or R9 and R10 represent hydrogen atoms or, when R11=H, R9 and R10 together form a linear (C2-C3)alkylene chain being optionally substituted by one to three groups chosen among: (C1-C4)alkyl, (C3-C6)cycloalkyl groups in the spiro position, oxo, hydroxyl and amino groups, and/or R11 represents a hydrogen atom or a (C1-C8)alkyl or (C3-C6)cycloalkyl group, which is optionally substituted by one to three groups chosen among: halogen atoms, hydroxyl, cyano, (C1-C6)alkoxy, —NR18R19, —COOR18, —CO—NR18R19 or pyridinyl groups, wherein R18 and R19 are as defined above.

Among these compounds of formula (I), mention may be made of those wherein R1 represents a hydrogen or halogen atom or a hydroxyl, —CF$_3$, (C1-C6)alkyl, (C1-C6)alkoxy, (C1-C6)alkyl-O—(C1-C6)alkyl, —SO$_2$—(C1-C6)alkyl group or Alk group as defined above.

Mention may also be made of the compounds wherein R1 represents a hydrogen or halogen atom or a —CF$_3$, (C1-C6) alkyl, (C1-C6) alcoxy group or Alk group as defined above.

Mention may also be made of the compounds wherein R1 represents a group of formula -L-R12, wherein L represents a bond or a —CH$_2$—, —CO— or —SO$_2$— linkage and R12 represents a group of formula (b):

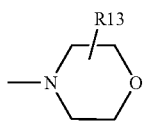

wherein R13 represents one to three groups, identical or different, chosen among hydrogen and halogen atoms and (C1-C4)alkyl and oxo groups.

Mention may also be made of the compounds wherein R1 represents a group of formula -L-R12, wherein L represents a —CO— or —SO₂— linkage and R12 represents a group of formula (b):

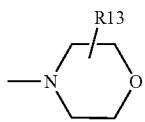

wherein R13 represents one to three groups, identical or different, chosen among hydrogen and halogen atoms and (C1-C4)alkyl and oxo groups.

Mention may also be made of the compounds wherein R1 represents a group of formula -L-R12, wherein L represents a bond or a —CH₂—, —CO— or —SO₂— linkage and R12 represents a group of formula (b):

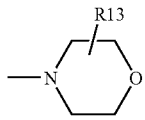

wherein R13 represents hydrogen.

Mention may also be made of the compounds wherein R1 represents a group of formula -L-R12, wherein L represents a bond or a —CH₂— and/or —CO— and/or —SO₂— linkage and R12 represents a group of formula (c):

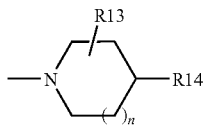

wherein:
n=0 or 1,
R13 represents one to three groups, identical or different, chosen among hydrogen and halogen atoms and (C1-C4)alkyl, oxo and phenyl groups,
R14 represents a hydrogen atom or a hydroxyl group or is chosen among the —NR18R19, —NR18-COOR19, —NR18-Alk-R20 and —R21 groups, wherein R18, R19, R20, R21 and Alk are as defined below,
R18 and R19, identical or different, represent a hydrogen atom or a (C1-C6)alkyl group,
R20 represents a phenyl group which is optionally substituted with one or more halogen atoms or (C1-C6)alkyl, hydroxyl or (C1-C4)alkoxy groups,
R21 represents a heterocycloalkyl group chosen among the morpholinyl, piperidinyl and pyrrolidinyl groups, which is optionally substituted with one or more halogen atoms or (C1-C6)alkyl, hydroxyl or (C1-C4)alkoxy groups, and
Alk represents a (C1-C6)alkyl group which is linear or branched and which is optionally substituted with one to three groups, identical or different, chosen among the halogen atoms and the hydroxyl, (C1-C4)alkoxy and —NR18R19 groups, wherein R18 and R19 are as defined above.

Mention may also be made of the compounds wherein R1 represents a group of formula -L-R12, wherein L represents a —CH₂— or —CO— linkage and R12 represents a group of formula (c):

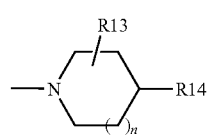

wherein:
n=0 or 1,
R13 represents one to three groups, identical or different, chosen among hydrogen and halogen atoms and (C1-C4)alkyl, oxo and phenyl groups,
R14 represents a hydrogen atom or is chosen among the —NR18R19, —NR18-COOR19, —NR18-Alk-R20 and —R21 groups, wherein R18, R19, R20, R21 and Alk are as defined below,
R18 and R19, identical or different, represent a hydrogen atom or a (C1-C6)alkyl group,
R20 represents a phenyl group which is optionally substituted with one or more halogen atoms or (C1-C6)alkyl, hydroxyl or (C1-C4)alkoxy groups,
R21 represents a heterocycloalkyl group chosen among the morpholinyl, piperidinyl and pyrrolidinyl groups, which is optionally substituted with one or more halogen atoms or (C1-C6)alkyl, hydroxyl or (C1-C4)alkoxy groups, and
Alk represents a (C1-C6)alkyl group which is linear or branched and which is optionally substituted with one to three groups, identical or different, chosen among the halogen atoms and the hydroxyl, (C1-C4)alkoxy and —NR18R19 groups, wherein R18 and R19 are as defined above.

Mention may also be made of the compounds wherein R1 represents a group of formula -L-R12, wherein L represents a bond or a —CH₂— and/or —CO— and/or —SO₂—linkage and R12 represents a group of formula (c):

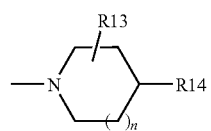

wherein:
n=0 or 1,
R13 represents one to three groups, identical or different, chosen among hydrogen and hydroxyl and (C1-C4) alkyl, oxo groups, R14 represents a hydrogen atom or is chosen among the —NR18R19, —NR18-COOR19, —NR18-Alk-R20 and —R21 groups, wherein R18, R19, R20, R21 and Alk are as defined below, R18 and R19, identical or different, represent a hydrogen atom or a (C1-C6)alkyl group, R20 represents a phenyl group, R21 represents a heterocycloalkyl group chosen among the morpholinyl, piperidinyl and pyrrolidinyl groups, which is optionally substituted with one or more (C1-C6)alkyl groups, and Alk represents a (C1-C6)alkyl group which is linear or branched.

Mention may also be made of the compounds wherein R1 represents a group of formula -L-R12, wherein L represents a bond or a —CH$_2$— or —CO— or —SO$_2$— or —CH$_2$—SO$_2$— linkage and R12 represents a group of formula (c):

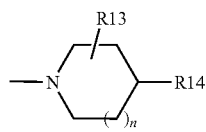

(c)

wherein:

n=0 or 1,

R13 represents one to three groups, identical or different, chosen among hydrogen and hydroxyl and (C1-C4)alkyl, oxo groups, R14 represents a hydrogen atom or is chosen among the —NR18R19, —NR18-COOR19, —NR18-Alk-R20 and —R21 groups, wherein. R18, R19, R20, R21 and Alk are as defined below, R18 and R19, identical or different, represent a hydrogen, atom or a (C1-C6)alkyl group, R20 represents a phenyl group, R21 represents a heterocycloalkyl group chosen among the morpholinyl, piperidinyl and pyrrolidinyl groups, which is optionally substituted with one or more (C1-C6)alkyl groups, and Alk represents a (C1-C6)alkyl group which is linear or branched.

Mention may also be made of the compounds wherein R1 represents a group of formula -L-R12, wherein L represents a —CH$_2$— or —CO— linkage and R12 represents a group of formula (d):

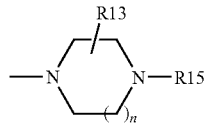

(d)

wherein:

n=0 or 1,

R13 represents one to three groups, identical or different, chosen among hydrogen and halogen atoms and (C1-C4)alkyl, oxo and phenyl groups, R15 represents an hydrogen atom or is chosen among the -Alk, —R20, -Alk-R20, -Alk-R20-CO-Alk, -Alk-R21, —CO—R20, —CO—R21, -Alk-CO—NR18R19, (C3-C6)cycloalkyle, —CO—(C3-C6)cycloalkyl and (C1-C6)alkyl-O—(C1-C6)alkyl groups, wherein R18, R19, R20, R21 and Alk are as defined below, R18 and R19, identical or different, represent a hydrogen atom or a (C1-C6)alkyl group, R20 represents a phenyl or heteroaryl group (such as a pyridinyl, pyrazolyl or pyrimidinyl group), which is optionally substituted with one or more halogen atoms or (C1-C6)alkyl, hydroxyl or (C1-C4)alkoxy groups, R21 represents a heterocycloalkyl group chosen among the morpholinyl, piperidinyl and tetrahydrofuranyl groups, which is optionally substituted with one or more halogen atoms or (C1-C6)alkyl, hydroxyl or (C1-C4)alkoxy groups, and Alk represents a (C1-C6)alkyl group which is linear or branched and which is optionally substituted with one to three groups, identical or different, chosen among the halogen atoms and the hydroxyl, (C1-C4)alkoxy and —NR18R19 groups, wherein R18 and R19 are as defined above.

Mention may also, be made of the compounds wherein R1 represents a group of formula -L-R12, wherein L represents a —CH$_2$— or, —CO— linkage and R12 represents a group of formula (d):

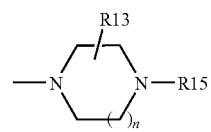

(d)

wherein:

n=0 or 1,

R13 represents one to three groups, identical or different, chosen among hydrogen and halogen atoms and (C1-C4)alkyl, oxo and phenyl groups, R15 is chosen among the -Alk, —R20, -Alk-R20, —CO-Alk, —CO—R20, —CO—R21, -Alk-CO—NR18R19, (C3-C6)cycloalkyl and —CO—(C3-C6)cycloalkyl groups, wherein R18, R19, R20, R21 and Alk are as defined below, R18 and R19, identical or different, represent a hydrogen atom or a (C1-C6)alkyl group, R20 represents a phenyl or heteroaryl group (such as a pyridinyl, pyrazolyl or pyrimidinyl group), which is optionally substituted with one or more halogen atoms or (C1-C6)alkyl, hydroxyl or (C1-C4)alkoxy groups, R21 represents a heterocycloalkyl group chosen among the morpholinyl piperidinyl and tetrahydrofuranyl groups, which is optionally substituted with one or more halogen-atoms or (C1-C6)alkyl, hydroxyl or (C1-C4)alkoxy groups, and Alk represents a (C1-C6)alkyl group which is linear or branched and which is optionally substituted with one to three groups, identical or different, chosen among the halogen atoms and the hydroxyl, (C1-C4)alkoxy and —NR18R19 groups, wherein R18 and R19 are as defined above.

Mention may also be made of the compounds wherein R1 represents a group of formula -L-R12, wherein L represents a, —CH$_2$— or —CO— linkage and R12 represents a group of formula (d):

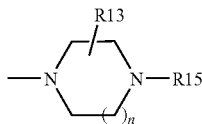
(d)

wherein:
n=0 or 1,
R13 represents one to three groups, identical or different, chosen among hydrogen and (C1-C4)alkyl, oxo and, phenyl groups,
R15 represents an hydrogen atom or is chosen among the -Alk, -Alk-R20, -Alk-R20-CO-Alk, -Alk-R21, —CO—R20, —CO—R21, -Alk-CO—NR18R19, (C3-C6)cycloalkyle, —CO—(C3-C6)cycloalkyl and (C1-C6)alkyl-O—(C1-C6)alkyl (pour ex 46) groups, wherein R18, R19, R20, R21 and Alk are as defined below,
R18 and R19, identical or different, represent a hydrogen atom or a (C1-C6)alkyl group,
R20 represents a phenyl or heteroaryl group (such as a pyridinyl, pyrazolyl or pyrimidinyl group), which is optionally substituted with one or more (C1-C6)alkyl groups,
R21 represents a heterocycloalkyl group chosen among the morpholinyl and piperidinyl groups, and
Alk represents a (C1-C6)alkyl group which is linear or branched and which is optionally substituted with one to three hydroxyl groups.

Mention may also be made of the compounds wherein R1 represents a group of formula -L-R12, wherein L represents a bond or a —CH$_2$— or —CO— linkage and R12 represents a group of formula (e):

(e)

wherein:
R16 represents a hydrogen atom or an Alk group, wherein Alk is as defined below,
R17 represents an -Alk, -Alk-R20 or -Alk-R21 or —CO—(C1-C6)alkyl, —CO—(C3-C8)cycloalkyl, —CO-heterocycloalkyl group, wherein Alk, R20 and R21 are as defined below,
R20 represents a phenyl or heteroaryl group (such as a benzimidazolyl group), which is optionally substituted with one or more halogen atoms or (C1-C6)alkyl, hydroxyl or (C1-C4)alkoxy groups,
R21 represents a heterocycloalkyl group chosen among the piperidinyl and pyrrolidinyl groups, which is optionally substituted with one or more halogen atoms or (C1-C6) alkyl, hydroxyl or (C1-C4)alkoxy groups, and
Alk represents a (C1-C6)alkyl group which is linear or branched and which is optionally substituted with one to three groups, identical or different, chosen among the halogen atoms and the hydroxyl, phenyl, (C1-C4)alkoxy and —NR18R19 groups, wherein R18 and R19, identical or different, represent a hydrogen atom or a (C1-C6) alkyl group.

Mention may also be made of the compounds wherein R1 represents a group of formula -L-R12, wherein L represents a —CH$_2$— or —CO— linkage and R12 represents a group of formula (e):

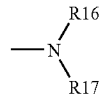
(e)

wherein:
R16 represents a hydrogen atom or an Alk group, wherein Alk is as defined below,
R17 represents an -Alk, -Alk-R20 or -Alk-R21 group, wherein Alk, R20 and R21 are as defined below,
R20 represents a phenyl or heteroaryl group (such as a benzimidazolyl group), which is optionally substituted, with one or more halogen atoms or (C1-C6)alkyl, hydroxyl or (C1-C4)alkoxy groups,
R21 represents a heterocycloalkyl group chosen among the piperidinyl and pyrrolidinyl groups, which is optionally substituted with one or more halogen atoms, or (C1-C6) alkyl, hydroxyl or (C1-C4)alkoxy groups, and
Alk represents a (C1-C6)alkyl group which is linear or branched and which is optionally substituted with one to three groups, identical or different, chosen among the halogen atoms and the hydroxyl, phenyl, (C1-C4)alkoxy and —NR18R19 groups, wherein R18 and R19, identical or different, represent a hydrogen atom or a (C1-C6) alkyl group.

Mention may also be made of the compounds wherein R1 represents a group of formula -L-R12, wherein L represents a bond or a —CH$_2$— or —CO— linkage and R12 represents a group of formula (e):

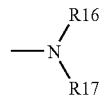
(e)

wherein:
R16 represents a hydrogen atom or an Alk group, wherein Alk is as defined below,
R17 represents an -Alk, -Alk-R20 or -Alk-R21 or —CO—(C1-C6)alkyl, —CO—(C3-C8)cycloalkyl, —CO-heterocycloalkyl group, wherein Alk, R20 and R21 are as defined below,
R20 represents a heteroaryl group (such as a benzimidazolyl group),
R21 represents a heterocycloalkyl group chosen among the piperidinyl and pyrrolidinyl groups, which is optionally substituted with one or more (C1-C6)alkyl or hydroxyl groups, and
Alk represents a (C1-C6)alkyl group which is linear or branched and which is optionally substituted with one to three groups, identical or different, chosen among the phenyl and —NR18R19 groups, wherein R18 and R19, identical or different, represent a (C1-C6)alkyl group.

In another embodiment of the invention, the compounds of formula (I) are such that R2 represents a hydrogen or halogen atom, or an (C1-C6) alkoxy or (C1-C6)alkyl group.

In another embodiment of the invention, the compounds of formula (I) are such that Q represents an oxygen atom or a —CH$_2$— link and R3 represents a linear (C1-C10)alkyl group which is optionally substituted by one to three groups, identical or different, chosen among the halogen atoms and the (C1-C4)alkoxy groups.

In another embodiment of the invention, the compounds of formula (I) are such that R3-Q- represents a CH$_3$—O—(CH$_2$)$_3$—O— or CF$_3$—(CH$_2$)$_2$—O— or CH$_3$O—CH$_2$—CF$_2$CH$_2$—O— or CH$_3$O—(CH$_2$)$_4$— group.

In another embodiment of the invention, the compounds of formula (I) are such that R4 represents a hydrogen atom.

In another embodiment of the invention, the compounds of formula (I) are such that R7 and R8 represent hydrogen atoms or (C1-C4)alkyl groups.

In another embodiment of the invention, the compounds of formula (I) are such that R7 and R8 together form, with the carbon atom to which they are attached, a (C3-C6)cycloalkyl group.

In another embodiment of the invention, the compounds of formula (I) are such that R9 and R10 represent hydrogen atoms or, when R11=H, R9 and R10 together form a linear (C2-C3)alkylene chain being optionally substituted by one to three groups chosen among: (C1-C4)alkyl, oxo, hydroxyl and amino groups.

In another embodiment of the invention, the compounds of formula (I) are such that R9 and R10 represent hydrogen atoms or, when R11=H, R9 and R10 together form a linear (C2-C3)alkylene chain being optionally substituted by one to three groups chosen among: (C1-C4)alkyl, oxo groups.

In another embodiment of the invention, the compounds of formula (I) are such that R11 represents a hydrogen atom or a (C1-C5)alkyl or (C3-C6)cycloalkyl group, which is optionally substituted by one to three groups chosen among: halogen atoms, hydroxyl, cyano, (C1-C6)alkoxy, —NR18R19, —COOR18, —CO—NR18R19, (C3-C6)cycloalkyl or pyridinyl groups, wherein R18 and R19, identical or different, represent a hydrogen atom or a (C1-C6)alkyl group.

In another embodiment of the invention, the compounds of formula (I) are such that R11 represents a hydrogen atom or a (C1-C5)alkyl or (C3-C6)cycloalkyl group, which is optionally substituted by one to three groups chosen among: halogen atoms, hydroxyl, (C1-C6)alkoxy, —NR18R19 or (C3-C6)cycloalkyl groups, wherein R18 and R19 are as defined above.

In another embodiment of the invention, the compounds of formula (I) are such that R11 represents a hydrogen atom or a (C1-C4)alkyl or (C3-C6)cycloalkyl group, which is optionally substituted by one to three groups chosen among: halogen atoms, hydroxyl, cyano, (C1-C6)alkoxy, —NR18R19, —COOR18, —CO—NR18R19 or pyridinyl groups, wherein R18 and R19 are as defined above.

Among the compounds of formula (I), the following compounds may be mentioned:

N-carbamimidoyl-3-{2-(3-methoxypropoxy)-4'-[(4-methylpiperazin-1-yl)methyl]biphenyl-4-yl}propanamide N-carbamimidoyl-3-[4'-{[4-(dimethylamino)piperidin-1-yl]methyl}-2-(3-methoxypropoxy)biphenyl-4-yl]propanamide N-(butylcarbamimidoyl)-3-{2-(3-methoxypropoxy)-4'-[(4-methylpiperazin-1-yl)methyl]biphenyl-4-yl}propanamide N-(butylcarbamimidoyl)-3-[4'-{[4-(dimethylamino)piperidin-1-yl]methyl}-2-(3-methoxypropoxy)biphenyl-4-yl]propanamide N-{[3-(diethylamino)propyl]carbamimidoyl}-3-[4'-{[4-(dimethylamino)piperidin-1-yl]methyl}-2-(3-methoxypropoxy)biphenyl-4-yl]propanamide 3-[4'-{[4-(dimethylamino)piperidin-1-yl]methyl}-2-(3-methoxypropoxy)biphenyl-4-yl]-N-[(2-pyridin-2-ylethyl)carbamimidoyl]propanamide 3-[4'-{[4-(dimethylamino)piperidin-1-yl]methyl}-2-(3-methoxypropoxy)biphenyl-4-yl]-N-[(3-hydroxybutyl)carbamimidoyl]propanamide 3-[4'-{[4-(dimethylamino)piperidin-1-yl]methyl}-2-(3-methoxypropoxy)biphenyl-4-yl]-N-[(3-methoxypropyl)carbamimidoyl]propanamide N-[(2-cyclopropylethyl)carbamimidoyl]-3-[4'-{[4-(dimethylamino)piperidin-1-yl]methyl}-2-(3-methoxypropoxy)biphenyl-4-yl]propanamide N-(butylcarbamimidoyl)-3-[2-(3-methoxypropoxy)biphenyl-4-yl]propanamide 3-[4'-{[4-(dimethylamino)piperidin-1-yl]methyl}-2-(3-methoxypropoxy)biphenyl-4-yl]-N-[(3-methylbutyl)carbamimidoyl]propanamide N-(butylcarbamimidoyl)-3-[2-(3-methoxypropoxy)-4'-(piperidin-1-ylmethyl)biphenyl-4-yl]propanamide N-carbamimidoyl-3-[2-(3-methoxypropoxy)-4'-(piperidin-1-ylmethyl)biphenyl-4-yl]propanamide 3-{4'-[(4-acetylpiperazin-1-yl)methyl]-2-(3-methoxypropoxy)biphenyl-4-yl}-N-carbamimidoylpropanamide 3-{4'-[(4-acetylpiperazin-1-yl)methyl]-2-(3-methoxypropoxy)biphenyl-4-yl}N-(butylcarbamimidoyl)propanamide N-(cyclopropylcarbamimidoyl)-3-[4'-{[4-(dimethylamino)piperidin-1-yl]methyl}-2-(3-methoxypropoxy)biphenyl-4-yl]propanamide N-carbamimidoyl-3-{2-(3-methoxypropoxy)-4'-[(4-methylpiperazin-1-yl)carbonyl]biphenyl-4-yl}propanamide N-carbamimidoyl-3-[4'-{[4-(dimethylamino)piperidin-1-yl]methyl}-2-(3-methoxypropoxy)biphenyl-4-yl]butanamide N-(butylcarbamimidoyl)-3-[2-(3-methoxypropoxy)-4'-{[4-(methylamino)piperidin-1-yl]methyl}biphenyl-4-yl]propanamide 3-[4'-{[4-(dimethylamino)piperidin-1-yl]methyl}-2-(3-methoxypropoxy)biphenyl-4-yl]-N-(methylcarbamimidoyl)propanamide N-carbamimidoyl-3-[3-(3-methoxypropoxy)-4-pyridin-3-ylphenyl]propanamide N-carbamimidoyl-3-[4'-{[4-(dimethylamino)piperidin-1-yl]methyl}-2-(3-methoxypropoxy)biphenyl-4-yl]-3-methylbutanamide N-carbamimidoyl-3-[3-(3-methoxypropoxy)-4-pyrimidin-5-ylphenyl]propanamide 3-{4'-[(4-acetylpiperazin-1-yl)methyl]-2-(3-methoxypropoxy)biphenyl-4-yl}-N-[(2-hydroxybutyl)carbamimidoyl]propanamide 3-{2-(3-methoxypropoxy)-4'-[(4-methylpiperazin-1-yl)carbonyl]biphenyl-4-yl}-3-methyl-N-(propylcarbamimidoyl)butanamide 3-{4'-[(4-acetylpiperazin-1-yl)methyl]-2-(3-methoxypropoxy)biphenyl-4-yl}-N-(propylcarbamimidoyl)propanamide 3-[2-(3-methoxypropoxy)-4'-(morpholin-4-ylcarbonyl)biphenyl-4-yl]-N-(propylcarbamimidoyl)propanamide N-(butylcarbamimidoyl)-3-[2-(3-methoxypropoxy)-4'-{[4-(phenylcarbonyl)piperazin-1-yl]methyl}biphenyl-4-yl]propanamide trifluoroacetate N-(butylcarbamimidoyl)-3-[2-(3-methoxypropoxy)-4'-{[4-(pyridin-3-ylmethyl)piperazin-1-yl]methyl}biphenyl-4-yl]propanamide trifluoroacetate N-(butylcarbamimidoyl)-3-[4'-({4-[2-(dimethylamino)-2-oxoethyl]piperazin-1-yl}methyl)-2-(3-methoxypropoxy)biphenyl-4-yl]propanamide trifluoroacetate N-(butylcarbamimidoyl)-3-[4'-{[4-(dipropylamino)piperidin-1-yl]methyl}-2-(3-methoxypropoxy)biphenyl-4-yl]propanamide trifluoroacetate N-(butylcarbamimidoyl)-3-[2-(3-methoxypropoxy)-4'-{[4-(pyridin-4-ylmethyl)piperazin-1-yl]methyl}biphenyl-4-yl]propanamide trifluoroacetate N-(butylcarbamimidoyl)-3-{2-(3-methoxypropoxy)-4'-[(4-pyrrolidin-1-ylpiperidin-1-yl)methyl]biphenyl-4-yl}propanamide trifluoroacetate N-(butylcarbamimidoyl)-3-[4'-({[2-(dimethylamino)ethyl]amino}methyl)-2-(3-methoxypropoxy)biphenyl-4-yl]propanamide trifluoroacetate N-(butylcarbamimidoyl)-3-[2-(3-methoxypropoxy)-4'-{[4-(morpholin-4-ylcarbonyl)piperazin-1-yl]methyl}biphenyl-4-yl]propanamide trifluoroacetate N-(butylcarbamimidoyl)-3-[2-(3-methoxypropoxy)-4'-{[4-(piperidin-1-ylcarbonyl)piperazin-1-yl]methyl}biphenyl-4-yl]propanamide trifluoroacetate N-(butylcarbamimidoyl)-3-[2-(3-methoxypropoxy)-4'-{[4-(pyridin-3-ylcarbonyl)piperazin-1-yl]methyl}biphenyl-4-yl]propanamide trifluoroacetate N-(butylcarbamimidoyl)-3-{4'-[(3,5-dimethylpiperazin-1-yl)methyl]-2-(3-methoxypropoxy)biphenyl-4-yl}propanamide trifluoroacetate N-(butylcarbamimidoyl)-3-[2-(3-methoxypropoxy)-4'-({4-[(1-methyl-1H-pyrazol-4-yl)methyl]piperazin-1-yl}methyl)biphenyl-4-yl]propanamide trifluoroacetate N-(butylcarbamimidoyl)-3-[4'-({[2-(diethylamino)-1-methylethyl]amino}methyl)-2-(3-methoxypropoxy)biphenyl-4-yl]propanamide trifluoroacetate 3-[4'-({4-[benzyl(ethyl)amino]piperidin-1-yl}methyl)-2-(3-methoxypropoxy)biphenyl-yl]-N-(butylcarbamimidoyl)propanamide trifluoroacetate N-(butylcarbamimidoyl)-3-[4'-{[4-(2,2-dimethylpropanoyl)piperazin-1-yl]methyl}-2-(3-methoxypropoxy)biphenyl-4-yl]propanamide trifluoroacetate.

N-(butylcarbamimidoyl)-3-{4'-[(4-cyclohexylpiperazin-1-yl)methyl]-2-(3-methoxypropoxy)biphenyl-4-yl}propanamide trifluoroacetate N-(butylcarbamimidoyl)-3-[4'-({[(1-ethylpyrrolidin-2-yl)methyl]amino}methyl)-2-(3-methoxypropoxy)biphenyl-4-yl]propanamide trifluoroacetate N-(butylcarbamimidoyl)-3-[2-(3-methoxypropoxy)-4'-{[4-(2-methylpropyl)piperazin-1-yl]methyl}biphenyl-4-yl]propanamide trifluoroacetate N-(butylcarbamimidoyl)-3-[2-(3-methoxypropoxy)-4'-[{(3-methoxypropyl)piperazin-1-yl]methyl}biphenyl-4-yl]propanamide trifluoroacetate N-(butylcarbamimidoyl)-3-[2-(3-methoxypropoxy)-4'-{[methyl(1-methylpyrrolidin-3-yl)amino]methyl}biphenyl-4-yl]propanamide trifluoroacetate N-(butylcarbamimidoyl)-3-[4'-({[2-(dimethylamino)-2-phenylethyl]amino}methyl)-2-(3-methoxypropoxy)biphenyl-4-yl]propanamide trifluoroacetate N-(butylcarbamimidoyl)-3-{2-(3-methoxypropoxy)-4'-[(4-pyridin-2-ylpiperazin-1-yl)methyl]biphenyl-4-yl}propanamide trifluoroacetate N-(butylcarbamimidoyl)-3-{4'-[(4-cyclopentylpiperazin-1-yl)methyl]-2-(3-methoxypropoxy)biphenyl-4-yl}propanamide trifluoroacetate 3-[4'-({benzyl[2-(dimethylamino)ethyl]amino}methyl)-2-(3-methoxypropoxy)biphenyl-4-yl]-N-(butylcarbamimidoyl)propanamide trifluoroacetate 3-{4'-[(4-benzyl-3-oxopiperazin-1-yl)methyl]-2-(3-methoxypropoxy)biphenyl-4-yl}N-(butylcarbamimidoyl)propanamide trifluoroacetate N-(butylcarbamimidoyl)-3-[4'-{[4-(diethylamino)piperidin-1-yl]methyl}-2-(3-methoxypropoxy)biphenyl-4-yl]propanamide trifluoroacetate N-(butylcarbamimidoyl)-3-[4'-{[4-(1-ethylpropyl)piperazin-1-yl]methyl}-2-(3-methoxypropoxy)biphenyl-4-yl]propanamide trifluoroacetate N-(butylcarbamimidoyl)-3-[4'-({[2-(dimethylamino)ethyl](ethyl)amino}methyl)-2-(3-methoxypropoxy)biphenyl-4-yl]propanamide trifluoroacetate N-(butylcarbamimidoyl)-3-[2-(3-methoxypropoxy)-4'-{[4-(tetrahydrofuran-2-ylmethyl)piperazin-1-yl]methyl}biphenyl-4-yl]propanamide trifluoroacetate N-(butylcarbamimidoyl)-3-[4'-{[(3R)-3-(dimethylamino)pyrrolidin-1-yl]methyl}-2-(3-methoxypropoxy)biphenyl-4-yl]propanamide trifluoroacetate N-(butylcarbamimidoyl)-3-{2-(3-methoxypropoxy)-4'-[(4-pyridin-4-ylpiperazin-1-yl)methyl]biphenyl-4-yl}propanamide trifluoroacetate N-(butylcarbamimidoyl)-3-{2-(3-methoxypropoxy)-4'-[(4-pyrimidin-2-ylpiperazin-1-yl)methyl]biphenyl-4-yl}propanamide trifluoroacetate 3-[4'-(1,4'-bipiperidin-1'-ylmethyl)-2-(3-methoxypropoxy)biphenyl-4-yl]-N-(butylcarbamimidoyl)propanamide trifluoroacetate N-(butylcarbamimidoyl)-3-[2-(3-methoxypropoxy)-4'-{[(1-phenyl-2-pyrrolidin-1-ylethyl)amino]methyl}biphenyl-4-yl]propanamide trifluoroacetate N-(butylcarbamimidoyl)-3-{2-(3-methoxypropoxy)-4'-[(4-methyl-1,4'-bipiperidin-1'-yl)methyl]biphenyl-4-yl}propanamide trifluoroacetate N-(butylcarbamimidoyl)-3-[2-(3-methoxypropoxy)-4'-{[(2-piperidin-1-ylethyl)amino]methyl}biphenyl-4-yl]propanamide trifluoroacetate 3-{4'-[(4-benzylpiperazin-1-yl)methyl]-2-(3-methoxypropoxy)biphenyl-4-yl}-N-(butylcarbamimidoyl)propanamide trifluoroacetate N-(butylcarbamimidoyl)-3-[4'-({[2-(4-hydroxypiperidin-1-yl)ethyl]amino}methyl)-2-(3-methoxypropoxy)biphenyl-4-yl]propanamide trifluoroacetate (salt)

N-(butylcarbamimidoyl)-3-{4'-[(4-butylpiperazin-1-yl)methyl]-2-(3-methoxypropoxy)biphenyl-4-yl}propanamide trifluoroacetate 3-[4'-({[2-(1H-benzimidazol-1-yl)ethyl]amino}methyl)-2-(3-methoxypropoxy)biphenyl-4-yl]-N-(butylcarbamimidoyl)propanamide trifluoroacetate N-(butylcarbamimidoyl)-3-{2-(3-methoxypropoxy)-4'-[(3-phenylpiperazin-1-yl)methyl]biphenyl-4-yl}propanamide trifluoroacetate N-(butylcarbamimidoyl)-3-{2-(3-methoxypropoxy)-4'-[(4-morpholin-4-ylpiperidin-1-yl)methyl]biphenyl-4-yl}propanamide trifluoroacetate N-(butylcarbamimidoyl)-3-[2-(3-methoxypropoxy)-4'-{[4-(2-methylphenyl)piperazin-1-yl]methyl}biphenyl-4-yl]propanamide trifluoroacetate tert-butyl[1-({4'-[3-(butylcarbamimidamido)-3-oxopropyl]-2'-(3-methoxypropoxy)biphenyl-4-yl}methyl)piperidin-4-yl]methylcarbamate trifluoroacetate N-(butylcarbamimidoyl)-3-[4'-{[4-(2-hydroxyethyl)piperazin-1-yl]methyl}-2-(3-methoxypropoxy)biphenyl-4-yl]propanamide trifluoroacetate (salt)

N-(butylcarbamimidoyl)-3-[2-(3-methoxypropoxy)-4'-{[4-(1-methylethyl)piperazin-1-yl]methyl}biphenyl-4-yl]propanamide trifluoroacetate N-(butylcarbamimidoyl)-3-[4'-{[4-(2,6-dimethylmorpholin-4-yl)piperidin-1-yl]methyl}-2-(3-methoxypropoxy)biphenyl-4-yl]propanamide trifluoroacetate N-(butylcarbamimidoyl)-3-[2-(3-methoxypropoxy)-4'-{[4-(2-phenylethyl)piperazin-1-yl]methyl}biphenyl-4-yl]propanamide trifluoroacetate N-(butylcarbamimidoyl)-3-[2-(3-methoxypropoxy)-4'-{[4-(1-phenylethyl)piperazin-1-yl]methyl}biphenyl-4-yl]propanamide trifluoroacetate
N-carbamimidoyl-3-[2-(3-methoxypropoxy)-4'-(piperidin-1-ylcarbonyl)biphenyl-4-yl]propanamide
N-carbamimidoyl-3-{2-(3-methoxypropoxy)-4'-[(4-methyl-2-oxopiperazin-1-yl)methyl]biphenyl-4-yl}propanamide
N-carbamimidoyl-3-{2-(3-methoxypropoxy)-4'-[(2-oxopiperidin-1-yl)methyl]biphenyl-4-yl}propanamide
N-carbamimidoyl-3-[2-(3-methoxypropoxy)-4'-(1-methylethoxy)biphenyl-4-yl]propanamide
3-{4'-[(4-acetylpiperazin-1-yl)carbonyl]-2-(3-methoxypropoxy)biphenyl-4-yl}-N-carbamimidoylpropanamide
N-(butylcarbamimidoyl)-3-[2-(3-methoxypropoxy)-4'-(1-methylethoxy)biphenyl-4-yl]propanamide
N-carbamimidoyl-3-[2-(3-methoxypropoxy)-4'-(methylsulfonyl)biphenyl-4-yl]propanamide
N-carbamimidoyl-3-{2-(3-methoxypropoxy)-4'-[(1-methylethyl)sulfonyl]biphenyl-4-yl}propanamide
N-carbamimidoyl-3-[4'-(ethylsulfonyl)-2-(3-methoxypropoxy)biphenyl-4-yl]propanamide
N-carbamimidoyl-3-[2-(3-methoxypropoxy)-4'-(morpholin-4-ylcarbonyl)biphenyl-4-yl]propanamide
3-{4'-[(4-tert-butylpiperidin-1-yl)carbonyl]-2-(3-methoxypropoxy)biphenyl-4-yl}-N-carbamimidoylpropanamide
N-carbamimidoyl-3-{4'-[(4-hydroxypiperidin-1-yl)carbonyl]-2-(3-methoxypropoxy)biphenyl-4-yl}propanamide
3-[4'-{[4-(dimethylamino)piperidin-1-yl]methyl}-2-(3-methoxypropoxy)biphenyl-4-yl]-N-[(2-methylpropyl)carbamimidoyl]propanamide
3-[3-(3-methoxpropoxy)-4-(6-morpholin-4-ylpyridin-3-yl)phenyl]-N-(methylcarbamimidoyl)propanamide
3-[2-(3-methoxypropoxy)-4'-morpholin-4-ylbiphenyl-4-yl]-N-(methylcarbamimidoyl)propanamide
3-[2-(3-methoxypropoxy)-4'-(piperidin-1-ylsulfonyl)biphenyl-4-yl]-N-(methylcarbamimidoyl)propanamide
N-carbamimidoyl-3-[2'-ethoxy-2-(3-methoxypropoxy)biphenyl-4-yl]propanamide
N-carbamimidoyl-3-[3-(3-methoxypropoxy)-4-(1H-pyrazol-3-yl)phenyl]propanamide
N-carbamimidoyl-3-[4-(2,4-dimethoxypyrimidin-5-yl)-3-(3-methoxypropoxy)phenyl]propanamide
N-carbamimidoyl-3-{4-[6-(dimethylamino)pyridin-3-yl]-3-(3-methoxypropoxy)phenyl}propanamide
N-carbamimidoyl-3-[2-(3-methoxypropoxy)-4'-(piperidin-1-ylsulfonyl)biphenyl-4-yl]propanamide
N-carbamimidoyl-3-[4'-(cyclopropylmethoxy)-2-(3-methoxypropoxy)biphenyl-4-yl]propanamide
N-carbamimidoyl-3-[4'-{[4-(dimethylamino)piperidin-1-yl]methyl}-2-(3-methoxypropoxy)biphenyl-4-yl]-2-methylpropanamide
N-carbamimidoyl-3-[2-(3-methoxypropoxy)-4'-(morpholin-4-ylsulfonyl)biphenyl-4-yl]propanamide
N-carbamimidoyl-3-{4'-[(4 dimethylpiperidin-1-yl)carbonyl]-2-(3-methoxypropoxy)biphenyl-4-yl}propanamide
3-[4'-bromo-2'-fluoro-2-(3-methoxypropoxy)biphenyl-4-yl]-N-carbamimidoylpropanamide
N-carbamimidoyl-3-[4'-ethoxy-3'-fluoro-2-(3-methoxypropoxy)biphenyl-4-yl]propanamide
N-carbamimidoyl-3-[2-(3-methoxypropoxy)-3'-(piperidin-1-ylcarbonyl)biphenyl-4-yl]propanamide
N-carbamimidoyl-3-[2-(3-methoxypropoxy)-3'-(morpholinylmethyl)biphenyl-4-yl]propanamide
N-carbamimidoyl-3-[2-(3-methoxypropoxy)-3'-(methylsulfonyl)biphenyl-4-yl]propanamide
3-[4-(2,1,3-benzoxadiazol-5-yl)-3-(3-methoxypropoxy)phenyl]-N-carbamimidoylpropanamide
3-[4-(1-benzyl-1H-pyrazol-4-yl)-3-(3-methoxypropoxy)phenyl]-N-carbamimidoylpropanamide
N-carbamimidoyl-3-[2'-fluoro-2-(3-methoxypropoxy)-3'-methylbiphenyl-4-yl]propanamide
N-carbamimidoyl-3-[4'-chloro-2-(3-methoxypropoxy)-3'-methylbiphenyl-4-yl]propanamide
N-carbamimidoyl-3-[3',4'-dichloro-2-(3-methoxypropoxy)biphenyl-4-yl]propanamide
N-carbamimidoyl-3-[4'-fluoro-2-(3-methoxypropoxy)-3'-methylbiphenyl-4-yl]propanamide
N-carbamimidoyl-3-[3',4'-difluoro-2-(3-methoxypropoxy)biphenyl-4-yl]propanamide
N-carbamimidoyl-3-[4'-methoxy-2-(3-methoxypropoxy)-3'-methylbiphenyl-4-yl]propanamide
N-carbamimidoyl-3-[3',5'-difluoro-2-(3-methoxypropoxy)biphenyl-4-yl]propanamide
N-carbamimidoyl-3-[3'-fluoro-5'-methoxy-2-(3-methoxypropoxy)biphenyl-4-yl]propanamide
4'-(3-carbamimidamido-3-oxopropyl)-2'-(3-methoxypropoxy)-N,N-dimethylbiphenyl-3-carboxamide
N-carbamimidoyl-3-[2-(3-methoxypropoxy)-3'-(trifluoromethyl)biphenyl-4-yl]propanamide
N-carbamimidoyl-3-[2-(3-methoxypropoxy)-3'-(1-methylethyl)biphenyl-4-yl]propanamide
N-carbamimidoyl-3-[3'-(methoxymethyl)-2-(3-methoxypropoxy)biphenyl-4-yl]propanamide
N-carbamimidoyl-3-[2-(3-methoxypropoxy)-3'-methylbiphenyl-4-yl]propanamide
N-carbamimidoyl-3-[3'-chloro-2-(3-methoxypropoxy)biphenyl-4-yl]propanamide
N-carbamimidoyl-3-[2'-fluoro-3'-methoxy-2-(3-methoxypropoxy)biphenyl-4-yl]propanamide
N-carbamimidoyl-3-[2-(3-methoxypropoxy)-3'-(1H-pyrazol-1-yl)biphenyl-4-yl]propanamide
N-carbamimidoyl-3-[2-(3-methoxypropoxy)-3'-(1-methylethoxy)biphenyl-4-yl]propanamide
N-carbamimidoyl-3-[2-(3-methoxypropoxy)-3'-propoxybiphenyl-4-yl]propanamide
N-carbamimidoyl-3-[3'-ethoxy-2-(3-methoxypropoxy)biphenyl-4-yl]propanamide
N-carbamimidoyl-3-[3'-(cyclopropylmethoxy)-2-(3-methoxypropoxy)biphenyl-4-yl]propanamide
N-carbamimidoyl-3 [3'-methoxy-2-(3-methoxypropoxy)biphenyl-4-yl]propanamide
4'-(3-carbamimidamido-3-oxopropyl)-2'-(3-methoxypropoxy)-N,N-dimethylbiphenyl-4-carboxamide
N-carbamimidoyl-3-[2-(3-methoxypropoxy)-4'-(trifluoromethyl)biphenyl-4-yl]propanamide
N-carbamimidoyl-3-[2-(3-methoxypropoxy)-4'-(1-methylethyl)biphenyl-4-yl]propanamide
N-carbamimidoyl-3-[2-(3-methoxypropoxy)-4'-(2-methylpropyl)biphenyl-4-yl]propanamide
N-carbamimidoyl-3-[4'-ethyl-2-(3-methoxypropoxy)biphenyl-4-yl]propanamide
N-carbamimidoyl-3-[4'-(methoxymethyl)-2-(3-methoxypropoxy)biphenyl-4-yl]propanamide
N-carbamimidoyl-3-[2-(3-methoxypropoxy)-4'-(1-methylethoxy)biphenyl-4-yl]propanamide
N-carbamimidoyl-3-[4'-ethoxy-2-(3-methoxypropoxy)biphenyl-4-yl]propanamide
N-carbamimidoyl-3-[4'-methoxy-2-(3-methoxypropoxy)biphenyl-4-yl]propanamide
N-carbamimidoyl-3-[3-(3-methoxypropoxy)-4-pyridin-4-ylphenyl]propanamide
N-carbamimidoyl-3-[4-(2,3-dihydro-1-benzofuran-5-yl)-3-(3-methoxypropoxy)phenyl]propanamide N-carbamimidoyl-3-[4-(3,4-dihydro-2H-1,5-benzodioxepin-7-yl)-3-(3-methoxypropoxy)phenyl]propanamide
N-carbamimidoyl-3-[4-(2,3-dihydro-1,4-benzodioxin-6-yl)-3-(3-methoxypropoxy)phenyl]propanamide
3-[4-(1,3-benzodioxol-5-yl)-3-(3-methoxypropoxy)phenyl]-N-carbamimidoylpropanamide
N-carbamimidoyl-3-[4-(1H-indazol-6-yl)-3-(3-methoxypropoxy)phenyl]propanamide
3-[4-(1-benzothiophen-2-yl)-3-(3-methoxypropoxy)phenyl]-N-carbamimidoylpropanamide
N-carbamimidoyl-3-[4'-chloro-2'-methoxy-2-(3-methoxypropoxy)biphenyl-4-yl]propanamide
N-carbamimidoyl-3-[4'-fluoro-2-(3-methoxypropoxy)-2'-methylbiphenyl-4-yl]propanamide
N-carbamimidoyl-3-[2',4'-difluoro-2-(3-methoxypropoxy)biphenyl-4-yl]propanamide
N-carbamimidoyl-3-[4'-fluoro-2-(3-methoxypropoxy)-2'-(1-methylethoxy)biphenyl-4-yl]propanamide
N-carbamimidoyl-3-[2'-chloro-4'-methoxy-2-(3-methoxypropoxy)biphenyl-4-yl]propanamide
N-carbamimidoyl-3-[5'-fluoro-2-(3-methoxypropoxy)-2'-(1-methylethoxy)biphenyl-4-yl]propanamide
N-carbamimidoyl-3-[2-(3-methoxypropoxy)-3',4'-dimethylbiphenyl-4-yl]propanamide
N-carbamimidoyl-3-[3'-fluoro-2-(3-methoxypropoxy)-4'-methylbiphenyl-4-yl]propanamide
N-carbamimidoyl-3-[3-(3-methoxypropoxy)-4-(1,3-thiazol-2-yl)phenyl]propanamide
N-(butylcarbamimidoyl)-3-[4'-fluoro-2-(3-methoxypropoxy)biphenyl-4-yl]propanamide
4'-(3-carbamimidamido-3-oxopropyl)-N,N-diethyl-2'-(3-methoxypropoxy)biphenyl-4-carboxamide
N-carbamimidoyl-3-[2-(3-methoxypropoxy)-4'-(1H-1,2,4-triazol-1-ylmethyl)biphenyl-4-yl]propanamide
N-carbamimidoyl-3-{2-(3-methoxypropoxy)-4'-[(3-methyl-2-oxoimidazolidin-1-yl)methyl]biphenyl-4-yl}propanamide
N-carbamimidoyl-3-[3-(3-methoxypropoxy)-4-pyridazin-3-ylphenyl]propanamide
N-carbamimidoyl-3-[2-(3-methoxypropoxy)-4'-(2-oxopiperidin-1-yl)biphenyl-4-yl]propanamide
N-carbamimidoyl-3-{2-(3-methoxypropoxy)-4'-[(2-oxopyrrolidin-1-yl)methyl]biphenyl-4-yl}propanamide
N-carbamimidoyl-3-{2-(3-methoxypropoxy)-4'-[(4-methyl-2,5-dioxopiperazin-1-yl)methyl]biphenyl-4-yl}propanamide
N-carbamimidoyl-3-[3-(3-methoxypropoxy)-4-pyrimidin-2-ylphenyl]propanamide
N-carbamimidoyl-3-{4'-[(cyclopropylmethyl)sulfonyl]-2-(3-methoxypropoxy)biphenyl-4-yl}propanamide
N-carbamimidoyl-3-[4'-(cyclopentylsulfonyl)-2-(3-methoxypropoxy)biphenyl-4-yl]propanamide
3-{3'-[(tert-butylsulfonyl)methyl]-2-(3-methoxypropoxy)biphenyl-4-yl}N-(methylcarbamimidoyl)propanamide
N-carbamimidoyl-3-[2-(3-methoxypropoxy)biphenyl-4-yl]propanamide.
3-[3-(3-methoxypropoxy)-4-(1,3-oxazol-2-yl)phenyl]-N-(methylcarbamimidoyl)propanamide
3-{2-(3-methoxypropoxy)-4'-[(2-oxopiperidin-1-yl)methyl]biphenyl-4-yl}-N-(methylcarbamimidoyl)propanamide
N-carbamimidoyl-3-{2-(3-methoxypropoxy)-3'-[(3-methyl-2-oxoimidazolidin-1-yl)methyl]biphenyl-4-yl}propanamide
3-{4-[3-(acetylamino)-1H-pyrazol-1-yl]-3-(3-methoxypropoxy)phenyl}-N-carbamimidoylpropanamide
3-[2-(3-methoxypropoxy)-4'-(1H-1,2,4-triazol-1-ylmethyl)biphenyl-4-yl]-N-(methylcarbamimidoyl)propanamide
3-{3'-[2-(tert-butylsulfonyl)ethyl]-2-(3-methoxypropoxy)biphenyl-4-yl}-N-(methylcarbamimidoyl)propanamide
3-[2-(3-methoxypropoxy)-3'-(1H-1,2,4-triazol-1-ylmethyl)biphenyl-4-yl]-N-(methylcarbamimidoyl)propanamide
N-carbamimidoyl-3-[2-(3-methoxypropoxy)-3'-(1H-1,2,4-triazol-1-ylmethyl)biphenyl-4-yl]propanamide
N-carbamimidoyl-3-{2-(3-methoxypropoxy)-3'-[(2-oxopiperidin-1-yl)methyl]biphenyl-4-yl}propanamide
3-[4-(3,5-dimethylisoxazol-4-yl)-3-(3-methoxypropoxy)phenyl]-N-(methylcarbamimidoyl)propanamide
3-[2-(3-methoxypropoxy)-4'-(2-oxo-2-piperidin-1-ylethyl)biphenyl-4-yl]-N-(methylcarbamimidoyl)propanamide
3-{2-(3-methoxypropoxy)-3'-[(2-oxopiperidin-1-yl)methyl]biphenyl-4-yl}-N-(methylcarbamimidoyl)propanamide
3-{3'-[(tert-butylsulfonyl)methyl]-2-(3-methoxypropoxy)biphenyl-4-yl}-N-carbamimidoylpropanamide
3-{4'-[2-hydroxy-1 (hydroxymethyl)ethyl]-2-(3-methoxypropoxy)biphenyl-4-yl}-N-(methylcarbamimidoyl)propanamide
3-{4-[2-(tert-butylsulfonyl)-1,2,3,4-tetrahydroisoquinolin-5-yl]-3-(3-methoxypropoxy)phenyl})-N-(methylcarbamimidoyl)propanamide
N-{2'-(3-methoxypropoxy)-4'-[3-(methylcarbamimidamido)-3-oxopropyl]biphenyl-3-yl}cyclopentanecarboxamide
N-({2'-(3-methoxypropoxy)-4'-[3-(methylcarbamimidamido)-3-oxopropyl]biphenyl-3-yl}methyl)-2,2-dimethylpropanamide
3-[2-(3-methoxypropoxy)-3'-(2-oxopiperidin-1-yl)biphenyl-4-yl]-N-(methylcarbamimidoyl)propanamide
3-[2-(3-methbxypropoxy)-3'-(2-oxo-2-piperidin-1-ylethyl)biphenyl-4-yl]-N-(methylcarbamimidoyl)propanamide
3-{2-(3-methoxypropoxy)-3'-[(3-methyl-2-oxoimidazolidin-1-yl)methyl]biphenyl-4-yl}-N-[(3,3,3-trifluoropropyl)carbamimidoyl]propanamide
N-carbamimidoyl-3-{3'-[(3,4-dimethylpyrazolidin-1-yl)methyl]-2-(3-methoxypropoxy)biphenyl-4-yl}propanamide
3-{2-(3-methoxypropoxy)-3'-[(morpholin-4-ylsulfonyl)methyl]biphenyl-4-yl}-N-(methylcarbamimidoyl)propanamide
3-{2-(3-methoxypropoxy)-3'-[(pyrrolidin-1-ylsulfonyl)methyl]biphenyl-4-yl}-N-(methylcarbamimidoyl)propanamide
3-{3'-[(tert-butylsulfonyl)methyl]-4'-chloro-2-(3-methoxypropoxy)biphenyl-4-yl}-N-(methylcarbamimidoyl)propanamide
N-{2'-(3-methoxypropoxy)-4'-[3-(methylcarbamimidamido)-3-oxopropyl]biphenyl-3-yl}-N-methylmorpholine-4-carboxamide
N-[(2-hydroxyethyl)carbamimidoyl]-3-{2-(3-methoxypropoxy)-3'-[(3-methyl-2-oxoimidazolidin-1-yl)methyl]biphenyl-4-yl}propanamide
3-[3-(3-methoxypropoxy)-4-{4-[(3-methyl-2-oxoimidazolidin-1-yl)methyl]-1,3-thiazol-2-yl}phenyl]-N-(methylcarbamimidoyl)propanamide
3-[2-(3-methoxypropoxy)-3'-{[3-(1-methylethyl)-1H-pyrazol-1-yl]methyl}biphenyl-4-yl]-N-(methylcarbamimidoyl)propanamide
3-[4-{4-[(tert-butylsulfonyl)methyl]-1,3-thiazol-2-yl}-3-(3-methoxypropoxy)phenyl]-N-(methylcarbamimidoyl)propanamide
3-{4'-[(1-acetylpiperidin-4-yl)sulfonyl]-2-(3-methoxypropoxy)biphenyl-4-yl}-N-(methylcarbamimidoyl)propanamide
3-[3-(3-methoxypropoxy)-4-(1-methyl-1H-benzimidazol-6-yl)phenyl]-N-(methylcarbamimidoyl)propanamide 3-[3-(3-methoxypropoxy)-4-(2-methyl-1,3-benzothiazol-5-yl)phenyl]-N-(methylcarbamimidoyl)propanamide
3-{4-[1-(2,2-dimethylpropyl)-1H-benzimidazol-5-yl]-3-(3-methoxypropoxy)phenyl}-N-(methylcarbamimidoyl)propanamide
3-{3'-[(tert-butylsulfonyl)methyl]-2-(3-methoxypropoxy)biphenyl-4-yl}-N-carbamimidoyl-2,2-dimethylpropanamide
3-[3'-{[dihydroxy(morpholin-4-yl)-lambda-4~-sulfanyl]methyl}-2-(3-methoxypropoxy)biphenyl-4-yl]-N-[(4,4,4-trifluorobutyl)carbamimidoyl]propanamide
3-{2-(3-methoxypropoxy)-3'-[(morpholin-4-ylsulfonyl)methyl]biphenyl-4-yl}-N-[(1-methylethyl)carbamimidoyl]propanamide
N-(5,5-dimethyl-6-oxo-1,4,5,6-tetrahydropyrimidin-2-yl)-3-[2-(3-methoxypropoxy)biphenyl-4-yl]propanamide
N-carbamimidoyl-3-[3'-chloro-4'-fluoro-2-(3-methoxypropoxy)biphenyl-4-yl]propanamide
3-[4'-(8-azaspiro[4.5]dec-8-ylcarbonyl)-2-(3-methoxypropoxy)biphenyl-4-yl]-N-carbamimidoylpropanamide
N-carbamimidoyl-3-[3-(3-methoxypropoxy)-4-(1,3-thiazol-4-yl)phenyl]propanamide
3-{3-(4-methoxybutyl)-4-[3-(2-oxopiperidin-1-yl)phenoxy]phenyl}-N-(methylcarbamimidoyl)propanamide
3-{4-[2-(2,2-dimethylpropanoyl)-1,2,3,4-tetrahydroisoquinolin-5-yl]-3-(3-methoxypropoxy)phenyl}-N-(methylcarbamimidoyl)propanamide.

Among the compounds of formula (I), the following compounds may also be mentioned:
N-(methylcarbamimidoyl)-3-[3'-(morpholin-4-ylcarbonyl)-2-(3,3,3-trifluoropropoxy)biphenyl-4-yl]propanamide
3,3-dimethyl-N-{4'-[3-(methylcarbamimidamido)-3-oxopropyl]-2'-(3,3,3-trifluoropropoxy)biphenyl-3-yl}butanamide
3-[4'-{[4-(dimethylamino)piperidin-1-yl]methyl}-2-(3-methoxypropoxy)biphenyl-4-yl]-N-(5,5-dimethyl-4-oxo-1,4,5,6-tetrahydropyrimidin-2-yl)propanamide.

In accordance with the present invention, the compounds of formula (I) may be prepared according to the following process, described hereinafter in schemes 1-8 and in the examples.

A protecting group PG, as mentioned hereafter, corresponds to a group which enables, on the one hand, the protection of a reactive function such as a hydroxyl or an amine during a synthesis step and, on then other hand, to recover the intact reactive function at the end of the synthesis step. Examples of protecting groups, as well as methods for protecting and deprotecting various functional groups, are given in <<Protective Groups in Organic Synthesis>>, Green et al., 2$^{nd}$ Edition (John Wiley & Sons, Inc., New York).

A leaving group, as mentioned hereafter, corresponds to a group which may easily be cleaved from a molecule by breaking a heterolytic bond, with departure of electronic pair. This group may then easily be replaced by another functional group during a substitution reaction, for example. Such leaving groups may consist in halogen atoms or activated hydroxyl groups, such as mesylate, tosylate, triflate or acetyl groups, etc. Examples of leaving groups, as well as references relating to their preparation, are given in <<Advances in Organic Chemistry>>, J. March, 3$^{rd}$ Edition, Wiley Interscience, p. 310-316.

Scheme 1

Scheme 1 describes a process for obtaining the compounds of formula (I) according to the invention, wherein R5, R6, R7, R8, R9 and R10 represent hydrogen atoms and Q represents an oxygen atom.

Derivatives of the general formula (III) can be obtained by the alkylation of the hydroxyl function of a suitably protected benzaldehyde or heteroaromatic aldehyde of the general formula of (II), wherein PG represents a protecting group and X, Y and Z are as previously defined. The alkylation can be performed in solvents such as ethers, like tetrahydrofuran, or such as acetonitrile, acetone, methyl-ethyl ketone, N,N-dimethylformamide or dimethylsulfoxide, with R3-X wherein R3 is as previously described and X represents a chloride, bromide, iodide, mesylate or tosylate, in the presence of a base like potassium or sodium carbonate, sodium hydride or potassium tert-butoxide. The alkylation is carried out at temperatures between 0° C. and 100° C. The alkylation can also be carried out by a Mitsunobu reaction using R3-OH, wherein R3 is as defined above, in the presence of triphenylphosphine or tri-octylphosphine and diethyl or diisopropyl, azodicarboxylate or 1,1'(azodicarbonyl)dipiperidine in an aprotic solvent such as, tetrahydrofuran, dichloromethane or toluene, at a temperature between −20° C. and 80° C., for example at room temperature.

Deprotection of the compounds of general formula (III) thus formed is then effected by standard methods, for example by fluoride ions or protic acid if PG is a triisopropylsilyl group, by an aqueous mineral acid such as hydrochloric acid if PG is a tetrahydropyranyl group, by sodium thiophenolate or boron tribromide if PG is a methyl group, or by catalytic hydrogenation Or treatment with boron tribromide if PG is a benzyl group. Deprotection is carried out in a solvent which is inert under the reaction conditions. The aldehyde of formula (IV) is obtained after deprotection.

The aldehyde of formula (IV) is then reacted with a phosphorane or phosphonate (phosphorus ylides). The phosphoranes are formed from phosphonium salts by treatment with a base such as butyllithium, sodium hydride, sodium amide or sodium ethoxide. Wittig or Wadsworth-Emmons-Horner reactions are carried out in a non protic solvent such as tetrahydrofuran or toluene at a temperature of −20° C. to 60° C., for example at room temperature. The resulting α, β-unsaturated ester of the general formula (V) is next reduced by catalytic hydrogenation, such as over palladium at 5-10% on carbon at a pressure of 2-6 bars of hydrogen in an appropriate solvent such as ethanol, until the end of hydrogen consummation.

The resulting hydroxyaryl or heteroaryl propionate of the formula (VI) is then transformed into a trifluoromethane sulfonate (triflate) by standard procedures such as reacting it with trifluoromethane sulfonic anhydride or N-phenyl-bis(trifluoromethanesulfonimide), in the presence of an organic base such as triethylamine, diisopropylethylamine or pyridine in a solvent such as dichloromethane at, a temperature between −5° C. and 25° C.

The triflate of formula (VII) thus obtained is next reacted, in a Suzuki coupling, with an aryl or heteroaryl or cycloalkyl boronic acid or boronic ester of formula (VIII) or (IX), wherein R represents OH or (C1-C6)alkyl groups, where the two R groups may form together an optionally substituted alkylene chain, including pinacolyl, R1 and R2 are as previously defined and FG represents a functional group as defined hereafter. The reaction is carried out in the presence of a typical palladium complex such as tetrakis (triphenylphosphine) palladium, dichlorobis(triphenylphosphine) palladium, and in the presence of a base such as sodium bicarbonate, sodium potassium or cesium carbonate, barium hydroxide, tribasic potassium phosphate or cesium fluoride.

The aryl or heteroaryl boronic acid or ester of formula (VIII) may carry a functional group FG, such as an aldehyde or carboxylic ester, which can be transformed into known derivatives (amines, amides, etc. . . . ) by standard reactions known per se (transformation of compounds of the general formula (X) into derivatives of formula (Xa)), after Suzuki coupling. Otherwise, the boronic acid or ester may already carry its final substituents R1 and R2 (formula (IX)), directly forming compounds of the general formula (Xa).

The palladium-catalyzed Suzuki coupling reaction is carried out in a solvent such as 1,2-dimethoxyethane, ethanol, toluene, N,N-dimethylformamide, NMP, THF, dioxane or N,N-dimethylacetamide or mixtures of two of these, at temperatures ranging from 50° C. to 100° C., preferably at 65-85° C.

The bicyclic esters of general formula (Xa) thus obtained are next transformed into the corresponding acylguanidines of formula (I), object of the present invention, by reacting them directly with guanidine (R11=H) or a substituted guanidine (R11 as previously defined and different from H) of formula (XXXVIII) in the presence of a base in a polar protic solvent, such as sodium ethoxide/ethanol or sodium/2-methoxyethanol at a temperature of 20-100° C., for example at room temperature.

Otherwise, the esters of general formula (Xa) can be saponified into their corresponding carboxylic acid derivative of formula (XI) by lithium, sodium or potassium hydroxide in water and a co-solvent such as tetrahydrofuran or dioxane, or by acid-catalyzed hydrolysis. The carboxylic acid of formula (XI) thus formed is then reacted with the appropriate guanidine or substituted guanidine (XXXVIII) in the presence of a carboxyl-activating coupling agent such as carbonyldiimidazole (CDI), DCC/HOBt, PyBOP, in the presence of a base such as DMAP, DIEA or NMM, in a solvent such as THF, DCM or DMF at room temperature. An acylguanidine of the general formula (I) is also obtained.

The same process as described in scheme 1, using as starting material a compound of formula (II) bearing a R4 group on the aromatic ring as defined in the compounds of formula (I), said R4 group being suitably protected by protecting groups known to one of skill in the art, enables to obtain the compounds according to the invention wherein R4 is different from a hydrogen atom. The same remark applies to schemes 2, 3 and 4 hereafter.

It can be noticed that the steps from compound (VII) to compound (I) can also be used for compounds wherein at least one of R5, R6, R7, R7 is not a hydrogen atom.

Scheme 2

Scheme 2 describes an alternative process for obtaining the compounds of formula (I) according to the invention, wherein R5, R6, R7, R8, R9 and R10 represent hydrogen atoms and Q represents an oxygen atom. According to scheme 2, an aryl or heteroaryl iodo compound is coupled with a boronic acid or boronic ester (Suzuki conditions), or with an organotin compound under Stille conditions.

An aldehyde derivative of the general formula (XII), wherein $PG_1$ represents a protecting group and X, Y and Z are as previously defined, is subjected to a Wittig or Wadsworth-Emmons-Horner reaction with an appropriate phosphorus ylure to obtain the α,β unsaturated ester of the general formula (XIII), in conditions as described in scheme 1. The double bond of these derivatives is next reduced by catalytic hydrogenation and the protecting group is removed, as described in scheme 1.

Then the aryl or heteroaryl-propionate of the general formula (XV) is iodinated by classical agents and conditions known in the art, such as iodine in the presence of base (such as ammonia, KOH, AcONa or $NaCO_3$), or a source of iodide in the presence of an appropriate oxydizing agent, such as sodium or potassium iodide along with chloroamine T or potassium peroxymonosulfate or $H_2O_2$ in methanol, or by iodine monochloride in $CH_2Cl_2$, $CCl_4$ or acetic acid, or N-iodosuccinimide in acetonitrile, at temperatures between 20° C. and 100° C.

The desired iodo derivative of general formula (XVII) is obtained after reaction with R3-X as defined in scheme 1.

Otherwise, the iodo derivative (XVII) can be obtained by reacting the amino derivative of general formula (XVIII) with tert-butyl nitrite and then treating the diazonium derivatives thus formed in situ with a source of iodide, such as diiodomethane.

The iodo derivative of the general formula (XVII) is then coupled to a boronic acid or boronic ester derivative of general formula (VIII) or (IX), as defined in scheme 1, in the presence of a palladium complex as previously described. The iodo derivative of the general formula (XVII) can also be coupled to organotin compounds of the general formula (XIX), where typically Alk is methyl, ethyl or n-butyl and R1, R2 and FG are as described in formula (VIII) and (IX). These organotin compounds of formula (XIX) are either already described in the literature and they are readily prepared by known methods. Such reactions between iodo and organotin derivatives are effected out in the presence of a typical catalyst such as $Pd(PPh_3)_4$, $PdCl_2(PPh_3)_2$, $Pd_2dba_3$ or $PdCl_2[P(o\text{-}tolyl)_3]_2$, with or without addition of copper iodide or lithium chloride, in solvents such as DMF, THF, dioxane, DME or NMP and at temperatures between 40 and 100° C.

The bicyclic propionic ester of general formula (X) thus obtained is transformed into the corresponding acylguanidine of formula (I) by the methods already described in relation with scheme 1. Here again, using as starting material a compound of formula (XII) comprising a R4 group on the aromatic ring as defined in the compounds of formula (I), said R4 group being suitably protected by protecting groups known to one of skill in the art, enables to obtain the compounds according to the invention wherein R4 is different from a hydrogen atom.

Scheme 3

Scheme 3 describes a process for obtaining the compounds of formula (I) according to the invention wherein Q represents a —$CH_2$— link.

The introduction of the group R3-Q-, where Q represents a —$CH_2$— link, is carried out by any carbon-carbon bond forming technique known per se. Useful examples of these are shown in scheme 3 and include, in a first embodiment represented in scheme 3 under item a), Wittig or Wadsworth-Emmons-Horner reactions using intermediates (XX) or (XXI), wherein $PG_1$ and $PG_2$ represent protecting groups, Alk represents (C1-C6)alkyl groups and X, Y and Z are as previously defined. The compound (XXII) is obtained, where R3' represents a (C1-C8)alkyl group optionally substituted as defined in relation to the R3 group comprised in the compounds of the present invention. The compound (XXII) is then reduced and the $PG_2$ groups are removed, leading to the compound of formula (XXIII).

In a second embodiment represented in scheme 3 under item b), aryl or heteroaryl iodides and bromides of general formula (XXIV) are reacted with:

alkynes of formula R3'-C≡C—H or olefins of formula R3'—CH=$CH_2$, wherein R3' represents a (C1-C8)alkyl group optionally substituted as defined in relation to the R3 group comprised in the compounds of the present invention, the coupling reaction being mediated by copper, palladium or zinc and leading to the compound (XXV), which is then reduced and the protecting groups $PG_2$ are removed to obtain the compound (XXIII), or alkyl boronic acid or ester derivatives, organotin derivatives of formula R3—Sn(Alk)$_3$, wherein Alk represents a lower alkyl group, alkyliodides of formula R3—I or organozinc derivatives of formula R3—ZnBr, the coupling reactions being mediated by palladium, copper or manganese and leading to the compound (XXVI), which enables to obtain the compound (XXVII) after deprotection of the PG$_2$ groups.

The compounds of the general formulas (XXIII) and (XXVII) can subsequently be used in the process described in scheme 3 as starting material instead of the compound of formula (III).

Scheme 4

Scheme 4 describes a process for preparing the compounds of formula (I) according to the invention wherein R5 and/or R6 do not represent hydrogen atoms.

Such compounds can be obtained by starting from a ketone of the general formula (XXVIII), wherein PG represents a protecting group, R3 is as defined in scheme 1 and R5 is as previously defined in relation to the compounds of formula (I), and reacting it with a phosphorus ylure, such as a phosphonate in the presence of a base to obtain the trisubstituted acrylate ester derivative of general formula (XXIX). Conjugate 1-4 addition of an organocuprate reagent formed from R6-Li and CuI or other copper salts, in an aprotic solvent such as THF, at a temperature between −78° C. and 60° C., results in a disubstituted compound of the general formula (XXX), which is deprotected to obtain the compounds of formula (XXXI).

The derivative of formula (XXXI) is transformed into its corresponding triflate of the general formula (XXXII), then coupled to an appropriate boronic acid or boronic ester and then transformed into acylguanidine derivatives, as described in scheme 1, to obtain the compound of formula (I) wherein R5 and/or R6 are different from hydrogen atoms.

Scheme 5

Scheme 5 describes a process for preparing the compounds of formula (I) according to the invention wherein R7 and/or R8 do not represent hydrogen atoms.

In a first embodiment described in scheme 4, corresponding to the case where R7=R8, one can alkylate the desired position of the compound of formula (XXXIII) obtained as in scheme 1 with R7-X, wherein R7 is as defined in relation to the compounds of formula (I) and X is a leaving group, in the presence of a base such as sodium ethoxide in ethanol, sodium hydride in DMF or LDA in an ether such as THF, at temperatures between −30° C. and 80° C.

In cases where R7 and R8 as different from each other, or where one wish to introduce only one of R7 or R8 as a substituent different from a hydrogen atom, then a Wittig reaction can carried out on an aldehyde of general formula (II) as described in scheme 1, using an appropriately R7-substituted phosphorane. The resulting substituted olefin of formula (XXXV) is reduced by catalytic hydrogenation yielding the monosubstituted compound of general formula (XXXVI), which can be alkylated at the position alpha to the ester by R8-X, wherein R8 is as defined in relation to the compounds of formula (I) and X is a leaving group, using one of the above-mentioned bases.

The disubstituted ester derivative of formula: (XXXIV) or the monosubstituted ester derivative of formula (XXXVI) is next deprotected, transformed into a triflate, coupled under Suzuki conditions and guanidinylated, in conditions as described in scheme 1, forming an acylguanidine derivative of general formula (I) wherein R7 and/or R8 are different from hydrogen atoms.

Obtention of compounds of formula (I) comprising at least one of R5 and R6 and at least one of R7 and R8 being different from hydrogen atoms can be carried out using sequentially both procedures described in schemes 4 and 5, i.e. by using, as starting material in scheme 5 instead of a compound of formula (XXXIII), a compound of formula (XXXII) as described in scheme 4.

Scheme 5 Bis

Alternatively, ortho-disubstituted esters of formula (XXXIV) can be obtained by a Reformatsky reaction between an aldehyde of formula (IV) and an organozinc reagent prepared by insertion of zinc metal into an α-bromo ester of formula (A) where R7 and R8 are lower alkyls. The resulting β-hydroxyester of formula (B) is then deoxygenated by standard methods, such as triethylsilane/trifluoroacetic acid to provide an ester of the general formula (XXXIV) which is transformed into an acylguanidine derivative of general formula (I) where R7 and R8 both represent lower alkyls using conditions described in scheme I.

Scheme 5 Tris

To obtain a compound of formula (I) where R7 and R8, taken together with the carbon atom to which they are attached, form a (C3-C6) cycloalkyl group, for example a spiro cyclopropyl, a cycloalkanecarboxylic acid 2,6-di-tert-butyl-4-methyl-phenyl ester, prepared according to J. Amer. Chem. Soc. (1985), 107 (19), 539-543, is deprotonated by a strong base, especially tBuLi or LDA and the resulting carbanion is alkylated according to Seebach et al (Helv. Chim. Acta (1986), 69 (7), 1655-65) by a benzyl bromide of formula (C) furnishing an ester of general formula (D) which is transformed by successive, steps described herein except for the hydrolysis of the ester using potassium tert-butoxide in THF/H$_2$O, to a compound of formula (I) where R7 and R8, taken together With the carbon atom to which they are attached, form a (C3-C6) cycloalkyl group.

Scheme 6

Scheme 6 describes a process for preparing the compounds of formula (I) according to the invention wherein R9 and/or R10 are different from hydrogen atoms (i.e. monoacylated, diacylated or monocarbamate and dicarbamate derivatives).

For obtaining monosubstituted derivatives, an acylguanidine of formula I wherein R9 and R10 represent hydrogen atoms is reacted with 1 molar equivalent of the appropriate R9-X reactant, X being a leaving group and R9-X representing an acylhalide, a carboxylic anhydride, or a chloroformiate, in the presence of an organic base such as triethylamine, DIEA, DMAP, NMM or pyridine, in a solvent such as dichloromethane, chloroform, THF or pyridine at a temperature of between −10° C. to room temperature. A compound of the general formula (I) where R10=H and R9 is different from H is obtained.

Alternatively, one can also form a monoacylated derivative of formula (I) by coupling a carboxylic acid of the general formula (XI'), as described in scheme 1, to a previously monoacylated guanidine derivative of formula (XXXVIII').

If one desires a diacylated derivative wherein R9=R10, the same procedure as described above is carried out using an excess (at least 2 molar equivalents) of the reactant R9-X.

For obtaining a diacylated compound of general formula (I) where R9 and R10 are, different from each other, following the first acylation with one molar equivalent of R9-X, a second acylation is carried out, either in situ, or after having isolated the monoacylated compound (where R10=H) and re-submitting it to comparable reaction conditions using a slight excess of R10-X, where R10-X represents an acylhalide, a carboxylic acid anhydride or a chloroformiate. A derivative of the general formula (I) wherein R9≠R10≠H is thus obtained.

Alternatively, for obtaining a compound of formula (I) wherein R9=H and R10≠H, the first step of scheme 5 may be replaced by introduction of a protecting group on the desired position, enabling to introduce thereafter selectively the R10 substituent on the nitrogen atom bearing the R11 group, said protecting group being removed at the end of the reaction by methods known to one of skill.

Finally, terminally substituted acylguanidines may also be obtained by reacting a carboxylic acid of formula (XI') or its potassium or sodium salt, especially where R7 and R8 represent a lower alkyl or where R7 and R8, taken together with the carbon atom to which they are attached, form a (C3-C6) cycloalkyl group, with 1H-pyrazole-1-carboxamide in the presence of a peptide coupling reagent such as 1,1'-carbonyldiimidazole, PyBOP etc, in the presence of a base such as DMAP/TEA in DCM or THF at room temperature. The resulting intermediate of formula (E) is next treated with a large excess of an amine, R11-NH2 in a sealed tube at ordinary temperature in an inert solvent such as DCM or THF to furnish a compound of general formula (I) where R9 and R10=H and R7 and R8=H, lower alkyl of taken together with the carbon atom to which they are attached, form a (C3-C6) cycloalkyl, especially a spiro cyclopropyl.

Scheme 7

Scheme 7 describes a process for preparing the compounds of formula (I) according to the invention wherein R9 and R10 are cyclized together.

A compound of formula (XXXIX), wherein R1, R2, R3, R4, R5, R6, R7, R8, A, K, X, Y and Z are as previously defined in the general formula (I), and wherein Alk represents a methylene or ethylene chain and the group —CO—K represents a amide (for example with K=—NMe$_2$) or an ester group (for example with K=—OMe or —OEt), is cyclized under basic conditions to give the compound of formula (I). Substituents may be present on the methylene or alkylene chain of the starting compound (XXXIX) to give compounds of formula (I) wherein the cyclized guanidine moiety is substituted accordingly.

Scheme 8

Scheme 8 describes a process for preparing the substituted guanidines of the general formula (XXXVIII), wherein R11 is different from a hydrogen atom, used in scheme 1.

The substituted guanidines (XXXVIII) are obtained by known methodology where 1H-pyrazole-1-carboxamidine hydrochloride is reacted with one molar equivalent of R11—NH$_2$ (free base or hydrochloride) in the presence of 1-2 molar equivalents of an organic base such as DIEA or Et$_3$N in a polar solvent such as N,N-dimethylformamide at a concentration of 2 mol/L and at a temperature between 20° C. and 60° C. After evaporation of the solvents and base, the guanidinium hydrochloride is isolated by filtration after treatment with anhydrous 2N HCl in diethyl ether and methanol.

Likewise, N-alkylguanidines may be obtained by reacting a primary amine R$_{11}$-NH$_2$ with aminoiminomethane sulfonic acid in methanol, as described by H. Mosher et al., Tet. Lett. 29, No 26, 3183-3186 (1998).

In schemes 1-8, starting compounds and reactants, unless otherwise indicated, are commercially available or described in literature, or can be prepared according to methods described in literature or known to one of skill in the art.

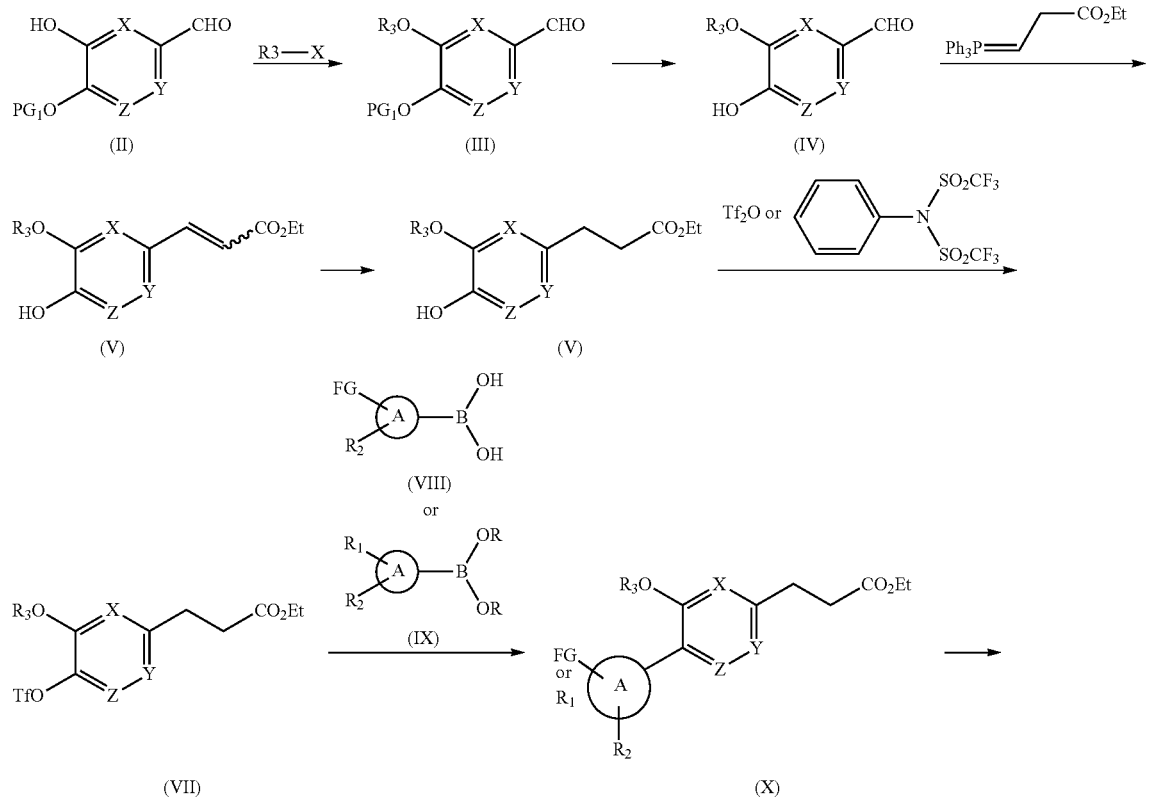

Scheme 1

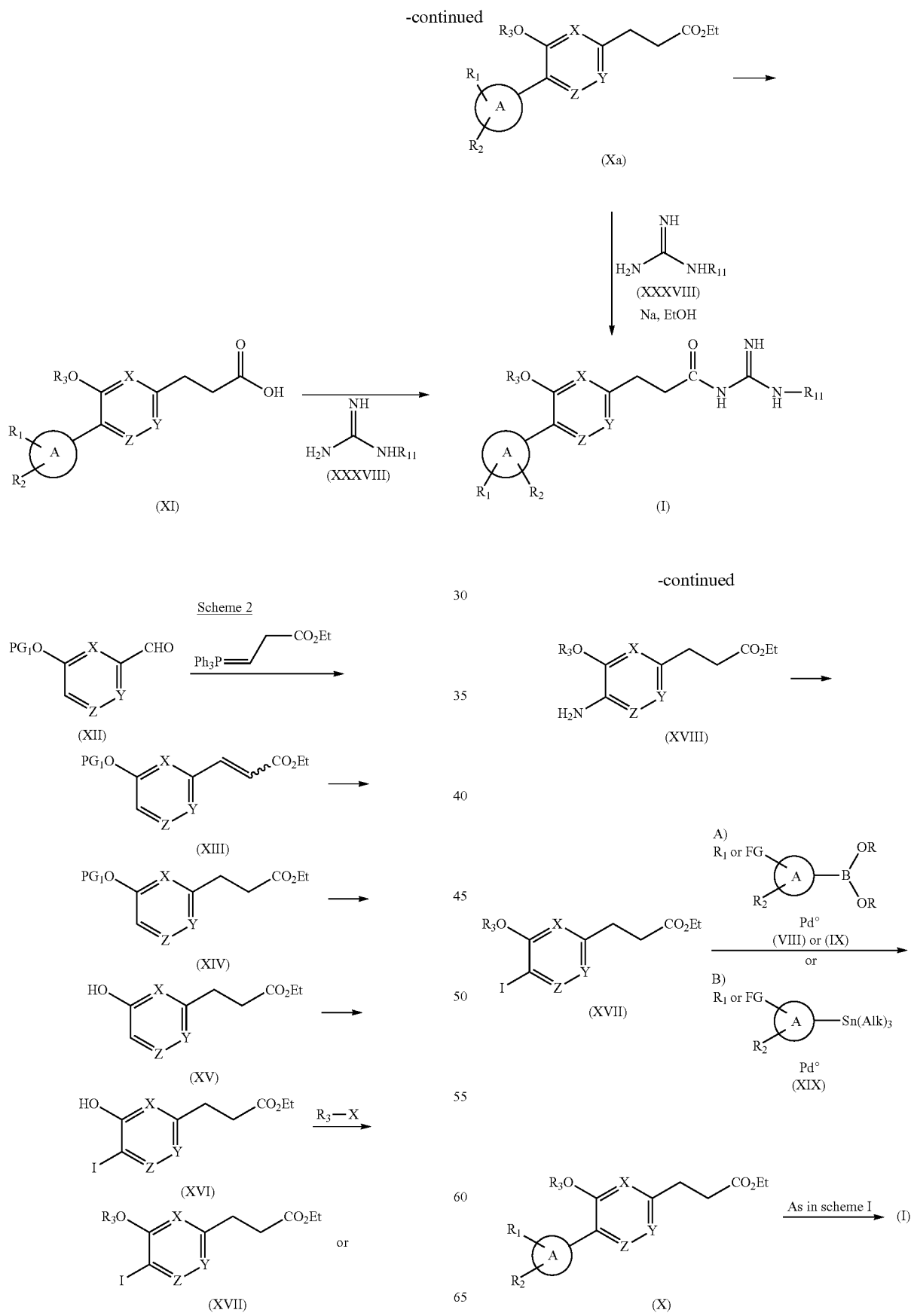

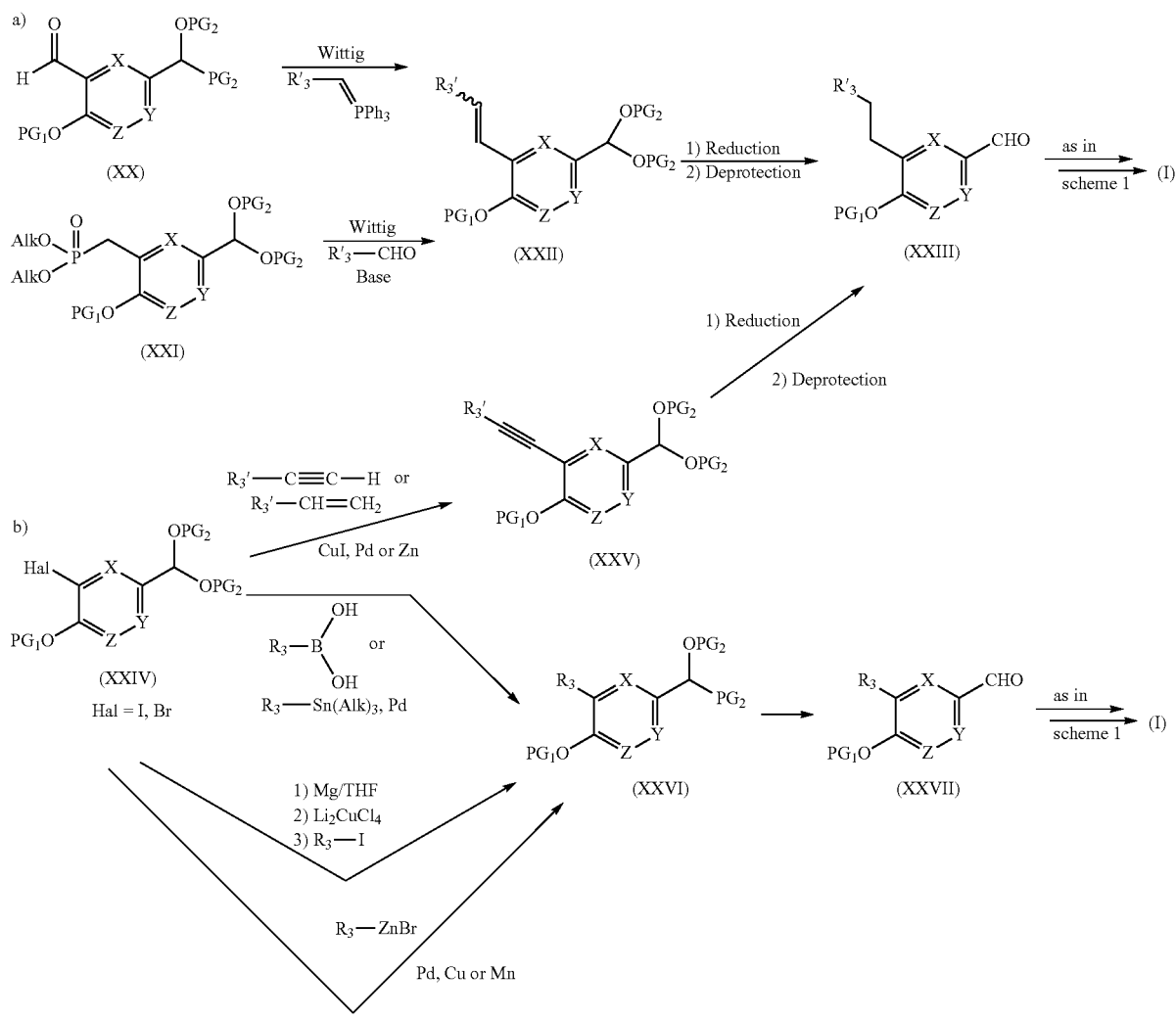
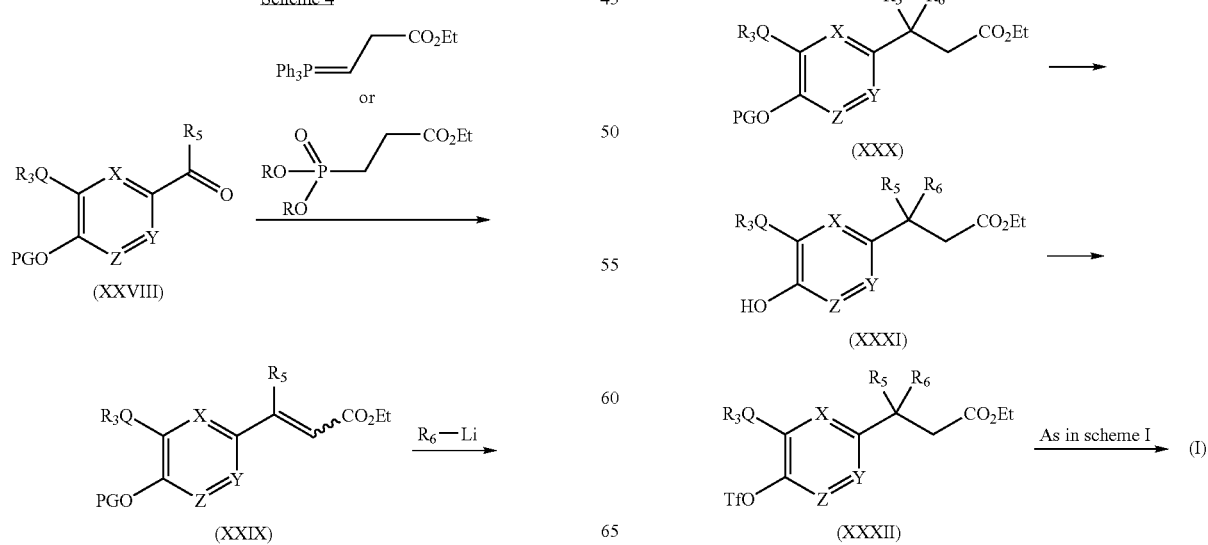

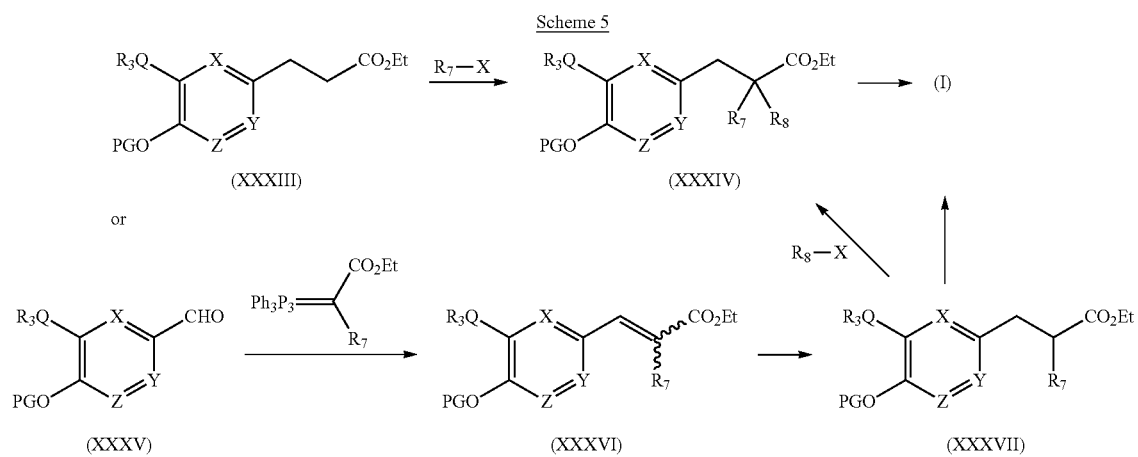
Scheme 5
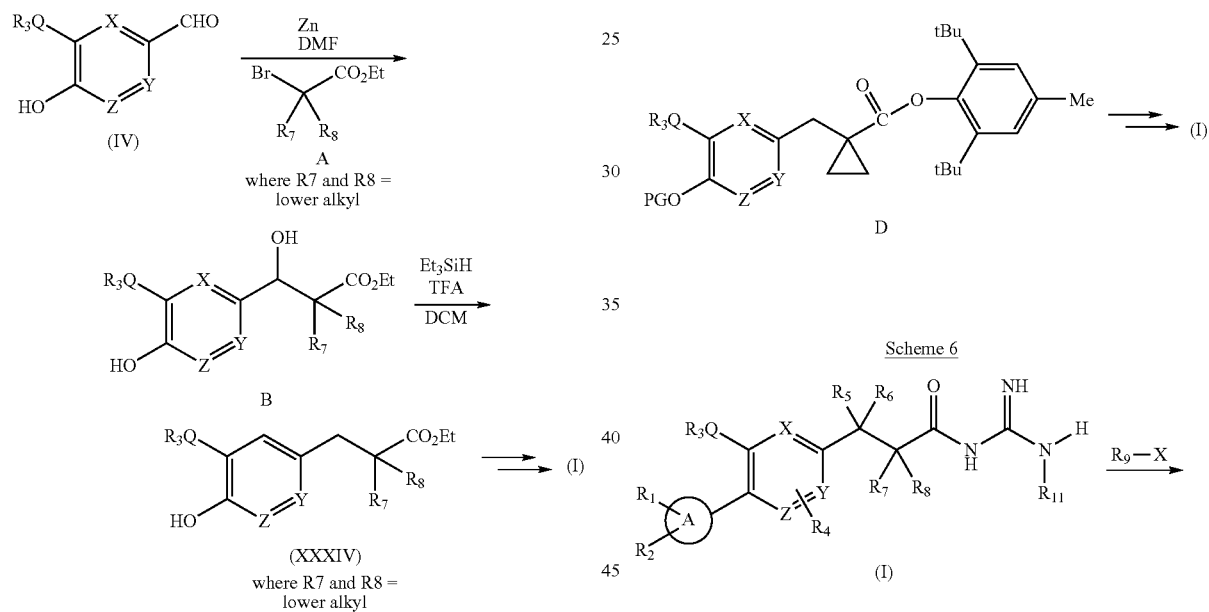
Scheme 5 bis
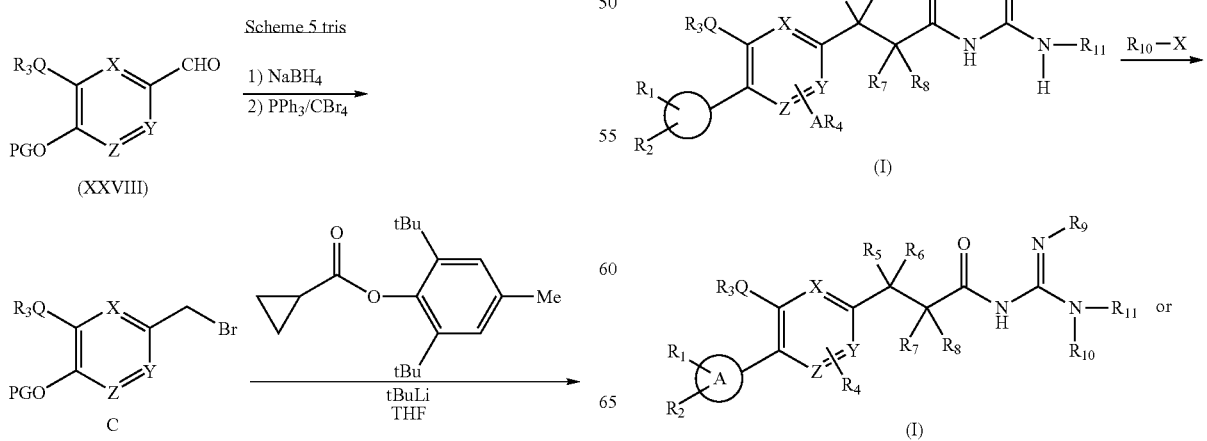
Scheme 6

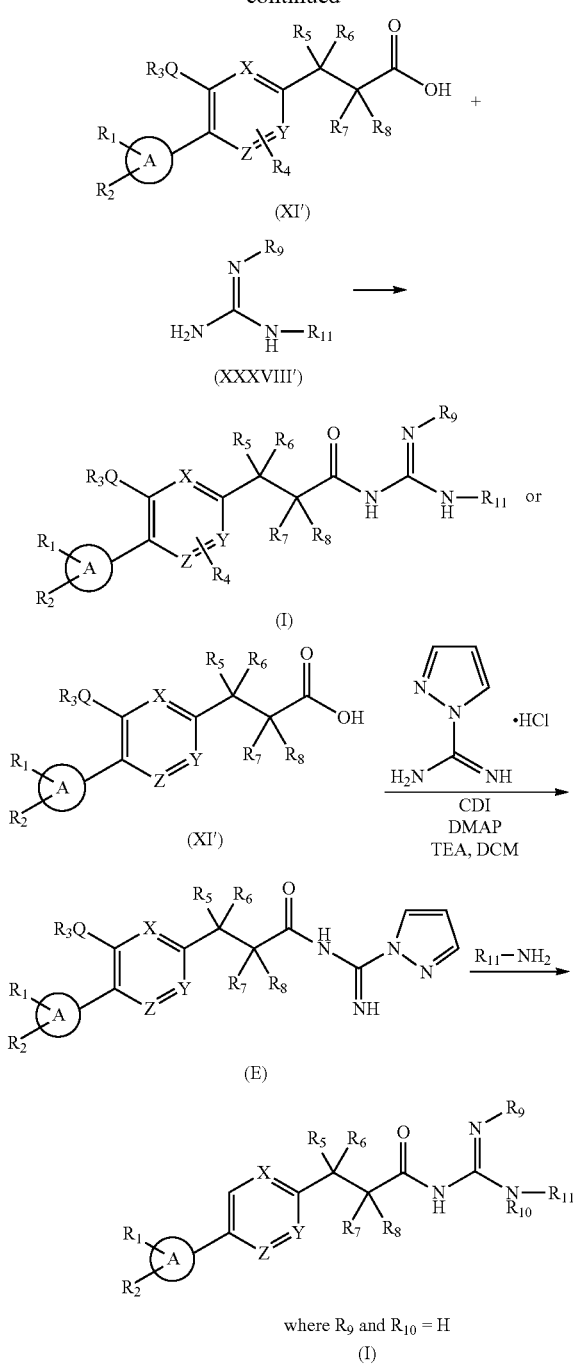

(XI')

(XXXVIII')

(I)

(XI')

(E)

where R9 and R10 = H
(I)

Scheme 7

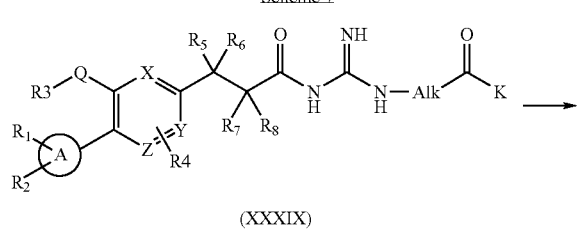

(XXXIX)

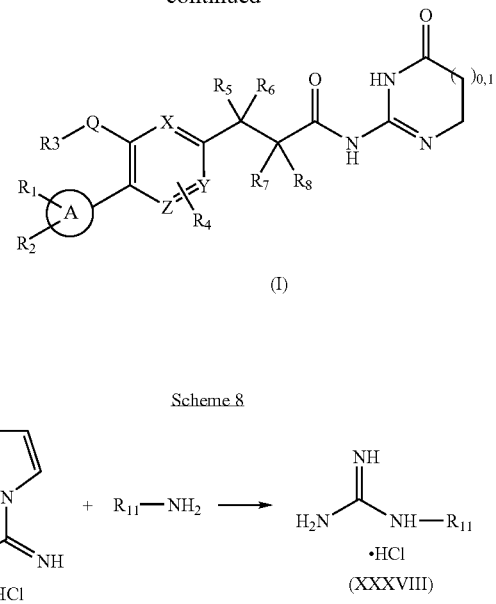

(I)

Scheme 8

A subject of the invention is also the compounds of formula (X), (Xa) and (XI). These compounds are useful as intermediates in the synthesis of the compounds of formula (I).

The following examples describe the synthesis of some compounds according to the invention. These examples are not intended to be limitative and only illustrate the present invention. The numbers of the exemplified compounds refer to those in the tables described hereafter, which illustrate the chemical structures and the physical properties of a number of compounds according to the invention.

The following abbreviations are used:

| | |
|---|---|
| ACN | acetonitrile |
| DMF | dimethylformamide |
| DMSO | dimethyl sulfoxide |
| EDCl | N-ethyl-N'-(3-dimethylaminopropyl)-carbodiimid * HCl |
| FA | formic acid |
| h | hour(s) |
| HCl | hydrochloric acid |
| HOBt | 1-hydroxy benzotriazole |
| HPLC | high performance liquid chromatography |
| LC/MS | liquid chromatography mass spectrometry |
| r.t. | room temperature |
| $R_t$ | retention time |
| THF | tetrahydrofurane |
| TFA | trifluoroacetic acid |

LC/MS spectra were recorded according to the following methods.

Method A: Column: YMC J'shere H80 33×2.1 mm, 4 μm
  Solvent: ACN+0.05% TFA: H$_2$O+0.05% TFA (flow rate=1.3 mL/min)
  Gradient: 5:95, (0 min) to 95:5 (2.5 min) to 95:5 (3.0 min)
  Ionisation: ESI$^+$ Method B: Column: YMC J'shere H80 33×2.1 mm, 4 μm
  Solvent: ACN+0.08% FA: H$_2$O+0.1% FA (flow rate=1.3 mL/min)
  Gradient: 5:95 (0 min) to 95:5 (2.5 min) to 95:5 (3 min)
  Ionisation: ESI$^+$ Method C: Column: YMC J'shere ODS H80 20×2.1 mm, 4 μm
  Solvent: ACN: H$_2$O+0.05% TFA (flow rate=1 mL/min)

Gradient: 4:96 (0 min) to 95:5 (2 min) to 95:5 (2:4 min) to 96:4 (2.45 min)
Ionisation: ESI⁺
Method D: Column: Xterra MS C18 4.6×50 mm, 3 μm (Waters)
Solvent: ACN+0.001% HCO₂H: H₂O+0.001% HCO₂H (flow rate=1 mL/min)
Gradient: 5:95 (0-1 min) to 100:0 (9 min)
Ionisation: ESI⁺
Prep HPLC was performed according to the following method:
Column: Waters Atlantis dC18 OBD 30×100 mm 5 μm
Solvent: ACN: H₂O+0.1% TFA (flow 60 mL/min)
Gradient: 10:90 (0 min) to 90:10 (10 min)

EXAMPLE 1

N-[amino(imino)methyl]-3-[4'-[(4-methylpiperazin-1-yl)methyl]-2-(3-methoxypropoxy)biphenyl-4-yl]propanamide hydrochloride (compound no 1)

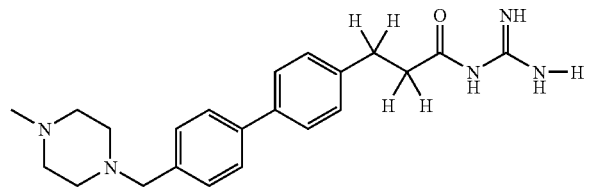

1.1 4-methoxy-3-(3-methoxypropoxy)benzaldehyde 3-hydroxy-4-methoxybenzaldehyde (15 g, 98.6 mmol) was dissolved in acetonitrile (200 mL). 1-Methoxy-3-bromopropane (16.6 g, 108 mmol) and potassium carbonate (34 g, 247 mmol) were added and the mixture was brought to reflux and stirred for 3 hrs. After cooling to room temperature, water and ethyl acetate were added. The aqueous layer was extracted three times with ethyl acetate. The combined organic layers were dried over anhydrous sodium sulfate, filtered and evaporated under reduced pressure to yield 22 g (quantitative yield) of the desired product as a yellow oil, used without further purification.

1.2 4-hydroxy-3-(3-methoxypropoxy)benzaldehyde 4-methoxy-3-(3-methoxypropoxy)benzaldehyde (22 g, 98 mmol) was dissolved in DMF (490 mL) and sodium propanethiolate (12.5 g, 127 mmol) was added. The mixture was brought to 100° C. and the reaction mixture was stirred for 30 minutes. After cooling to room temperature, solvents were evaporated under reduced pressure and the residue was dissolved in dichloromethane (200 mL) and saturated aqueous ammonium chloride (200 mL). Hydrochloric acid 1N was then added until acidic pH. The organic layer was separated and washed with water and brine, dried over anhydrous sodium sulfate, filtered, and evaporated under reduced pressure to yield 20 g (quantitative yield) of the desired product as a yellow oil, used in the next step without further purification.

1.3 Ethyl 3-[4-hydroxy-3-(3-methoxypropoxy)phenyl]acrylate 4-hydroxy-3-(3-methoxypropoxy)benzaldehyde (15 g, 71.3 mmol) was dissolved in tetrahydrofuran (142 mL) and (ethoxycarbonylmethylene)triphenylphosphorane (24.8 g, 71.3 mmol) was added at room temperature portionwise. The mixture was then stirred overnight. The solvents were evaporated under reduced pressure and the residue was purified by flash chromatography on silica gel (cyclohexane/ethyl acetate, 8/2) to yield 16 g (80%) of the desired product as a yellow oil of a mixture of E and Z isomers.

1.4 Ethyl 3-[4-hydroxy-3-(3-methoxypropoxy)phenyl]propanoate

Ethyl 3-[4-hydroxy-3-(3-methoxypropoxy)phenyl]acrylate (16 g, 57 mmol) was dissolved in ethanol (190 mL) in a Parr apparatus. Nitrogen was bubbled for 15 minutes and Pd/C 10% (0.8 g) was added. The reaction mixture was submitted to hydrogenation under H₂ atmosphere (3 bars) until the end of H₂ consumption. The palladium was then filtered and the solvent was evaporated under reduced pressure to yield 12.3 g (76%) of the desired product as a colorless oil.

1.5 Ethyl 3-[3-(3-methoxypropoxy)-4-{[(trifluoromethyl)sulfonyl]oxy}phenyl]propanoate Ethyl 3-[4-hydroxy-3-(3-methoxypropoxy)phenyl]propanoate (12.3 g, 43.5 mmol) was dissolved in dichloromethane (62 mL) under argon. The solution was cooled to 0° C. and triethylamine (18.3 mL, 130 mmol) and N-phenyl-trifluoromethanesulfonimide (18.7 g, 52 mmol) were added. The mixture was stirred for 3 hours and then hydrolyzed with saturated aqueous ammonium chloride. The aqueous layer was extracted three times with dichloromethane. The combined organic layers were washed with brine, dried over anhydrous sodium sulfate, filtered and evaporated under reduced pressure. The residue was purified by flash chromatography on silica gel (cyclohexane/ethyl acetate, 95/5) to yield 13.5 g (74%) of the desired product as a colorless oil.

1.6 Ethyl 3-[4'-formyl-2-(3-methoxypropoxy)biphenyl-4-yl]propanoate

Ethyl 3-[3-(3-methoxypropoxy)-4-{[(trifluoromethyl)sulfonyl]oxy}phenyl]propanoate (5 g, 12 mmol) was dissolved in dimethoxyethane (70 mL) and ethanol (7 mL). 4-Formylbenzeneboronic acid (2.0 g, 13 mmol) was added and argon was bubbled in the mixture, for 15 minutes. Cesium fluoride (4 g, 26 mmol) and tetrakistriphenylphosphine palladium (0.69 g, 0.6 mmol) were added and the mixture was brought to reflux under an argon atmosphere for 4 hours. After cooling to room temperature, solvents were evaporated under reduced pressure and the residue was dissolved in ethyl acetate/water (100 mL/100 mL). The organic layer was washed with saturated aqueous sodium bicarbonate and brine, dried over anhydrous sodium sulfate, filtered and evaporated under reduced pressure. The residue was purified by flash chromatography on silica gel (cyclohexane/ethyl acetate, 9/1) to yield 3.42 g (76%) of the desired product as a yellow oil.

1.7 Ethyl 3-{2-(3-methoxypropoxy)-4'-[(4-methylpiperazin-1-yl)methyl]biphenyl-4-yl}propanoate Ethyl 3-[4'-formyl-2-(3-methoxypropoxy)biphenyl-4-yl]propanoate (1 g, 2.7 mmol) was dissolved in dichloroethane (20 mL). At 0° C., acetic acid (0.02 mL, 0.4 mmol) was added, followed, by N-methylpiperazine (0.3 g, 3 mmol) and sodium triacetoxyborohydride (0.86 g, 4 mmol) portionwise. The mixture was stirred at room temperature overnight. At 0° C., saturated aqueous sodium bicarbonate was added. The aqueous layer was extracted three times with dichloromethane. The combined organic layers were washed with brine and water, dried over anhydrous sodium sulfate, filtered and evaporated under reduced pressure to yield 0.98 g (80%) of the desired product as a brown oil used in the following step without further purification.

1.8 N-[(Amino)(imino)methyl]-3-{2-(3-methoxpropoxy)-4'-[(4-methylpiperazinyl)methyl]biphenyl-4-yl}propanamide Sodium (0.35 g, 15.3 mmol) was dissolved in ethanol (8 mL) at room temperature. Once all the sodium was dissolved, guanidine hydrochloride (1.45 g, 15.3 mmol) was added and the mixture was stirred for 1 h. A white precipitate formed and was filtered off. The filtrate was evaporated under reduced pressure and a solution of ethyl 3-{2-(3-methoxypropoxy)-4'-[(4-methylpiperazin-1-yl)methyl]biphenyl-4-yl}propanoate (1.18 g, 2.4 mmol) and DMF (8 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 9 mL) was added. The mixture was evaporated and the residue was purified on reverse phase ($C_{18}$) flash chromatography ($H_2O$, HCl N/1000, acetonitrile, 100/0 to 80/20) to afford 0.51 g (42%) of the desired product as a white solid: mp=190° C.; $^1$H NMR (400 MHZ, $d_6$-DMSO) δ 12.09 (bs, 1H), 8.35 (bs, 4H), 7.43 (m, 4H), 7.23 (d, 1H), 7.01 (s, 1H), 6.90 (d, 1H), 4.01 (t, 2H), 3.62 (s, 2H), 3.60 (m, 2H), 3.42 (t, 2H), 3.09 (s, 3H), 3.02 (m, 2H), 2.96 (t, 2H), 2.82 (t, 2H), 2.71 (m, 4H), 2.68 (s, 3H), 1.82 (m, 2H).

EXAMPLE 2

N-[amino(imino)methyl]-3-[4'-{[4-(dimethylamino) piperidin-1-yl]methyl}-2-(3-methoxypropoxy)biphenyl-4-yl]propanamide hydrochloride
(Compound no 2)

2.1 Ethyl 3-[4'-{[4-(dimethylamino)piperidin-1-yl] methyl}-2-(3-methoxypropoxy)biphenyl-4-yl]propanoate Ethyl 3-[4'-formyl-2-(3-methoxypropoxy)biphenyl-4-yl] propanoate (1 g, 2.7 mmol) was dissolved in dichloroethane (20 mL). At 0° C., acetic acid (0.02 mL, 0.4 mmol) was added, followed by N,N-dimethylpiperidine (0.4 g, 3 mmol) and sodium triacetoxyborohydride (0.86 g, 4 mmol) portionwise. The mixture was stirred at room temperature overnight. At 0° C., saturated aqueous sodium bicarbonate was added. The aqueous layer was extracted three times with dichloromethane. The combined organic layers were washed with brine and water, dried over anhydrous sodium sulfate, filtered and evaporated under reduced pressure to yield 1.18 g (90%) of the desired product as a brown oil used in the following step without further purification.

2.2 N-[amino(imino)methyl]-3-[4'-{[4-(dimethylamino)piperidin-1-yl]methyl}-2-(3-methoxy propoxy)biphenyl-4-yl]propanamide hydrochloride Sodium (0.35 g, 15.3 mmol) was dissolved in ethanol (8 mL) at room temperature. Once all the sodium was dissolved, guanidine hydrochloride (1.45 g, 15.3 mmol) was added and the mixture was stirred for 1 h. A white precipitate formed and was filtered off. The filtrate was evaporated under reduced pressure and a solution of ethyl 3-[4'-{[4-(dimethylamino) piperidin-1-yl]methyl}-2-(3-methoxy-propoxy)biphenyl-4-yl]propanoate (1.18 g, 2.4 mmol) and DMF (8 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 9 mL) was added. The mixture was evaporated and the residue was purified on reverse phase ($C_{18}$) flash chromatography ($H_2O$, HCl N/1000, acetonitrile, 100/0 to 80/20) to afford 0.51 g (42%) of the desired product as a white solid: mp=220° C.; $^1$H NMR (400 MHZ, $d_6$-DMSO) δ 8.38 (bs, 4H), 7.52 (m, 4H), 7.25 (d, 1H), 7.02 (s, 1H), 6.89 (d, 1H), 4.29 (s, 2H), 4.08 (t, 2H), 3.56 (m, 4H), 3.40 (t, 2H), 3.20 (s, 3H), 2.90 (t, 2H), 2.80 (t, 2H), 2.71 (s, 3H), 2.70 (s, 3H), 2.21 (m, 4H), 1.80 (m, 2H).

EXAMPLE 3

N-[(butylamino)(imino)methyl]-3-{2-(3-methoxypropoxy)-4'-[(4-methylpiperazin-1-yl)methyl]biphenyl-4-yl}propanamide hydrochloride
(Compound no 3)

3.1 1-butylguanidine hydrochloride

Pyrazole-1-carboxamidine hydrochloride (25 g, 170 mmol) was dissolved in DMF (85 mL) at room temperature. Butylamine (12.5 g, 170 mmol) was added, followed by diisopropylethylamine (30 mL, 170 mmol). The mixture was stirred at room temperature for 18 hrs. The solvents were evaporated under reduced pressure and the residue was dissolved in methanol (85 mL) and HCl in diethyl ether (2N, 84 mL) was added to form the hydrochloride salt. Diethyl ether was added and the precipitate was filtered to yield 25 g of 1-butylguanidine hydrochloride as a white solid.

3.2 N-[(Butylamino)(imino)methyl]-3-{2-(3-methoxypropoxy)-4'-[(4-methylpiperazin-1-yl)methyl] biphenyl-4-yl}propanamide hydrochloride Sodium (0.31 g, 13.5 mmol) was dissolved in ethanol (7 mL) at room temperature. Once all the sodium was dissolved, 1-butylguanidine hydrochloride (2.05 g, 13.5 mmol) was added and the mixture was stirred for 1 h. A white precipitate formed and was filtered off. The filtrate was evaporated under reduced pressure and a solution of ethyl 3-{2-(3-methoxypropoxy)-4'-[(4-methylpiperazin-1-yl)methyl]biphenyl-4-yl}propanoate (0.98 g, 2.2 mmol) and DMF (7 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 8 mL) was added. The mixture was evaporated and the residue was purified on reverse phase ($C_{18}$) flash chromatography ($H_2O$, HCl N/1000, acetonitrile, 100/0 to 80/20) to afford 0.60 g (53%) of the desired product as a white solid: mp=125° C.; $^1$H NMR (400 MHZ, $d_6$-DMSO) δ 9.05 (bs, 1H), 8.70 (bs, 2H), 7.55 (en, 4H), 7.25 (d, 1H), 7.08. (s, 1H), 7.90 (d, 1H), 4.30 (s, 2H), 4.04 (t, 2H), 3.36 (m, 10H), 3.21 (t, 2H), 3.19(s, 3H), 2.86 (m, 4H), 2.81 (s, 3H), 1.97 (m, 2H), 1.45 (m, 2H), 1.30 (m, 2H), 0.85 (t, 3H).

EXAMPLE 4

N-{[(2-cyclopropylethyl)amino](imino)methyl}-3-[4'-{[4-(dimethylamino)piperidin-1-yl]methyl}-2-(3-methoxypropoxy)biphenyl-4-yl]propanamide hydrochloride (Compound no 9)

Sodium (0.15 g, 6.5 mmol), was dissolved in ethanol (3.5 mL) at room temperature. Once all the sodium was dissolved, 1'-(2-cyclopropylethyl)guanidine hydrochloride (0.87 g, 6.5 mmol) was added and the mixture Was stirred for 1 h. A white precipitate formed and was filtered off. The filtrate was evaporated under reduced pressure and a solution of ethyl 3-[4'-{[4-(dimethylamino)piperidin-1-yl]methyl}-2-(3-methoxypropoxy)biphenyl-4-yl]propanoate (0.50 g, 1.0 mmol) and DMF (3.5 mL) was added at room temperature. After completion of the reaction, the mixture was poured into dichloromethane/brine (50/50). The aqueous layer was extracted three times with dichloromethane. The combined organic: layers were washed with brine, dried over anhydrous sodium sulfate, filtered and evaporated under reduced pressure. The residue was then dissolved in ethanol and HCl in diethyl ether (1N, 4 mL) was added. The mixture was evaporated and the residue was purified on reverse phase ($C_{18}$) flash chromatography ($H_2O$, HCl N/1000, acetonitrile, 100/0 to 80/20) to afford 0.20 g (35%) of the desired product as a white solid: mp=248° C.; $^1$H NMR (400 MHZ, $d_6$-DMSO) δ 12.28 (bs, 1H), 11.11 (bs, 1H), 9.10 (t, 1H), 8.79 (bs, 1H), 7.60 (m, 4H), 7.22 (d, 1H), 7.06 (s, 1H), 6.90 (d, 1H), 4.29 (s, 2H), 4.08 (t, 2H), 3.39 (m, 9H), 3.21 (s, 3H), 2.9 (t, 2H), 2.98 (t, 2H), 2.71 (s, 3H), 2.70 (s, 3H), 2.21 (m, 4H), 1.89 (m, 2H) 1.41 (q, 2H), 0.71 (m, 1H), 0.40 (m 2H). 0.14 (m, 2H).

EXAMPLE 5

N-[amino(imino)methyl]-3-[2-(3-methoxypropoxy)-4'-(piperidin-1-ylmethyl)biphenyl-4-yl]propanamide hydrochloride (Compound no 13)

5.1 Ethyl 3-[2-(3-methoxypropoxy)-4'-(piperidin-1-ylmethyl)biphenyl-4-yl]propanoate Ethyl 3-[4'-formyl-2-(3-methoxypropoxy)biphenyl yl]propanoate (1 g, 2.7 mmol) was dissolved in dichloroethane (20 mL). At 0° C., acetic acid (0.02 mL, 0.4 mmol) was added, followed by piperidine (0.25 g, 3 mmol) and sodium triacetoxyborohydride (0.86 g, 4 mmol) portionwise. The mixture was stirred at room temperature overnight. At, 0° C., saturated aqueous sodium bicarbonate solution was added. The aqueous layer was extracted three times with dichloromethane. The combined organic layers were washed with brine and water, dried over anhydrous sodium sulfate, filtered and evaporated under reduced pressure to yield 0.95 g (80%) of the desired product as a brown oil.

5.2 N-[amino(imino)methyl]-3-[2-(3-methoxypropoxy)-4'-(piperidin-1-ylmethyl)biphenyl-4-yl]propanamide hydrochloride Sodium (0.15 g, 6.4 mmol), was dissolved in ethanol (3.5 mL) at room temperature. Once all the sodium was dissolved, guanidine hydrochloride (0.61 g, 6.4 mmol) was added and the mixture was stirred for 1 h. A white precipitate formed and was filtered off. The filtrate was evaporated under reduced pressure and a solution of ethyl 3-[2-(3-methoxypropoxy)-4'-(piperidin-1-ylmethyl)biphenyl-4-yl]propanoate (0.45 g, 1.0 mmol) and DMF (3.5 mL) was added at room temperature. After completion of the reaction, the mixture was poured into: dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 2 mL) was added. The mixture was evaporated and the residue was purified on reverse phase ($C_{18}$) flash chromatography ($H_2O$, HCl N/1000, acetonitrile, 100/0 to 80/20) to afford 0.23 g (43%) of the desired product as a white solid: mp=70° C.; $^1$H NMR (400 MHZ, $d_6$-DMSO) δ 12.04 (bs, 1H), 10.12 (bs, 1H), 8.31 (bs, 2H), 7.56 (s, 4H), 7.22 (d, 1H), 7.00 (s, 1H), 6.91 (d, 1H), 4.22 (s, 2H), 4.01 (t. 2H), 3.35 (m, 6H), 3.21 (s, 3H), 2.93 (t, 2H), 2.87 (t, 2H), 1.90 (m, 2H), 1.76 (m, 6H).

EXAMPLE 6

3-{4'-[(4-Acetylpiperazin-1-yl)methyl]-2-(3-methoxypropoxy)biphenyl-4-yl}-N-[amino(imino)methyl] propanamide hydrochloride (Compound no 14)

6.1 Ethyl 3-{4'-[(4-acetylpiperazin-1-yl)methyl]-2-(3-methoxypropoxy)biphenyl-4-yl}propanoate Ethyl 3-[4'-formyl-2-(3-methoxypropoxy)biphenyl-4-yl]propanoate (1 g, 2.7 mmol) was dissolved in dichloroethane (20 mL). At 0° C., acetic acid (0.02 mL, 0.4 mmol) was added, followed by N-acetylpiperazine (0.38 g, 3 mmol) and sodium triacetoxyborohydride (0.86 g, 4 mmol) portionwise. The mixture was stirred at room temperature overnight. At 0° C., saturated aqueous sodium bicarbonate was added. The aqueous layer was extracted three times with dichloromethane. The combined organic layers were washed with brine and water, dried over anhydrous sodium sulfate, filtered and evaporated under reduced pressure to yield 1.02 g (78%) of the desired product as a brown oil.

6.2 3-{4'-[(4-acetylpiperazin-1-yl)methyl]-2-(3-methoxypropoxy)biphenyl-4-yl}-N-[amino(imino) methyl]propanamide hydrochloride Sodium (0.14 g, 6.0 mmol) was dissolved in ethanol (3.5 mL) at room temperature. Once all the sodium was dissolved, guanidine hydrochloride (0.57 g, 6.0 mmol) was added and the mixture was stirred for 1 h. A white precipitate formed and was filtered off. The filtrate was evaporated under reduced pressure and absolution of ethyl 3-{4'-[(4-acetylpiperazin-1-yl)methyl]-2-(3-methoxypropoxy)biphenyl-4-yl}propanoate (0.46 g, 0.9 mmol) and DMF (3.5 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 2 mL) was added. The mixture was evaporated and the residue was purified on reverse phase ($C_{18}$) flash chromatography ($H_2O$, HCl N/1000, acetonitrile, 100/0 to 80/20) to afford 0.17 g (32%) of the desired product as a white solid: mp=138° C.; $^1$H NMR (400 MHZ, $d_6$-DMSO) δ 12.10 (bs, 1H), 11.27 (bs, 1H), 8.31 (bs, 2H), 7.51 (m, 4H), 7.25 (d, 1H), 7.02 (s, 1H), 6.89 (d, 1H), 4.32 (m, 2H), 4.03 (t, 2H), 3.41 (m, 8H), 3.38 (t, 2H), 3.20 (s, 3H), 2.87 (m, 4H), 2.08 (s, 3H), 1.88 (m, 2H).

EXAMPLE 7

N-[amino(imino)methyl]-3-{2-(3-methoxypropoxy)-4'-[(4-methylpiperazin-1-yl)carbonyl]biphenyl-4-yl}propanamide hydrochloride (Compound no 17)

7.1 4'-(3-Ethoxy-3-oxopropyl)-2'-(3-methoxypropoxy)biphenyl-4-carboxylic acid 3-[4'-Formyl-2-(3-methoxpropoxy)biphenyl-4-yl]propanoate (0.5 g, 1.3 mmol) was dissolved in acetone (22 mL) and a solution of potassium permanganate (0.75 g, 4.7 mmol) and water (11 mL) was added at room temperature; the mixture was stirred for 18 hrs and then filtered. Dichloromethane was added and the mixture was then acidified at 0° C. with HCl 1N. The aqueous layer was extracted three times with dichloromethane and the combined organic layers were washed twice with water, dried over anhydrous sodium sulfate, filtered and evaporated under reduced pressure to yield 0.48 g (929) of the desired product as a brown solid: mp=86° C.

7.2 Ethyl 3-{2-(3-methoxypropoxy)-4'-[(4-methylpiperazin-1-yl)carbonyl]biphenyl-4-yl}propanoate In a round bottom flask, under an atmosphere of argon, 4'-(3-ethoxy-3-oxopropyl)-2'-(3-methoxypropoxy)biphenyl-4-carboxylic acid (0.48 g, 1.2 mmol) was dissolved in dichloromethane (20 mL). EDCl (0.29 g, 1.5 mmol), HOBT (0.20 g, 1.5 mmol) and diisopropylethylamine (1.08 mL, 6.2 mmol) were added at room temperature. After consumption of all the acid, N-methylpiperazine (0.11 mL, 1.0 mmol) was added and the mixture, was stirred for 18 hrs. The organic layer was washed twice with water. The combined organic layers were dried over anhydrous sodium sulfate, filtered and evaporated under reduced pressure. The residue was purified by flash chromatography on silica gel (dichloromethane/ethanol, 90/10) to yield 0.36 g (62%) of the desired product as a yellow oil.

7.3 N-[amino(imino)methyl]-3-{2-(3-methoxypropoxy)-4'-[(4-methylpiperazin-1-yl)carbonyl]biphenyl-4-yl}propanamide hydrochloride Sodium (0.11 g, 4.8 mmol) was dissolved in ethanol (2.5 mL) at room temperature. Once all the sodium was dissolved, guanidine hydrochloride (0.46 g, 4.8 mmol) was added and the mixture was stirred for 1 h. A white precipitate formed and was, filtered off. The filtrate was evaporated under reduced pressure and a solution of ethyl 3-{2-(3-methoxypropoxy)-4'-[(4-methylpiperazin-1-yl)carbonyl]biphenyl-4-yl}propanoate (0.36 g, 0.8 mmol) and DMF (2.5 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 4 mL) was added. The mixture was evaporated and the residue was purified on reverse phase ($C_{18}$) flash chromatography ($H_2O$, HCl N/1000, acetonitrile, 100/0 to 80/20) to afford 0.19 g (45%) of the desired product as a white solid: mp=122° C.; $^1$H NMR (400 MHZ, $d_6$-DMSO) δ 12.13 (bs, 1H), 11.15 (bs, 1H), 8.29 (bs, 2H), 7.52 (m, 4H), 7.25 (d, 1H), 7.02 (s, 1H), 6.92 (d, 1H), 4.00 (t, 2H), 3.31 (t, 2H), 3.30 (m, 4H), 3.20 (s, 3H), 2.89 (m, 8H) 2.72 (s, 3H), 1.84 (m, 2H).

EXAMPLE 8

N-[imino(propylamino)methyl]-3-{2-(3-methoxypropoxy)-4'-[(4-methylpiperazin-1-yl)carbonyl]biphenyl-4-yl}-3-methylbutanamide hydrochloride (Compound no 25)

8.1 3-(3-methoxypropoxy)-4-[(triisopropylsilyl)oxy]benzaldehyde

In a round bottom flask, 4-hydroxy-3-(3-methoxypropoxy)benzaldehyde (10 g, 47.6 mmol) was introduced. DMF (69 mL) was added. The solution was cooled to 0° C. and imidazole (8.09 g, 118.9 mmol), followed by triisopropylsilyl chloride (10.7 mL, 49.9 mmol) were added. The mixture was stirred for 2 hrs and the solvent was evaporated. A saturated aqueous ammonium chloride was added and the aqueous layer was extracted with ethyl acetate. The organic layer was washed with brine, dried over anhydrous sodium sulfate, filtered and evaporated under reduced pressure. The residue was purified by flash chromatography on silica gel (cyclohexane/ethyl acetate, 9/1) to yield 12 g (69%) of the desired product as a yellow oil.

8.2 1-{3-(3-methoxypropoxy)-4-[(triisopropylsilyl)oxy]phenyl}ethanol 3-(3-methoxypropoxy)-4-[(triisopropylsilyl)oxy]benzaldehyde (12 g, 32.7 mmol) was dissolved in tetrahydrofuran (300 mL) and the solution was cooled to 0° C. Methyl magnesium chloride (109 mL, 327 mmol) was added dropwise. The temperature was then allowed to rise to room temperature and the mixture was stirred an hour. At 0° C., saturated aqueous ammonium chloride was added to hydrolyze the reaction mixture. The aqueous layer was extracted twice with ethyl acetate. The combined organic layers were washed with brine, dried over anhydrous sodium sulfate, filtered and evaporated under reduced pressure to yield 12.5 g (quantitative yield) of the desired product as a yellow oil.

8.3 1-{3-(3-methoxypropoxy)-4-[(triisopropylsilyl)oxy]phenyl}ethanone

1-{3-(3-methoxypropoxy)-4-[(triisopropylsilyl)oxy]phenyl}ethanol (12.5 g, 32.7 mmol) was dissolved in toluene (1200 mL) and manganese dioxide (74.7 g, 860 mmol) was added. The mixture was brought to reflux for 7 hrs. The mixture was then filtered off and the solvent was evaporated to yield 9.8 g (quantitative yield) of the desired product as an oil.

8.4 Ethyl 3-{3-(3-methoxypropoxy)-4-[(triisopropylsilyl)oxy]phenyl}but-2-enoate In a three-necked round bottom flask, sodium hydride 60% (1.04 g, 26.0 mmol) was suspended in dimethoxyethane (15 mL) at 0° C. Ethyl[bis(2,2,2-trifluoroethoxy)phosphinyl]acetate (8.63 g, 26.0 mmol) was added and the mixture was stirred at room temperature for 15 minutes. A solution of 1-{3-(3-methoxypropoxy)-4-[(triisopropylsilyl)oxy]phenyl}ethanone (6.60 g, 17.3 mmol) and dimethoxyethane (20 mL) was added and the mixture was brought to reflux and stirred for 1 hr. The reaction mixture was hydrolyzed with saturated aqueous ammonium chloride (80 mL). The aqueous layer was extracted with ethyl acetate (3×100 mL). The combined organic layers were washed with brine, dried over anhydrous sodium sulfate, filtered and evaporated under reduced pressure. The residue was purified by flash chromatography on silica gel (cyclohexane/ethyl acetate, 8/2) to yield 7.5 g (81%) of the desired product as a colorless oil of a mixture of E and Z isomers.

8.5 Ethyl 3-{3-(3-methoxypropoxy)-4-[(triisopropylsilyl)oxy]phenyl}-3-methylbutanoate At 0° C., copper (I) iodide (4.11 g, 21.6 mmol) was dissolved in diethyl ether (10 mL). Methyllithium (1.6N, 27 mL) was added and the mixture was stirred for 10 minutes. The solvent was removed under reduced pressure and cold dichloromethane (10 mL) was added. The solvent was removed under reduced pressure. Cold dichloroethane (83 mL) was added and the mixture was cooled to −78° C. Trimethylsilyl chloride (2.73 mL, 21.6 mmol) was added, followed by a solution of ethyl 3-{3-(3-methoxypropoxy)-4-[(triisopropylsilyl)oxy]phenyl}but-2-enoate (2.43 g, 5.4 mmol) and dichloroethane (10 mL). The temperature was maintained at 0° C. for 3 hrs and the mixture was then hydrolyzed with saturated aqueous ammonium chloride. The aqueous layer was extracted with dichloromethane. The combined organic layers were washed with brine, dried over anhydrous sodium sulfate, filtered, and evaporated under reduced pressure. The residue was purified by flash chromatography on silica gel (cyclohexane/ethyl acetate, 95/5) to yield 2.6 g (84%) of the desired product as an oil.

8.6 Ethyl 3-[4-hydroxy-3-(3-methoxypropoxy)phenyl]-3-methylbutanoate

In a round bottom flask, was introduced ethyl 3-{3-(3-methoxypropoxy)-4-[(triisopropylsilyl)oxy]phenyl}-3-methylbutanoate (2.60 g, 5.6 mmol) and tetrahydrofuran (18 mL). The mixture was cooled to 0° C. and tetrabutylammonium fluoride (1N in THF, 8.4 mL) was added. The solution was stirred for 2 hrs and hydrolyzed with saturated aqueous ammonium chloride. The aqueous layer was extracted with ethyl acetate. The combined organic layers were washed with brine, dried over anhydrous sodium sulfate, and evaporated under reduced pressure. The residue was purified by flash chromatography on silica gel (cyclohexane/ethyl acetate, 8/2) to yield 1.7 g (99%) of the desired product as a yellow oil.

8.7 Ethyl 3-[3-(3-methoxypropoxy)-4-{[(trifluoromethyl)sulfonyl]oxy}phenyl]-3-methylbutanoate Ethyl 3-[4-hydroxy-3-(3-methoxypropoxy)phenyl]-3-methylbutanoate (1.7 g, 5.5 mmol) was dissolved in dichloromethane (8 mL) under argon. The solution was cooled to 0° C. and triethylamine (2.3 mL, 16.6 mmol) and N-phenyltrifluoromethanesulfonimide (2.4 g, 6.6 mmol) were added. The mixture was stirred for 3 hours and then hydrolyzed with saturated aqueous ammonium chloride. The aqueous layer was extracted three times with dichloromethane. The combined organic layers were washed with brine, dried over anhydrous sodium sulfate, filtered and evaporated under reduced pressure. The residue was purified by flash chromatography on silica gel (cyclohexane/ethyl acetate, 95/5) to yield 2.4 g (100%) of the desired product as a colorless oil.

8.8 Ethyl 3-[4'-formyl-2-(3-methoxypropoxy)biphenyl-4-yl]-3-methylbutanoate

Ethyl 3-[3-(3-methoxypropoxy)-4-{[(trifluoromethyl)sulfohyl]oxy}phenyl]-3-methylbutanoate (2.18 g, 4.9 mmol) was dissolved in dimethoxyethane (28 mL) and ethanol (2.8 mL). 4-Formylbenzeneboronic acid (0.81 g, 5.4 mmol) was added and argon was bubbled in the mixture for 15 minutes. Cesium fluoride (1.6 g, 10.8 mmol) and tetrakistriphenylphosphine palladium (0.28 g, 0.2 mmol) were added and the mixture was brought to reflux under an argon atmosphere for 4 hours. After cooling to room temperature, solvents were evaporated under reduced pressure and the residue was dissolved in ethyl acetate/water (50 mL/50 mL). The organic layer was washed with saturated aqueous sodium bicarbonate and brine, dried over anhydrous sodium sulfate, filtered and evaporated under reduced pressure. The residue was purified by flash chromatography on silica gel (cyclohexane/ethyl acetate, 9/1) to yield 1.66 g (78%) of the desired product as a yellow oil.

8.9 4'-(3-Ethoxy-1,1-dimethyl-3-oxopropyl)-2'-(3-methoxypropoxy)biphenyl-4-carboxylic acid Ethyl 3-[4'-formyl-2-(3-methoxypropoxy)biphenyl-4-yl]-3-methylbutanoate (1.0 g, 2.5 mmol) was dissolved in acetone (40 mL) and a solution of potassium permanganate (1.4 g, 8.8 mmol) and water (20 mL) was added at room temperature. The mixture was stirred for 18 hrs and then filtered. Dichloromethane was added and the mixture was then acidified at 0° C. with HCl 1N. The aqueous layer was extracted three times with dichloromethane and the combined organic layers were washed twice with water, dried over anhydrous sodium sulfate, filtered and evaporated under reduced pressure to yield 1.0 g, (96%) of the desired product as a brown solid.

8.10 Ethyl 3-{2-(3-methoxypropoxy)-4'-[(4-methylpiperazin-1-yl)carbonyl]biphenyl-4-yl}-3-methylbutanoate In a round bottom flask, under an atmosphere of argon, 4'-(3-ethoxy-1,1-dimethyl-3-oxopropyl)-2'-(3-methoxypropoxy)biphenyl-4-carboxylic acid (1.0 g, 2.4 mmol) was dissolved in dichloromethane (40 mL). EDCl (0.55 g, 2.9 mmol), HOBT (0.39 g, 2.9 mmol) and diisopropylethylamine (2.10 mL, 12.1 mmol) were added at room temperature. After consumption of all the acid, N-methylpiperazine (0.27 mL, 2.4 mmol) was added and the mixture was stirred for 18 hrs. The organic layer was washed twice with water. The combined organic layers were dried over anhydrous sodium sulfate, filtered and evaporated under reduced pressure. The residue was purified by flash chromatography on silica gel (dichloromethane/ethanol, 95/5) to yield 0.51 g (43%) of the desired product as a yellow oil.

8.11 N-[imino(propylamino)methyl]-3-{2-(3-methoxypropoxy)-4'-[(4-methylpiperazin-1-yl)carbonyl]biphenyl-4-yl}-3-methylbutanamide hydrochloride Sodium (0.15 g, 6.5 mmol) was dissolved in ethanol (3.5 mL) at room temperature. Once all the sodium was dissolved, propylguanidine hydrochloride (0.65 g, 6.5 mmol) was added and the mixture was stirred for 1 h. A white precipitate formed and was filtered off. The filtrate was evaporated under reduced pressure and a solution of ethyl 3-{2-(3-methoxypropoxy)-4'-[(4-methylpiperazin-1-yl)carbonyl]biphenyl-4-yl}-3-methylbutanoate (0.51 g, 1.0 mmol) and DMF (3.5 mL) was added at room temperature. The mixture was stirred at 50° C. until reaction was completed. The mixture was then poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 4 mL) was added. The mixture was evaporated and the residue was purified on reverse phase ($C_{18}$) flash chromatography ($H_2O$, HCl N/1000, acetonitrile, 100/0 to 80/20) to afford 0.20 g (35%) of the desired product as a white solid: mp=99° C.; $^1$H NMR (400 MHZ, $d_6$-DMSO) δ 12.22 (bs, 1H), 11.15 (bs, 1H), 9.02 (t, 1H), 8.69 (bs, 1H), 7.58 (m, 4H), 7.30 (d, 1H), 7.15 (s, 1H), 7.09 (d, 1H), 4.08 (t, 2H), 3.38 (t, 2H), 3.21 (m, 10H), 3.18 (s, 3H), 2.81 (s, 2H), 2.73 (s, 3H), 1.86 (m, 2H), 1.49 (m, 2H), 1.41 (s, 6H), 0.87 (t, 3H).

EXAMPLE 9

3-{4'-[(4-acetylpiperazin-1-yl)methyl]-2-(3-methoxypropoxy)biphenyl-4-yl}-N-{[(2-hydroxybutyl)amino](imino)methyl}propanamide hydrochloride (Compound no 24)

Sodium (0.15 g, 6.5 mmol) was dissolved in ethanol (3.5 mL) at room temperature. Once all the sodium was dissolved, 2-tris(trimethylsilyl)silylhydroxybutylguanidine hydrochloride (2.45 g, 6.5 mmol) was added and the mixture was stirred for 1 h. A white precipitate formed and was filtered off. The filtrate was evaporated under reduced pressure and a solution of ethyl 3-{4'-[(4-acetylpiperazin-1-yl)methyl]-2-(3-methoxypropoxy)biphenyl-4-yl}propanoate (0.50 g, 1.0 mmol) and DMF (3.5 mL) was added at room temperature. After completion of the reaction, the mixture was poured into dichloromethane/brine (50/50). The aqueous layer was extracted three times with dichloromethane. The combined; organic layers were washed with brine, dried over anhydrous sodium sulfate, filtered and evaporated under reduced pressure. The residue was then dissolved in ethanol and HCl in diethyl ether (1N, 4 mL) was added. The mixture was evaporated and the residue was purified on reverse phase ($C_{18}$) flash chromatography ($H_2O$, HCl N/1000, acetonitrile, 100/0 to 80/20) to afford 0.11 g (15%) of the desired product as a white solid: mp=95° C.; $^1$H NMR (400 MHZ, CDCl$_3$) δ 13.20 (bs, 1H), 12.53 (bs, 1H), 9.53 (t, 1H), 7.62 (m, 4H), 7.21 (d, 1H), 6.98 (d, 1H), 6.96 (s, 1H), 4.71 (m, 1H), 4.23 (s, 2H), 4.06 (t, 2H), 3.89 (m, 2H), 3.53 (m, 6H), 3.41 (t, 2H), 3.29 (s, 3H), 3.08 (t, 2H), 2.95 (t, 2H), 2.85 (m, 2H), 2.12 (s, 3H), 2.00 (m, 2H), 1.59 (m, 2H), 1.00 (t, 3H).

EXAMPLE 10

3-[4'-{[4-(dimethylamino)piperidin-1-yl]methyl}-2-(3-methoxypropoxy)biphenyl-4-yl]-N-(5,5-dimethyl-4-oxo-1,4,5,6-tetrahydropyrimidin-2-yl)propanamide hydrochloride (Compound no 102)

Sodium (0.15 g, 6.5 mmol) was dissolved in ethanol (3.5 mL) at room temperature. Once all the sodium was dissolved, 3-{[amino(imino)methyl]amino}-2,2-dimethylpropanamide hydrochloride (1.26 g, 6.5 mmol) was added and the mixture was stirred for 1 hr. A white precipitate formed and was filtered off. The filtrate was evaporated under reduced pressure and a solution of ethyl 3-[4'-{[4-(dimethylamino)piperidin-1-yl]methyl}-2-(3-methoxy-propoxy)biphenyl-4-yl]propanoate (0.50 g, 1.0 mmol) and DMF (3.5 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 6 mL) was added. The mixture was evaporated and the residue was purified on reverse phase ($C_{18}$) flash chromatography ($H_2O$, HCl N/1000, acetonitrile, 100/0 to 80/20) to afford 0.12 g (19%) of the desired product as a white solid: mp=132° C.; $^1$H NMR (400 MHZ, $d_6$-DMSO) δ 7.50 (m, 4H), 7.23 (d, 1H), 7.00 (s, 1H), 6.91 (d, 1H), 4.02 (t, 2H), 3.51 (s, 2H), 3.38 (t, 2H), 3.29 (m, 4H), 3.20 (s, 3H), 3.02 (t, 2H), 2.95 (t, 2H), 2.69 (s, 6H), 2.05 (m, 5H), 1.82 (m, 2H), 1.17 (m, 2H), 1.05 (s, 6H).

EXAMPLE 11

N-[amino(imino)methyl]-3-[3-(2-methoxyethoxy)-4-pyridin-3-ylphenyl-]propanamide hydrochloride (Compound no 21)

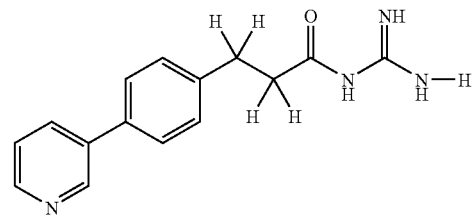

11.1 Ethyl 3-[3-(3-methoxypropoxy)-4-pyridin-3-ylphenyl]propanoate

Ethyl 3-[3-(3-methoxypropoxy)-4-{[(trifluoromethyl)sulfonyl]oxy}phenyl]propanoate (1.0 g, 2.4 mmol) was dissolved in dimethoxyethane (15 mL) and ethanol (1.5 mL). Pyridin-3-ylboronic acid (0.33 g, 2.65 mmol) was added and argon was bubbled in the mixture for 15 minutes. Cesium fluoride (0.8 g, 5.3 mmol) and tetrakistriphenylphosphine palladium (0.14 g, 0.1 mmol) were added and the mixture was brought to reflux under an argon atmosphere for 4 hours. After cooling to room temperature, solvents were evaporated under reduced pressure and the residue was dissolved in ethyl acetate/water (15 mL/15 mL). The organic layer was washed with saturated aqueous sodium bicarbonate and brine, dried over anhydrous sodium sulfate, filtered and evaporated under reduced pressure. The residue was purified by flash chromatography on silica gel (cyclohexane/ethyl acetate, 9/1) to yield 0.45 g (55%) of the desired product as a yellow oil.

11.2 N-[amino(imino)methyl]-3-[3-(2-methoxyethoxy)-4-pyridin-3-ylphenyl]propanamide hydrochloride Sodium (0.19 g, 8.3 mmol) was dissolved in ethanol (4.5 mL) at room temperature. Once all the sodium was dissolved, guanidine hydrochloride (0.79 g, 8.3 mmol) was added and the mixture was stirred for 1 hr. A white precipitate formed and was filtered off. The filtrate was evaporated under reduced pressure and a solution of ethyl 3-[3-(3-methoxypropoxy)-4-pyridin-3-ylphenyl]propanoate (0.45 g, 1.3 mmol) and DMF (4.5 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 4 mL) was added. The mixture was evaporated and the residue was purified on reverse phase ($C_{18}$) flash chromatography ($H_2O$, HCl N/1000, acetonitrile, 100/0 to 80/20) to afford 0.19 g (34%) of the desired product as a white solid: mp=91° C.; $^1$H NMR (400 MHZ, $d_6$-DMSO) δ 12.30 (s, 1H), 8.98 (s, 1H), 8.79 (d, 1H), 8.58 (d, 1H), 8.42 (bs, 3H), 7.92 (dd, 1H), 7.42 (d, 1H), 7.15 (s, 1H), 7.02 (d, 1H), 4.10 (t, 2H), 3.41 (t, 2H), 3.16 (s, 3H), 3.01 (t, 2H), 2.88 (t, 2H), 1.90 (t, 3H).

EXAMPLE 12

N-[imino(propylamino)methyl]-3-[2-(3-methoxypropoxy)-4'-(morpholin-4-ylcarbonyl)biphenyl-4-yl]-propanamide hydrochloride (Compound no 27)

12.1 Ethyl 3-[2-(3-methoxypropoxy)-4'-(morpholin-4-ylcarbonyl)biphenyl-4-yl]propanoate Ethyl 3-[3-(3-methoxypropoxy)-4-{[(trifluoromethyl)sulfonyl]oxy}phenyl]propanoate (0.8 g, 1.9 mmol) was dissolved in dimethoxyethane (12 mL) and ethanol (1.2 mL). 4-Morpholine-4-carbonylphenylboronic acid (0.50 g, 2.1 mmol) was added and argon: was bubbled in the mixture for 15 minutes. Cesium fluoride (0.6 g, 4.2 mmol) and tetrakistriphenylphosphine palladium (0.11 g, 0.1 mmol) were added and the mixture was brought to reflux under an argon atmosphere for 4 hours. After cooling to room temperature, solvents were evaporated under reduced pressure and the residue was dissolved in ethyl acetate/water (15 mL/15 mL). The organic layer was washed with saturated aqueous sodium bicarbonate and brine, dried over anhydrous sodium sulfate, filtered and evaporated under reduced pressure. The residue was purified by flash chromatography on silica gel (cyclohexane/ethyl acetate, 7/3) to yield 0.57 g (65%) of the desired product as a yellow oil.

12.2 N-[imino(propylamino)methyl]-3-[2-(3-methoxypropoxy)-4'-(morpholin-4-ylcarbonyl)biphenyl-4-yl]-propanamide hydrochloride Sodium (0.09 g, 3.9 mmol) was dissolved in ethanol (2 mL) at room temperature. Once all the sodium was dissolved, propylguanidine hydrochloride (0.54 g, 3.9 mmol) was added and the mixture was stirred for 1 hr. A white precipitate formed and was filtered off. The filtrate was evaporated under reduced pressure and a solution of ethyl 3-[2-(3-methoxypropoxy)-4'-(morpholin-4-ylcarbonyl)biphenyl-4-yl]propanoate (0.28 g, 0.6 mmol) and DMF (2 mL) was added at room temperature. After completion of the reaction, the mixture was poured into dichloromethane/brine (50/50). The aqueous layer was extracted three times with dichloromethane. The combined organic layers were washed with brine, dried over anhydrous sodium sulfate, filtered and evaporated under reduced pressure. The residue was then dissolved in ethanol and HCl in diethyl ether (1N, 2 mL) was added. The mixture was evaporated and the residue was purified on reverse phase ($C_{18}$) flash chromatography ($H_2O$, HCl N/1000, acetonitrile, 100/0 to 80/20) to afford 0.08 g (25%) of the desired product as a white solid: mp=79° C.; $^1$H NMR (400 MHZ, $d_6$-DMSO) δ 12.02 (bs, 1H), 9.03 (bs, 1H), 8.69 (bs, 1H), 7.49 (m, 4H), 7.23 (d, 1H), 7.02 (s, 1H), 6.90 (d, 1H), 4.08 (t, 2H), 3.57 (m, 6H), 3.50 (m, 4H), 3.26 (t, 2H), 3.17 (s, 3H), 2.98 (t, 2H), 2.80 (t, 2H), 1.88 (m, 2H), 1.51 (q, 2H), 0.90 (t, 3H).

EXAMPLE 13

N-butyl-N'-{3-[4'-[4-(2,2-dimethyl-propionyl)-piperazin-1-yl-methyl]-2-(3-methoxy-propoxy)-biphenyl-4-yl]-propionyl}-guanidine, trifluoro-acetic acid salt (Compound no 42)

13.1 Ethyl-3-[4'-[4-(2,2-Dimethyl-propionyl)-piperazin-1-yl-methyl]-2-(3-methoxy-propoxy)-biphenyl-4-yl]propionate To a solution of 2,2-dimethyl-1-piperazin-1-yl-propan-1-one (37.45 mg, 0.22 mmol) in THF (2 mL) concentrated acetic acid (63 μL, 1.1 mmol), Ethyl-3-[4'-Formyl-2-(2-methoxy-ethoxy)-biphenyl-4-yl]-propionate (74 mg, 0.2 mmol) dissolved in THF (1 mL) and cyanoborhydride resin (123 mg, 0.3 mmol) was added. The reaction was shaken in a closed-vessel under argon at r.t. overnight. The mixture was filtered and dried under reduced pressure. The residue was redissolved in ethyl acetate (20 mL) and washed with an aqueous sodium hydrogen carbonate solution (20 mL). The organic layer was separated, dried over sodium sulfate, filtered and dried under reduced pressure to give 80.6 mg of the titled compound.

13.2 N-butyl-N'-{3-[4'-[4-(2,2-dimethyl-propionyl)-piperazin-1-yl-methyl]-2-(3-methoxy-propoxy)-biphenyl-4-yl]-propionyl}-guanidine, trifluoro-acetic acid salt The crude product derived from step 1 was dissolved in DMF (1 mL) and treated with a solution of N-butyl-guanidine hydrochloride (182 mg, 1.2 mmol) and potassium tert-butylate (134 mg, 1.2 mmol) in DMF (2 mL). The reaction was stirred in a closed vessel at 80° C. for 36 h. The cooled mixture was filtered and dried under reduced pressure. The residue was redissolved in ethyl acetate (20 mL) and washed with an aqueous sodium chloride solution (20 mL). The organic layer was separated, dried over sodium sulfate, filtered and dried under reduced pressure. The residue was redissolved in DMF and separated by prep-HPLC. The relevant fractions were lyophilized overnight to give 27.3 mg (23% yield over two steps) of the pure compound. LC/MS (method A) main peak (M+): 593.39 ($R_t$=1.25 min). $^1$H-NMR (500 MHz, DMSO-$d_6$) δ (ppm): 0.89 (t, 3H), 1.21 (s, 9H), 1.28-1.34 (m, 2H), 1.47-1.53 (m, 2H), 1.85-1.91 (m, 2H), 2.79-2.85 (m, 2H), 2.90-2.93 (m, 2H), 3.00-3.09 (br.m, 2H), 3.09-3.19 (br.m, 2H), 3.21 (s, 3H), 3.24-3.28 (m, 2H), 3.37-3.41 (m, 4H), 4.02-4.05 (m, 2H), 4.35-4.48 (br.m, 4H), 6.92 (d, 1H), 7.02 (s, 1H), 7.20-7.25 (m, 1H), 7.48-7.55 (br.d, 2H), 7.55-7.63 (br.d, 2H), 8.73 (br.s, 1-2H), 9.15 (br.s, 1H), 9.95 (br.s, 1H), 11.75 (br.s, 1H)

EXAMPLE 14

N-butyl-N'-{3-[4'-[(2-dimethylamino-2-phenyl-ethylamino)-methyl]-2-(3-methoxy-propoxy)-biphenyl-4-yl]-propionyl}-guanidine, trifluoro-acetic acid salt (Compound no 48)

14.1 Ethyl-3-[4'-[(2-dimethylamino-2-phenyl-ethylamino)-methyl]-2-(3-methoxy-propoxy)-biphenyl-4-yl]propionate In analogy to the preparation of example 13.1, N1,N1-dimethyl-1-phenyl-ethane-1,2-diamine (36.1 mg, 0.22 mmol) was converted yielding 74.8 mg of the titled compound. LC/MS (method C) (M+H)$^+$: 519

14.2 N-butyl-N'-{3-[4'-[(2-dimethylamino-2-phenyl-ethylamino)-methyl]-2-(3-methoxy-propoxy)-biphenyl-4-yl]-propionyl}-guanidine, trifluoro-acetic acid salt In analogy to the preparation of example 13.2, the product obtained in 14.1 was converted yielding 19.1 mg (16% yield over two steps) of the solid product. LC/MS (method A) main peak (M$^+$): 587.38 (R$_t$=1.13 min). $^1$H-NMR (500 MHz, DMSO-d$_6$) δ (ppm): 0.89 (t, 3H), 1.27-1.35 (m, 2H), 1.47-1.53 (m, 2H), 1.83-1.88 (m, 2H), 2.08-2.34 (br.m, 6H), 4.45-2.55 (DMSO solvent peak), 2.78-2.83 (m, 2H), 2.88-2.93 (m, 2H), 3.19 (s, 3H), 3.24-3.28 (q, 2H), 3.37 (t, 2H), 3.4-3.8 (H$_2$O solvent peak), 4.02 (t, 2H), 4.21 (s, 2H), 6.90 (d, 1H), 7.00 (s, 1H), 7.22 (d, 1H), 7.30-7.58 (br.m, 9H), 8.70 (br.s, 1-2H), 9.09 (br.s, 1H), 11.66 (br.s, 1H); some signals not observed possibly due to overlay with solvent peaks.

EXAMPLE 15

N-{3-[4'-(4-benzoyl-piperazin-1-ylmethyl)-2-(3-methoxy-propoxy)-biphenyl-4-yl]-propionyl}-N'-butyl-guanidine, trifluoro-acetic acid salt (Compound no 28)

15.1 Ethyl-3-[4'-(4-benzoyl-piperazin-1-ylmethyl)-2-(3-methoxy-propoxy)-biphenyl-4-yl]propionate In analogy to the preparation of example 13.1, phenyl-piperazin-1-yl-methanone (41.8 mg, 0.22 mmol) was converted yielding 81.0 mg of the titled compound. LC/MS (method C) (M+H)$^+$: 545

15.2 N-{3-[4'-(4-benzoyl-piperazin-1-ylmethyl)-2-(3-methoxy-propoxy)-biphenyl-4-yl]-propionyl}-N'-butyl-guanidine, trifluoro-acetic acid salt In analogy to the preparation of example 13.2, the product obtained in 15.1 was converted yielding 19.7 mg (16% yield over two steps) of the solid product. LC/MS (method A) main peak (M$^+$): 613.36 (R$_t$=1.25 min). $^1$H-NMR (500 MHz, DMSO-d$_6$) δ (ppm): 0.89 (t, 3H), 1.27-1.34 (m, 2H), 1.47-1.53 (m, 2H), 1.85-1.90 (m, 2H), 247-2.56 (DMSO solvent peak), 2.79-2.84 (m, 2H), 2.90-2.93 (m, 2H), 3.20 (s, 3H), 3.24-3.28 (m, 2H), 3.29-3.55 (H$_2$O solvent peak), 4.01-4.04 (m, 2H), 4.38 (br.s, 1-2H), 6.91 (d, 1H), 7.01 (s, 1H), 7.20-7.25 (m, 1H), 7.46-7.51 (br.m, 7H), 7.59 (br.s, 2H), 8.69 (br.s, 1-2H), 9.07 (br.s, 1H), 9.98 (br.s, 1H), 11.64 (br.s, 1H); some signals not observed possibly due to overlay with solvent peaks.

EXAMPLE 16

3-{3'-[(tert-butylsulfonyl)methyl]-4'-chloro-2-(3-methoxypropoxy)biphenyl-4-yl}-N-(methylcarbamimidoyl)propanamide hydrochloride (Compound no 194)

16.1 5-Bromo-2-chloro-3-[[1,1-dimethylethyl]thio]methyl]-benzene

To a solution of sodium tert-butyl thiolate (1.08 g, 9.64 mmol) in 42 ml of ethanol 5-Bromo-2-chlorobenzyl bromide (2.74 g, 9.64 mmol) dissolved in 19 ml of ethanol was added and the mixture was brought to reflux under an atmosphere of argon for 15 hours. After cooling to room temperature, the solvent was evaporated under reduced pressure and the residue was dissolved in ethylacetate and washed with brine. The organic layer was dried over anhydrous sodium sulfate, filtered and evaporated under reduced pressure, yielding 2.34 g (84%) of the desired product.

16.2 5-Bromo-2-chlorobenzyl tert-butyl sulfone

5-Bromo-2-chloro-3-[[1,1-dimethylethyl]thio]methyl]-benzene (2.38 g, 8.1 mmol) and potassium permanganate (8.07 g; 51.06 mmol) were dissolved in 217 ml of acetonitrile and stirred at room temperature for 11 hours. The mixture was filtered on diatomaceous earth and the filtrate was treated with an aqueous solution of 10% NaHSO$_3$ and extracted several times with ether. The organic layers were dried over magnesium sulphate, filtered and evaporated under reduced pressure. The residue was purified by flash chromatography on silica gel (cyclohexane/ethyl acetate, 9/1) to yield 0.932 g (35%) of the expected sulfone.

16.3 2-{3-[(tert-Butylsulfonyl)methyl]-4-chlorophenyl}-4,4,5,5-tetramethyl-1,3,2-dioxaborolane To a stirred solution of 5-bromo-2-chlorobenzyl tert-butyl sulfone (0.93 g, 2.86 mmol) and bis(pinacolato)diborane (0.872 g, 3.43 mmol): in 11.6 ml of dioxane, were added potassium acetate (1.12 g, 11.45 mmol) and bis(triphenylphosphine)palladium (II) chloride (0.14 g, 0.17 mmol) and the mixture was brought to reflux under an atmosphere of argon for 2.5 hours. After cooling to room temperature, the solvent was evaporated under reduced pressure and the residue was dissolved in ethyl acetate and water. The organic layer was washed with brine, dried over anhydrous sodium sulphate, filtered and evaporated under reduced pressure, providing 1.04 g (99%) of the desired product.

16.4 Ethyl 3-{3'-[(tert-butylsulfonyl)methyl]-4'-chloro-2-(3-methoxypropoxy)biphenyl-4-yl}propanoate Ethyl 3-[3-(3-methoxypropoxy)-4-{[(trifluoromethyl)sulfonyl]oxy}phenyl]propanoate (1.1 g, 2.65 mmol) was dissolved in 1,2-dimethoxyethane (15.7 ml) and ethanol (1.5 ml). 2-{3-[(tert-butylsulfonyl)methyl]-4-chlorophenyl}-4,4,5,5-tetramethyl-1,3,2-dioxaborolane (1.09 g, 2.92 mmol) was added and argon was bubbled in the solution for 10 minutes. Cesium fluoride (0.89 g, 5.84 mmol) and palladium tetrakistriphenylphosphine (0.153 g, 0.13 mmol) were: added for 2.5 hours. After cooling to room temperature, solvents were evaporated under reduced pressure and the residue was dissolved in ethyl acetate and water. The organic phase was washed with saturated aqueous ammonium chloride and brine, dried over anhydrous sodium sulphate, filtered and evaporated under reduced pressure. The residue was purified by flash chromatography on silica gel (cyclohexane/ethyl acetate, 9/1) giving 0.53 g (39%) of the desired product.

16.5 3-{3'-[(tert-butylsulfonyl)methyl]-4'-chloro-2-(3-methoxypropoxy)biphenyl-4-yl}-N-(methylcarbamimidoyl)propanamide, hydrochloride Sodium (0.15 g, 6.48 mmol) was dissolved in ethanol (3.4 ml) at room temperature. Once all the sodium was dissolved, methylguanidine hydrochloride (0.71 g, 6.47 mmol) was added and the mixture was stirred for 1.5 hours. The white precipitate formed was filtered off, the filtrate was evaporated under reduced pressure and a solution of ethyl 3-{3'-[(tert-butylsulfonyl)methyl]-4'-chloro-2-(3-methoxypropoxy)biphenyl-4-yl}propanoate (0.53 g, 1.04 mmol) in DMF (3.4 ml) was added at room temperature. The mixture was stirred for 12 hours then poured into dichloromethane/brine (50/50). The aqueous layer was extracted three times with dichloromethane and the combined organic phases were washed with brine, dried over sodium sulphate, filtered and evaporated under reduced pressure, providing 0.59 g of the desired base. This residue was then dissolved in acetonitrile (4 ml) and HCl 4N in dioxane (0.63 ml) and was stirred for 2 hours at room temperature before being evaporated. The residue was purified on reverse phase (C18) flash chromatography (aqueous: HCl N/1000, acetonitrile, 100/0 to 80/20) to afford 0.14 g of the desired product as a white solid: mp=44-45° C.; 1H (400 MHz), $d_6$-DMSO) δ 8.97 (bs, 1H), 8.56 (bs, 2H), 7.66 (S, 1H), 7.56 (S, 2H), 7.25 (d, 1H), 7.08 (S, 1H), 4.61 (S, 2H), 4.08 (t, 2H), 3.41 (t, 2H), 3.21 (S, 3H), 3.0-2.8 (m, 7H), 1.92 (m, 2H), 4.40 (S, 9H).

EXAMPLE 17

N-{2'-(3-methoxypropoxy)-4'-[3-(methylcarbamimidamido)-3-oxopropyl]biphenyl-3-yl}-N-methylmorpholine-4-carboxamide hydrochloride (Compound no 195)

17.1 N-(3-Bromophenyl)-4-morpholinecarboxamide

Morpholine (1.1 g, 12.62 mmol) was dissolved in dichloromethane and m-bromophenyl isocyante (2.5 g, 12.62 mmol) was added at room temperature and the 30, solution was stirred for 75 minutes. The precipitate formed was filtered and triturated with a small amount of diethyl ether, then dried at 40° C. under reduced pressure, yielding 2.90 g (81%) of the expected product.

17.2 N-Methyl, N-(3-bromophenyl)-4-morpholinecarboxamide

N-(3-Bromophenyl)-4-morpholinecarboxamide (2.90 g, 10.18 mmol) was dissolved in DMF (41 ml) and the solution was cooled to 0° C. Sodium hydride (0.268 g, 11.18 mmol) was added by small amounts and the mixture was stirred at 0° C. for 15 minutes, then at room temperature for 1 hour. The mixture was cooled to 0° C. and iodomethane (0.79 ml, 12.73 mmole) was added and the mixture was stirred at room temperature for 4 hours, then recooled to 0° C., 50 ml of ethyl acetate were added followed by 100 ml $H_2O$/aqueous saturated solution of ammonium chloride 1:1, by small amounts. The organic phase was separated and the aqueous phase was extracted three times with ethylacetate. The combined organic phases were washed with brine, dried over anhydrous sodium sulphate, filtered and evaporated under reduced pressure. The residue was purified by flash chromatography on silica gel (dichloromethane/methanol, 95/5) to yield 1.42 g (47%) of the desired product as an oil.

17.3 N-methyl-N-[3-(4,4,5,5-tetramethyl-1,3,2-dioxaborolan-2-yl)phenyl]morpholine-4-carboxamide To a stirred solution of N-methyl,N-(3-bromophenyl)-4-morpholinecarboxamide (1.42 g, 4.75 mmol) and bis(pinacolato)diborane (1.45 g, 5.70 mmol) in 25 ml of dioxane, were added potassium acetate (1.86 g, 19.0 mmol) and bis(triphenylphosphine)palladium (II) chloride, dichloromethane complex (0.233 g, 0.285 mmol) sand the mixture was brought to reflux under an atmosphere of argon for 1.5 hours. After cooling to room temperature, the solvent was evaporated under reduced pressure and the residue was dissolved in ethyl acetate and water. The organic layer was washed with brine, dried over anhydrous sodium sulphate, filtered and evaporated under reduced pressure. The residue was purified by flash chromatography on silica gel (cyclohexane/ethyl acetate 8/2, then 7/3) to give 1.06 g (65%) of the desired product.

17.4 Ethyl 3-{2-(3-methoxypropoxy)-3'-[methyl(morpholin-4-ylcarbonyl)amino]biphenyl-4-yl}propanoate Ethyl 3-[3-(3-methoxypropoxy)-4-{[(trifluoromethyl)sulfonyl]oxy}phenyl]propanoate (1.0 g, 2.40 mmol) was, dissolved in 1,2-dimethoxyethane (14.4 ml) and ethanol (1.6 ml). N-methyl-N-[3-(4,4,5,5-tetramethyl-1,3,2-dioxaborolan-2-yl)phenyl]morpholine-4-carboxamide (0.914 g, 2.64 mmol) was added and argon was bubbled in the solution for 10 minutes. Cesium fluoride (0.80 g, 5.28 mmol) and palladium tetrakistriphenylphosphine (0.139 g, 0.12 mmol) were added and the mixture was heated to reflux under an argon atmosphere for 14 hours. After cooling to room temperature, solvents were evaporated under reduced pressure and the residue was dissolved in ethyl acetate and water. The organic phase was washed with saturated aqueous ammonium chloride and brine, dried over anhydrous sodium sulphate, filtered and evaporated under reduced pressure. The residue was purified by flash chromatography on silica gel (cyclohexane/ethyl acetate, 7/3) giving 0.232 g (20%) of the desired product.

17.5 N-{2'-(3-methoxypropoxy)-4'-[3-(methylcarbamimidamido)-3-oxopropyl]biphenyl-3-yl}-N-methylmorpholine-4-carboxamide hydrochloride Sodium (0.069 g, 3.00 mmol) was dissolved in ethanol (2 ml) at room temperature. Once all the sodium was dissolved, methylguanidine hydrochloride (0.328 g, 2.99 mmol) was added and the mixture was stirred for 1.5 hours. The white precipitate formed was filtered off, the filtrate was evaporated under reduced pressure and a solution of ethyl 3-{2-(3-methoxypropoxy)-3'-[methyl(morpholin-4-ylcarbonyl)amino]biphenyl-4-yl}propanoate (0.232 g, 0.48 mmol) in DMF (1.5 ml) was added at room temperature. The mixture was stirred for 12 hours then poured into dichloromethane/brine (50/50). The aqueous layer was extracted three times with dichloromethane and the combined organic phases were washed with brine, dried over sodium sulphate, filtered and evaporated under reduced pressure, providing 0.59 g of the desired base. This residue was then dissolved in acetonitrile (2 ml) and HCl 4N in dioxane (2 ml) and was stirred for 2 hours: at room temperature before being evaporated. The residue was purified on reverse phase (C18) flash chromatography (aqueous HCl N/1000, acetonitrile, 80/20) to afford, 0.155 g (59%) of the desired product as a white solid: mp=54.5° C.; 1H (400 MHz), $d_6$-DMSO) δ 8.90 (bs, 1H), 8.52 (bs, 2H), 7.50 (t, 1H), 7.25 (m, 3H), 7.09 (d, 1H), 7.02 (S, 1H), 6.83 (d, 1H), 4.05 (t, 2H), 3.45-3.37 (m, 7H), 3.22 (S, 3H), 3.12 (m, 8H), 3.98-3.78 (m, 7H), 2.90 (m, 2H).

EXAMPLE 18

3-{2-(3-methoxypropoxy)-3'-[(morpholin-4-ylsulfonyl)methyl]biphenyl-4-yl}-N-[(1-methylethyl)carbamimindoyl]propanamide hydrochloride (Compound no 206)

18.1 N-[imino(1H-pyrazol-1-yl)methyl]-3-{2-(3-methoxypropoxy)-3'-[(morpholin-4-ylsulfonyl)methyl]biphenyl-4-yl}propanamide Ethyl 3-{2-(3-methoxypropoxy)-3'-[(morpholin-4-ylsulfonyl)methyl]biphenyl-4-yl}propanoate (1.00 g, 1.98 mmol), synthesized according to the preceding examples by coupling 4-{[3-(4,4,5,5-tetramethyl-1,3,2-dioxaborolan-2-yl)benzyl]sulfonyl}morpholine and ethyl 3-[3-(3-methoxypropoxy)-4-{[(trifluoromethyl)sulfonyl]oxy}phenyl]propanoate, was dissolved in ethanol (18 ml). Potassium hydroxide (0.333 g, 5.93 mmoles) and 0.54 g of water were added and the mixture was heated to reflux for 1 hour then evaporated to dryness under reduced pressure yielding 1.46 g of the potassium salt. 1.00 g of this intermediate was then taken up in dichloromethane (14 ml) and 1H-pyrazole-1-carboximidamide hydrochloride (2.21 g, 10.47 mmol), 1,1'-carbonyldiimidazole (1.7 g, 10.47 mmol), DMAP (0.512 g, 13.62 mmol) and triethylamine (2.92 ml, 20.94 mmol) were added and the solution was stirred for 16 hours at room temperature. The mixture was then poured into dichloromethane and water and the aqueous layer was separated and re-extracted twice with DCM. The combined organic phases were washed with brine, dried on anhydrous sodium sulphate, filtered, and evaporated. The residue was purified by flash chromatography on silica gel (dichloromethane/methanol, 92:8) to yield 0.68 g (50%) of the desired product.

18.2 3-{2-(3-methoxypropoxy)-3'-[(morpholin-4-ylsulfonyl)methyl]biphenyl-4-yl}-N-[(1-methylethyl)carbamimidoyl]propanamide hydrochloride (Compound no 206)

The intermediate obtained from 18.1 (0.25 g, 0.44 mmol) was dissolved in a solution of DCM (2 ml) containing isopropylamine (0.15 ml, 1.76 mmol) and stirred at room temperature in a sealed tube for 24 hours. The solution was evaporated to dryness and the hydrochloride salt was made in the usual manner as previously described. The desired product was obtained as a white solid: mp=206° C.; 1H NMR (400 MHz, $d_6$-DMSO) δ 8.82 (d, 1H), 8.60 (bs, 2H), 7.54 (S, 1H), 7.49 (m, 1H), 7.44-7.33 (m, 5H), 7.20 (d, 1H), 7.02 (S, 1H), 4.48 (S, 2H), 4.03 (t, 2H), 3.90 (m, 1H), 3.58 (m, 4H), 3.38 (t, 2H), 3.22 (S, 3H), 3.13 (m, 4H), 2.93 (d, 2H), 2.79 (t, 2H), 1.89 (m, 2H), 1.18 (d, 6H).

The following tables illustrate the chemical structures and the physical properties of some examples of compounds according to the present invention. Table 1 discloses compounds of formula (I bis), i.e. compounds of formula (I) according to the present invention wherein X, Y and Z represent carbon atoms, R4, R9 and R10 are hydrogen atoms and -Q-R3 represents an —O—$(CH_2)_3$—$OCH_3$ group. Table 2 discloses compounds of formula (I ter), i.e. compounds of formula (I) according to the present invention wherein X, Y and Z represent carbon atoms, R2, R4, R5, R6, R7, R8, R9 and R10 are hydrogen atoms. Table 3 discloses compounds of formula (I quater), i.e. compounds of formula (I) according to the present invention wherein X, Y and Z represent carbon atoms, R2, R4, R7 and R8 are hydrogen atoms and -Q-R3 represents an —O—$(CH_2)_3$—$OCH_3$ group. In these tables:

- in the <<salt>> columnn, <<HCl>> represents a compound in the form of a hydrochloride and <<$F_3C$—$CO_2H$>> represents a compound in the form of a trifluoroacetate,
- Me, Et, n-Pr, n-Bu and tBu respectively represent methyl, ethyl, n-propyl, n-butyl and tertbutyl groups, and
- LC represents the retention time of the compounds, in minutes.

TABLE 1

[Structure (I bis): A phenyl ring substituted with R1, R2 (on ring A), connected to another phenyl bearing R5, R6 and an O-CH2CH2CH2-OCH3 group; with a -C(R7)(R8)-C(=O)-NH-N(H)-C(=NH)-NH-R11 side chain]

| N° | R1 | R2 | A | R5 | R6 | R7 | R8 | R11 | salt | m.p. (°C.) | MS peak | LC (method) |
|----|----|----|---|----|----|----|----|-----|------|------------|---------|-------------|
| 1 | 4-(N-methylpiperazin-1-yl)methyl-* | H | 1,4-phenylene (*) | H | H | H | H | H | 3 HCl | 190 | 468 (M + 1) | 4.9 (D) |
| 2 | 1-methyl-4-(aminomethyl*)piperidin-4-yl | H | 1,4-phenylene (*) | H | H | H | H | H | 3 HCl | 220 | 496 (M + 1) | 5.08 (D) |
| 3 | 1-methyl-4-(aminomethyl*)piperidin-4-yl | H | 1,4-phenylene (*) | H | H | H | H | n-Bu | 3 HCl | 125 | 524 (M + 1) | 5.99 (D) |
| 4 | 1-methyl-4-(aminomethyl*)piperidin-4-yl | H | 1,4-phenylene (*) | H | H | H | H | n-Bu | 3 HCl | 201 | 552 (M + 1) | 4.1 (D) |
| 5 | 1-methyl-4-(aminomethyl*)piperidin-4-yl | H | 1,4-phenylene (*) | H | H | H | H | -(CH2)3-N(Et)2 * | 4 HCl | 48 | 609 (M + 1) | 3.2 (D) |

TABLE 1-continued (I bis)

| N° | R1 | R2 | A | R5 | R6 | R7 | R8 | R11 | salt | m.p. (°C.) | MS peak | LC (method) |
|----|----|----|----|----|----|----|----|-----|------|-----------|---------|-------------|
| 6 | 1-methyl-piperidin-4-yl-N-methyl | H | 1,4-phenylene | H | H | H | H | -CH₂CH₂-(pyridin-2-yl) | 4 HCl | 128 | 601 (M + 1) | 4.5 (D) |
| 7 | 1-methyl-piperidin-4-yl-N-methyl | H | 1,4-phenylene | H | H | H | H | -CH₂CH₂-CH(OH)CH₃ | 3 HCl | 105 | 568 (M + 1) | 2.4 (D) |
| 8 | 1-methyl-piperidin-4-yl-N-methyl | H | 1,4-phenylene | H | H | H | H | -CH₂CH₂CH₂-OCH₃ | 2 HCl | 48 | 568 (M + 1) | 5.4 (D) |
| 9 | 1-methyl-piperidin-4-yl-N-methyl | H | 1,4-phenylene | H | H | H | H | -CH₂-cyclopropyl | 3 HCl | 248 | 564 (M + 1) | 4.2 (D) |
| 10 | H | H | phenyl | H | H | H | H | n-Bu | 1 HCl | 229 | 412 (M + 1) | 8.3 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 11 | (4-dimethylamino-piperidin-1-yl)methyl* | H | para-phenylene | H | H | H | H | 3-methylbutyl | 2 HCl | | 566 (M + 1) | 6.3 (D) |
| 12 | piperidin-1-ylmethyl* | H | para-phenylene | H | H | H | H | n-Bu | 1 HCl | 89 | 509 (M + 1) | 4.8 (D) |
| 13 | piperidin-1-ylmethyl* | H | para-phenylene | H | H | H | H | H | 1 HCl | 70 | 453 (M + 1) | 6.12 (D) |
| 14 | (4-acetylpiperazin-1-yl)methyl* | H | para-phenylene | H | H | H | H | H | 2 HCl | 138 | 496 (M + 1) | 6.10 (D) |
| 15 | (4-acetylpiperazin-1-yl)methyl* | H | para-phenylene | H | H | H | H | n-Bu | 2 HCl | 85 | 552 (M + 1) | 4.3 (D) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 16 | 1-methyl-4-(methylamino)piperidinyl-CH2- | H | 1,4-phenylene | H | H | H | H | cyclopropyl | 3 HCl | 204 | 536 (M+1) | 3.9 (D) |
| 17 | 1-methyl-4-(methylamino)piperidinyl-C(O)- | H | 1,4-phenylene | H | H | H | H | H | 2 HCl | 122 | 482 (M+1) | 5.21 (D) |
| 18 | 1-methyl-4-(methylamino)piperidinyl-CH2- | H | 1,4-phenylene | Me | H | H | H | H | 2 HCl | 151 | 510 (M+1) | 5.20 (D) |
| 19 | 1-methyl-4-aminopiperidinyl-CH2- | H | 1,4-phenylene | H | H | H | H | n-Bu | 3 HCl | 133 | 538 (M+1) | 4.1 (D) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 20 | N-methyl-piperidin-4-yl-methyl (N-Me piperidine, CH2*) | H | 1,4-phenylene | H | H | H | H | Me | 3 HCl | 70 | 510 (M + 1) | 4.1 (D) |
| 21 | H | H | pyridin-3,5-diyl | H | H | H | H | H | 2 HCl | 91 | 357 (M + 1) | 5.80 (D) |
| 22 | N-methyl-piperidin-4-yl-methyl | H | 1,4-phenylene | Me | Me | H | H | H | 3 HCl | 105.5 | 524 (M + 1) | 5.55 (D) |
| 23 | H | H | pyrimidin-2,5-diyl | H | H | H | H | H | 2 HCl | 77 | 358 (M + 1) | 5.04 (D) |
| 24 | N-acetyl-piperazin-1-yl-CH2* | H | 1,4-phenylene | H | H | H | H | CH2-CH(OH)-CH2CH3 | 2 HCl | 95 | 568 (M + 1) | 4.7 (D) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 25 | 4-methylpiperazine-1-carbonyl | H | 1,4-phenylene | Me | Me | H | H | n-Pr | 2 HCl | 99 | 552 (M+1) | 6.25 (D) |
| 26 | 4-acetylpiperazin-1-yl-methyl | H | 1,4-phenylene | H | H | H | H | n-Pr | 2 HCl | 115 | 538 | 4.90 (D) |
| 27 | morpholine-4-carbonyl | H | 1,4-phenylene | H | H | H | H | n-Pr | 1 HCl | 79 | 511 (M+1) | 6.52 (D) |
| 28 | 4-benzoylpiperazin-1-yl-methyl | H | 1,4-phenylene | H | H | H | H | n-Bu | F$_3$C—CO$_2$H | — | 613.36 | — (A) |

TABLE 1-continued

(I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 29 | pyridin-3-ylmethyl-piperazinyl | H | 1,4-phenylene | H | H | H | H | n-Bu | F$_3$C—CO$_2$H | — | 600.38 | — (A) |
| 30 | N,N-dimethylcarbamoylmethyl-piperazinyl | H | 1,4-phenylene | H | H | H | H | n-Bu | F$_3$C—CO$_2$H | — | 594.39 | — (A) |
| 31 | 4-(di-n-propylamino)piperidin-1-ylmethyl | H | 1,4-phenylene | H | H | H | H | n-Bu | F$_3$C—CO$_2$H | — | 607.45 | — (A) |
| 32 | pyridin-3-ylmethyl-piperazinyl | H | 1,4-phenylene | H | H | H | H | n-Bu | F$_3$C—CO$_2$H | — | 600.38 | — (A) |
| 33 | 4-(pyrrolidin-1-yl)piperidin-1-ylmethyl | H | 1,4-phenylene | H | H | H | H | n-Bu | F$_3$C—CO$_2$H | — | 577.40 | — (A) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 34 | (CH3)2N-CH2CH2-NH-* | H | 1,4-phenylene | H | H | H | H | n-Bu | F3C—CO2H | — | 512.61 (M + 1) | — (B) |
| 35 | morpholine-C(O)-piperazine-CH2-* | H | 1,4-phenylene | H | H | H | H | n-Bu | F3C—CO2H | — | 622.38 | — (A) |
| 36 | piperidine-C(O)-piperazine-CH2-* | H | 1,4-phenylene | H | H | H | H | n-Bu | F3C—CO2H | — | 620.41 | — (A) |
| 37 | pyridine-3-C(O)-piperazine-CH2-* | H | 1,4-phenylene | H | H | H | H | n-Bu | F3C—CO2H | — | 615.53 (M + 1) | — (B) |
| 38 | 2,6-dimethylpiperazine-CH2-* | H | 1,4-phenylene | H | H | H | H | n-Bu | F3C—CO2H | — | 538.57 (M + 1) | — (B) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 39 | (1-methylpyrazol-4-yl)methyl-piperazinyl | H | 1,4-phenylene | H | H | H | H | n-Bu | F$_3$C—CO$_2$H | — | 603.39 | —(A) |
| 40 | N,N-diethyl-propane-1,2-diamine | H | 1,4-phenylene | H | H | H | H | n-Bu | F$_3$C—CO$_2$H | — | 553.40 | —(A) |
| 41 | 1-benzyl-4-(diethylamino)piperidinyl | H | 1,4-phenylene | H | H | H | H | n-Bu | F$_3$C—CO$_2$H | — | 641.43 | —(A) |
| 42 | 4-pivaloyl-piperazinyl | H | 1,4-phenylene | H | H | H | H | n-Bu | F$_3$C—CO$_2$H | — | 593.39 | —(A) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 43 | piperazine-N-C(O)-cyclohexyl | H | *-C6H4-* (para) | H | H | H | H | n-Bu | F3C—CO2H | — | 591.41 | (A) |
| 44 | (1-ethylpyrrolidin-2-yl)methyl-NH- | H | *-C6H4-* (para) | H | H | H | H | n-Bu | F3C—CO2H | — | 552.58 (M+1) | (B) |
| 45 | 4-isobutylpiperazin-1-yl-CH2- | H | *-C6H4-* (para) | H | H | H | H | n-Bu | F3C—CO2H | — | 565.40 | (A) |
| 46 | 4-(3-methoxypropyl)piperazin-1-yl-CH2- | H | *-C6H4-* (para) | H | H | H | H | n-Bu | F3C—CO2H | — | 582.59 (M+1) | (B) |
| 47 | (1-methylpyrrolidin-3-yl)methyl-N- | H | *-C6H4-* (meta) | H | H | H | H | n-Bu | F3C—CO2H | — | 537.40 | (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 48 | PhCH(NMe2)CH2NH- | H | *-C6H4-* | H | H | H | H | n-Bu | F3C—CO2H | — | 587.38 | (A) |
| 49 | 2-pyridyl-piperazinyl-CH2- | H | *-C6H4-* | H | H | H | H | n-Bu | F3C—CO2H | — | 587.51 (M+1) | (B) |
| 50 | cyclopentyl-piperazinyl-CH2- | H | *-C6H4-* | H | H | H | H | n-Bu | F3C—CO2H | — | 577.40 | (A) |
| 51 | PhCH2N(Me)CH2CH2N(Me)CH2- | H | *-C6H4-* | H | H | H | H | n-Bu | F3C—CO2H | — | 601.40 | (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 52 | 4-benzyl-3-oxopiperazin-1-ylmethyl | H | 1,4-phenylene | H | H | H | H | n-Bu | F$_3$C—CO$_2$H | — | 613.36 | (A) |
| 53 | 4-(diethylamino)piperidin-1-ylmethyl | H | 1,4-phenylene | H | H | H | H | n-Bu | F$_3$C—CO$_2$H | — | 590.60 (M + 1) | (B) |
| 54 | 4-(pentan-3-yl)piperazin-1-ylmethyl | H | 1,4-phenylene | H | H | H | H | n-Bu | F$_3$C—CO$_2$H | — | 590.60 (M + 1) | (B) |
| 55 | 2-(dimethylamino)ethyl(ethyl)aminomethyl | H | 1,4-phenylene | H | H | H | H | n-Bu | F$_3$C—CO$_2$H | — | 540.56 | (B) |
| 56 | 4-((tetrahydrofuran-2-yl)methyl)piperazin-1-ylmethyl | H | 1,4-phenylene | H | H | H | H | n-Bu | F$_3$C—CO$_2$H | — | 593.39 | (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 57 | (S)-1-(*-methyl)-3-(dimethylamino)pyrrolidine | H | 1,4-phenylene | H | H | H | H | n-Bu | F$_3$C—CO$_2$H | — | 537.37 | — (A) |
| 58 | 1-(*-methyl)-4-(pyridin-4-yl)piperazine | H | 1,4-phenylene | H | H | H | H | n-Bu | F$_3$C—CO$_2$H | — | 586.36 | — (A) |
| 59 | 1-(*-methyl)-4-(pyrimidin-2-yl)piperazine | H | 1,4-phenylene | H | H | H | H | n-Bu | F$_3$C—CO$_2$H | — | 587.36 | — (A) |
| 60 | 1-(*-methyl)-4-(piperidin-1-yl)piperidine | H | 1,4-phenylene | H | H | H | H | n-Bu | F$_3$C—CO$_2$H | — | 591.41 | — (A) |

TABLE 1-continued (I bis)

| N° | R1 | R2 | A | R5 | R6 | R7 | R8 | R11 | salt | m.p. (° C.) | MS peak | LC (method) |
|---|---|---|---|---|---|---|---|---|---|---|---|---|
| 61 | *-CH2-NH-CH(Ph)-CH2-N(pyrrolidine) | H | 1,4-phenyl | H | H | H | H | n-Bu | F3C—CO2H | — | 613.40 | — (A) |
| 62 | *-CH2-(4-methylpiperidin-1-yl via N-piperidin-4-yl) | H | 1,4-phenyl | H | H | H | H | n-Bu | F3C—CO2H | — | 605.43 | — (A) |
| 63 | *-CH2-NH-CH2CH2-(piperidin-1-yl) | H | 1,4-phenyl | H | H | H | H | n-Bu | F3C—CO2H | — | 552.58 (M + 1) | — (B) |
| 64 | *-CH2-(4-benzylpiperazin-1-yl) | H | 1,4-phenyl | H | H | H | H | n-Bu | F3C—CO2H | — | 599.38 | — (A) |
| 65 | *-NH-CH2CH2-(4-hydroxypiperidin-1-yl) | H | 1,3-phenyl | H | H | H | H | n-Bu | F3C—CO2H | — | 567.38 | — (A) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 66 | (piperazine-butyl) | H | para-phenylene | H | H | H | H | n-Bu | F$_3$C—CO$_2$H | — | 565.40 | (A) |
| 67 | (benzimidazole-ethylamino) | H | para-phenylene | H | H | H | H | n-Bu | F$_3$C—CO$_2$H | — | 585.45 (M+1) | (B) |
| 68 | (phenyl-piperazine) | H | para-phenylene | H | H | H | H | n-Bu | F$_3$C—CO$_2$H | — | 586.58 (M+1) | (B) |
| 69 | (morpholino-piperidine) | H | para-phenylene | H | H | H | H | n-Bu | F$_3$C—CO$_2$H | — | 594.55 (M+1) | (B) |

TABLE 1-continued
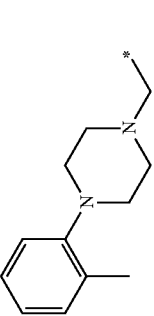
(I bis)
| N° | R1 | R2 | A | R5 | R6 | R7 | R8 | R11 | salt | m.p. (°C.) | MS peak | LC (method) |
|---|---|---|---|---|---|---|---|---|---|---|---|---|
| 70 | 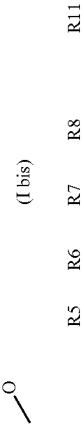 | H | 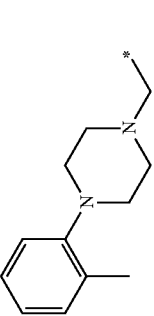 | H | H | H | H | n-Bu | F$_3$C—CO$_2$H | — | 600.52 (M + 1) | — (B) |
| 71 | 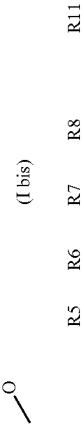 | H | 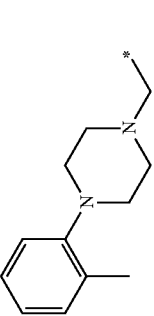 | H | H | H | H | n-Bu | F$_3$C—CO$_2$H | — | 637.42 | — (A) |
| 72 | 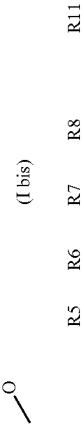 | H | 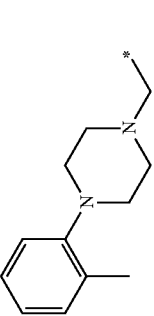 | H | H | H | H | n-Bu | F$_3$C—CO$_2$H | — | 554.51 (M + 1) | — (B) |
| 73 | 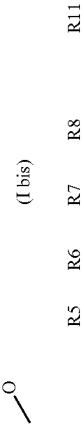 | H | 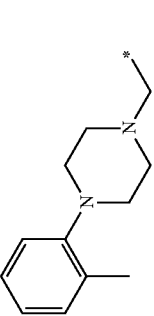 | H | H | H | H | n-Bu | F$_3$C—CO$_2$H | — | 551.38 | — (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 74 | 2,6-dimethylmorpholin-4-yl piperidin-4-yl-N-CH2-* | H | *-C6H4-* (para) | H | H | H | H | n-Bu | F3C—CO2H | — | 622.57 (M + 1) | — (B) |
| 75 | 4-(2-phenylethyl)piperazin-1-yl-CH2-* | H | *-C6H4-* (para) | H | H | H | H | n-Bu | F3C—CO2H | — | 613.40 | — (A) |
| 76 | 4-(1-phenylethyl)piperazin-1-yl-CH2-* | H | *-C6H4-* (para) | H | H | H | H | n-Bu | F3C—CO2H | — | 613.40 | — (A) |
| 77 | piperidin-1-yl-C(O)-* | H | *-C6H4-* (para) | H | H | H | H | H | 1 HCl | 92 | 467 (M + 1) | 6.37 (D) |

TABLE 1-continued (I bis) structure with R1, R2 on ring A; aryl with OCH2CH2CH2OCH3 substituent; R5, R6, R7, R8 on chain; C(O)NH-C(=NH)-NH-R11

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 78 | N-methylpiperazinyl-CH2-* | H | *-C6H4-* (para) | H | H | H | H | H | 1.4 HCl | 61.5 | 482 (M+1) | 5.3 (D) |
| 79 | 2-oxopiperidin-1-yl-CH2-* | H | *-C6H4-* (para) | H | H | H | H | H | 1 HCl | 61 | 467 (M+1) | 3.3 (D) |
| 80 | isopropyl-O-* | H | *-C6H4-* (para) | H | H | H | H | H | 1 HCl | 68 | 414 (M+1) | 7.3 (D) |
| 81 | 4-acetylpiperazin-1-yl-C(O)-* | H | *-C6H4-* (para) | H | H | H | H | H | 1 HCl | 97.5 | 510 | 3.1 (D) |
| 82 | (H3C)2CH-O-* | H | *-C6H4-* (para) | H | H | H | H | n-Bu | 1 HCl | 120.4 | 470 | 5.1 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 83 | H₃C-S(O)₂-* | H | *-C₆H₄-* | H | H | H | H | H | 1 HCl | 148.2 | 434 | 6.1 (D) |
| 84 | (H₃C)₂CH-S(O)₂-* | H | *-C₆H₄-* | H | H | H | H | H | 1 HCl | 81.2 | 462 | 6.7 (D) |
| 85 | CH₃CH₂-S(O)₂-* | H | *-C₆H₄-* | H | H | H | H | H | 1 HCl | 60.8 | 448 | 6.01 (D) |
| 86 | morpholine-C(O)-* | H | *-C₆H₄-* | H | H | H | H | H | 1 HCl | 79.6 | 469 | 6.13 (D) |
| 87 | 4-tBu-piperidine-C(O)-* | H | *-C₆H₄-* | H | H | H | H | H | 1 HCl | 105.6 | 523 | 6.2 (D) |

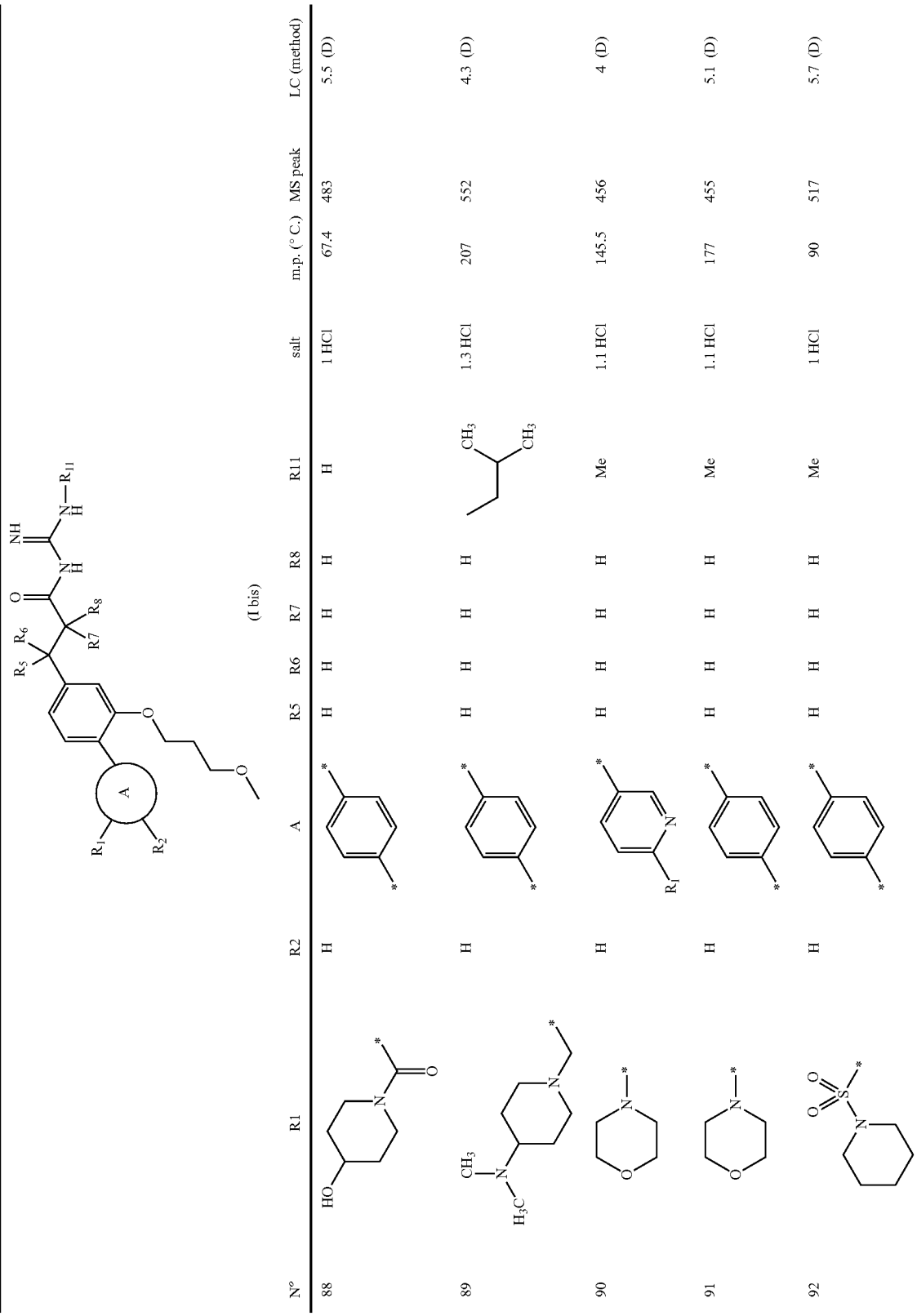

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 93 | EtO— | H | phenyl (R1 substituted) | H | H | H | H | H | F$_3$C—CO$_2$H | — | 399.22 | 1.46 (A) |
| 94 | H | H | pyrazole (R1 substituted) | H | H | H | H | H | F$_3$C—CO$_2$H | — | 345.18 | 1.11 (A) |
| 95 | CH$_3$O— | CH$_3$O— | pyrimidine (R1, R2 substituted) | H | H | H | H | H | F$_3$C—CO$_2$H | — | 417.20 | 1.14 (A) |
| 96 | (H$_3$C)$_2$N— | H | pyridine (R1 substituted) | H | H | H | H | H | F$_3$C—CO$_2$H | — | 399.23 | 0.99 (A) |
| 97 | CH$_3$O— | H | pyridine (R1 substituted) | H | H | H | H | H | F$_3$C—CO$_2$H | — | 386.20 | 1.43 |

TABLE 1-continued
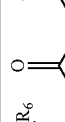
(I bis)
| N° | R1 | R2 | A | R5 | R6 | R7 | R8 | R11 | salt | m.p. (°C.) | MS peak | LC (method) |
|---|---|---|---|---|---|---|---|---|---|---|---|---|
| 98 |  | H | 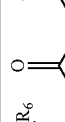 | H | H | H | H | H | F$_3$C—CO$_2$H | — | 502.23 | 1.5 (A) |
| 99 |  | H |  | H | H | H | H | H | HCl | 102.9 | — | 8.90 (D) |
| 100 | F | H |  | H | H | H | H | n-Bu | HCl | 115 | 430 (M + H) | 8.90 (D) |
| 101 |  | H |  | H | H | H | Me | H | 1 HCl | 207.7 | 510 | 3.80 (D) |
| 102 |  | H |  | H | H | H | H | H | 1 HCl | 169.4 | 505 | 3.60 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 103 | 4,4-dimethylpiperidin-1-ylcarbonyl | H | 1,4-phenylene (*,*) | H | H | H | H | H | 1 HCl | 174.4 | 495 | 8.00 (D) |
| 104 | F | Br | phenyl with R1 | H | H | H | H | H | $F_3C-CO_2H$ | — | 451.09 | 1.77 (D) |
| 105 | F | OEt | phenyl with R1, R2 | H | H | H | H | H | $F_3C-CO_2H$ | — | 417.21 | 1.67 (D) |
| 106 | piperidin-1-ylcarbonyl | H | phenyl with R1 | H | H | H | H | H | $F_3C-CO_2H$ | — | 466.26 | 1.49 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 107 | morpholinylmethyl-* | H | *-C6H4-R1 (meta) | H | H | H | H | H | F3C—CO2H | — | 454.26 | 1.03 (D) |
| 108 | H3C-S(O)2-* | H | *-C6H4-R1 (meta) | H | H | H | H | H | F3C—CO2H | — | 433.17 | 1.35 (D) |
| 109 | H | H | benzofurazanyl-* | H | H | H | H | H | F3C—CO2H | — | 397.17 | 1.59 (D) |
| 110 | benzyl-* | H | *-pyrazolyl-N-R1 | H | H | H | H | H | F3C—CO2H | — | 435.23 | 1.49 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 111 | F | CH₃ | * with R1, R2 ortho | H | H | H | H | H | F₃C—CO₂H | — | 387.20 | 1.67 (D) |
| 112 | Cl | CH₃ | * with R2, R1 | H | H | H | H | H | F₃C—CO₂H | — | 403.17 | 1.87 (D) |
| 113 | Cl | Cl | * with R1, R2 | H | H | H | H | H | F₃C—CO₂H | — | 423.11 | 1.88 (D) |
| 114 | F | CH₃ | * with R2, R1 | H | H | H | H | H | F₃C—CO₂H | — | 387.20 | 1.72 (D) |

TABLE 1-continued
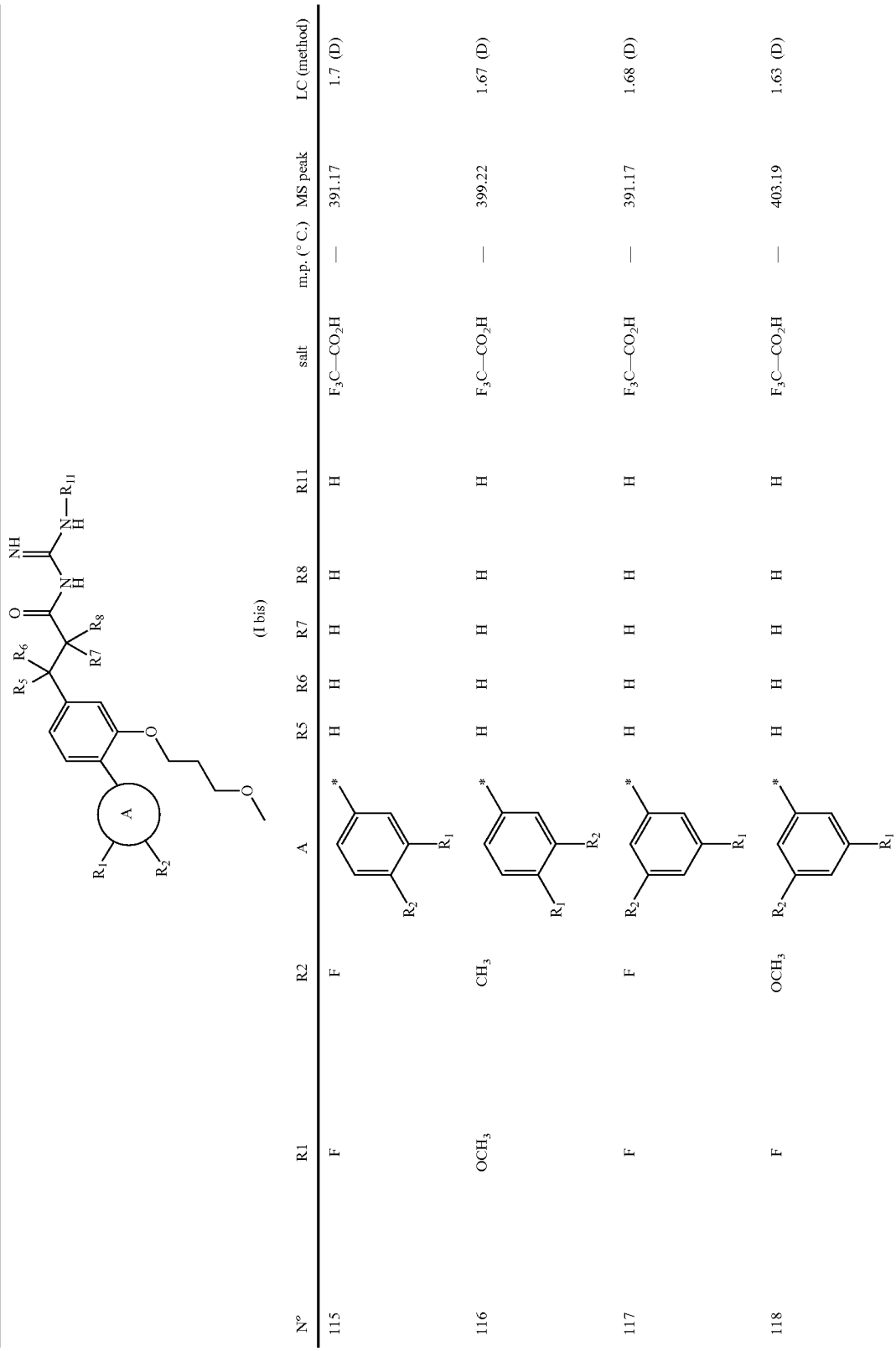
(I bis)
| N° | R1 | R2 | A | R5 | R6 | R7 | R8 | R11 | salt | m.p. (°C.) | MS peak | LC (method) |
|---|---|---|---|---|---|---|---|---|---|---|---|---|
| 115 | F | F | | H | H | H | H | H | F$_3$C—CO$_2$H | — | 391.17 | 1.7 (D) |
| 116 | OCH$_3$ | CH$_3$ | | H | H | H | H | H | F$_3$C—CO$_2$H | — | 399.22 | 1.67 (D) |
| 117 | F | F | | H | H | H | H | H | F$_3$C—CO$_2$H | — | 391.17 | 1.68 (D) |
| 118 | F | OCH$_3$ | | H | H | H | H | H | F$_3$C—CO$_2$H | — | 403.19 | 1.63 (D) |

TABLE 1-continued
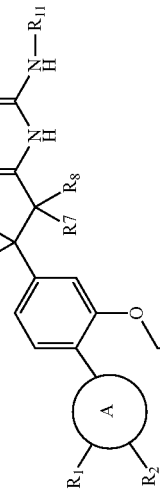
(I bis)
| N° | R1 | R2 | A | R5 | R6 | R7 | R8 | R11 | salt | m.p. (°C.) | MS peak | LC (method) |
|---|---|---|---|---|---|---|---|---|---|---|---|---|
| 119 | H₃C—N(CH₃)—C(=O)—* | H | *-C₆H₄-R₁ | H | H | H | H | H | F₃C—CO₂H | — | 426.23 | 1.27 (D) |
| 120 | CF₃ | H | *-C₆H₄-R₁ | H | H | H | H | H | F₃C—CO₂H | — | 423.18 | 1.78 (D) |
| 121 | iPr | H | *-C₆H₄-R₁ | H | H | H | H | H | F₃C—CO₂H | — | 397.24 | 1.87 (D) |
| 122 | CH₃O—CH₂CH₂—* | H | *-C₆H₄-R₁ | H | H | H | H | H | F₃C—CO₂H | — | 399.22 | 1.55 (D) |
| 123 | CH₃ | H | *-C₆H₄-R₁ | H | H | H | H | H | F₃C—CO₂H | — | 369.21 | 1.7 (D) |
| 124 | Cl | H | *-C₆H₄-R₁ | H | H | H | H | H | F₃C—CO₂H | — | 389.15 | 1.74 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 125 | F | OCH₃ | *-phenyl-R1,R2 | H | H | H | H | H | F₃C—CO₂H | — | 403.19 | 1.50 (D) |
| 126 | pyrazol-1-yl | H | *-phenyl-R1 | H | H | H | H | H | F₃C—CO₂H | — | 421.21 | 1.53 (D) |
| 127 | O-nPr | H | *-phenyl-R1 | H | H | H | H | H | F₃C—CO₂H | — | 413.23 | 1.74 (D) |
| 128 | O-nPr | H | *-phenyl-R1 | H | H | H | H | H | F₃C—CO₂H | — | 413.23 | 1.8 (D) |
| 129 | OEt | H | *-phenyl-R1 | H | H | H | H | H | F₃C—CO₂H | — | 399.22 | 1.67 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 130 | cyclopropylmethoxy (CH₂O-cyclopropyl) | H | phenyl with R1 (meta) | H | H | H | H | H | $F_3C-CO_2H$ | — | 425.23 | 1.8 (D) |
| 131 | OCH₃ | H | phenyl with R1 (meta) | H | H | H | H | H | $F_3C-CO_2H$ | — | 385.23 | 1.6 (D) |
| 132 | N(CH₃)C(O)* | H | phenyl (para) | H | H | H | H | H | $F_3C-CO_2H$ | — | 426.23 | 1.2 (A) |
| 133 | CF₃ | H | phenyl (para) | H | H | H | H | H | $F_3C-CO_2H$ | — | 423.18 | 1.59 (D) |
| 134 | iPr | H | phenyl (para) | H | H | H | H | H | $F_3C-CO_2H$ | — | 397.24 | 1.65 (A) |

TABLE 1-continued (I bis)

| N° | R1 | R2 | A | R5 | R6 | R7 | R8 | R11 | salt | m.p. (° C.) | MS peak | LC (method) |
|---|---|---|---|---|---|---|---|---|---|---|---|---|
| 135 | H₃C-CH(CH₃)-CH₂-* | H | *-C₆H₄-* | H | H | H | H | H | F₃C—CO₂H | — | 411.25 | 1.75 (A) |
| 136 | Et | H | *-C₆H₄-* | H | H | H | H | H | F₃C—CO₂H | — | 383.22 | 1.58 (A) |
| 137 | MeO-CH₂-* | H | *-C₆H₄-* | H | H | H | H | H | F₃C—CO₂H | — | 399.22 | 1.40 (A) |
| 138 | O-iPr | H | *-C₆H₄-* | H | H | H | H | H | F₃C—CO₂H | — | 413.23 | 1.54 (A) |
| 139 | OEt | H | *-C₆H₄-* | H | H | H | H | H | F₃C—CO₂H | — | 399.22 | 1.48 (A) |
| 140 | OCH₃ | H | *-C₆H₄-* | H | H | H | H | H | F₃C—CO₂H | — | 385.20 | 1.40 (A) |

TABLE 1-continued
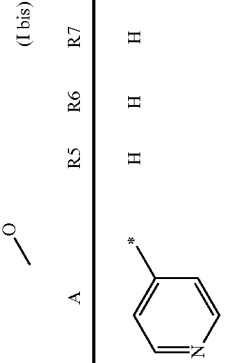
(I bis)
| N° | R1 | R2 | A | R5 | R6 | R7 | R8 | R11 | salt | m.p. (°C.) | MS peak | LC (method) |
|---|---|---|---|---|---|---|---|---|---|---|---|---|
| 141 | H | H | 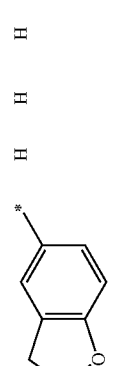 | H | H | H | H | H | F₃C—CO₂H | — | 356.18 | 0.97 (A) |
| 142 | H | H | 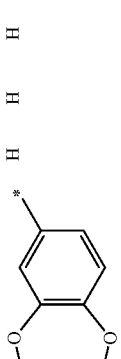 | H | H | H | H | H | F₃C—CO₂H | — | 397.20 | 1.39 (A) |
| 143 | H | H | 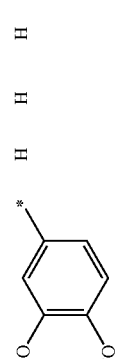 | H | H | H | H | H | F₃C—CO₂H | — | 427.21 | 1.41 (A) |
| 144 | H | H | 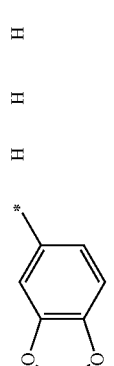 | H | H | H | H | H | F₃C—CO₂H | — | 413.20 | 1.36 (A) |
| 145 | H | H |  | H | H | H | H | H | F₃C—CO₂H | — | 399.18 | 1.38 (A) |

TABLE 1-continued
(I bis)
| N° | R1 | R2 | A | R5 | R6 | R7 | R8 | R11 | salt | m.p. (°C.) | MS peak | LC (method) |
|---|---|---|---|---|---|---|---|---|---|---|---|---|
| 146 | H | H |  | H | H | H | H | H | F$_3$C—CO$_2$H | — | 395.20 | 1.23 (A) |
| 147 | Cl | H |  | H | H | H | H | H | F$_3$C—CO$_2$H | — | 395.11 | 1.55 (A) |
| 148 | H | H |  | H | H | H | H | H | F$_3$C—CO$_2$H | — | 411.16 | 1.59 (A) |
| 149 | Cl | OCH$_3$ |  | H | H | H | H | H | F$_3$C—CO$_2$H | — | 419.16 | 1.51 (A) |
| 150 | F | CH$_3$ |  | H | H | H | H | H | F$_3$C—CO$_2$H | — | 387.20 | 1.49 (A) |

TABLE 1-continued
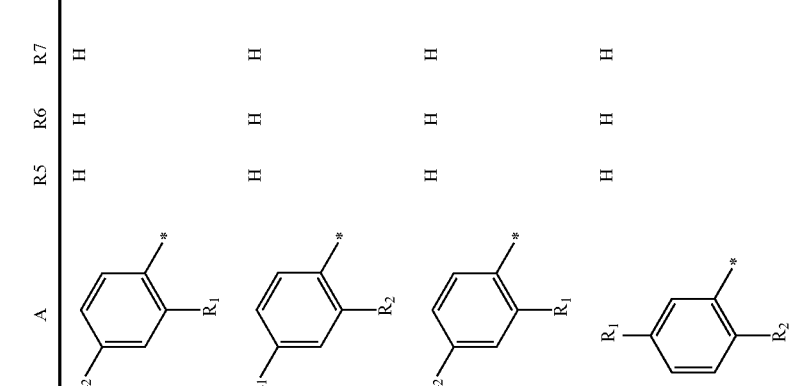
(I bis)
| N° | R1 | R2 | A | R5 | R6 | R7 | R8 | R11 | salt | m.p. (° C.) | MS peak | LC (method) |
|---|---|---|---|---|---|---|---|---|---|---|---|---|
| 151 | F | F | 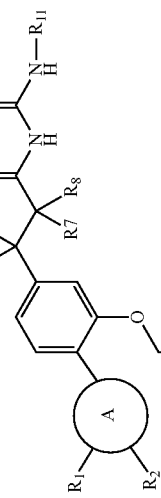 | H | H | H | H | H | F₃C—CO₂H | — | 391.17 | 1.46 (A) |
| 152 | F | O-iPr | | H | H | H | H | H | F₃C—CO₂H | — | 431.12 | 1.56 (A) |
| 153 | Cl | OCH₃ | | H | H | H | H | H | F₃C—CO₂H | — | 419.16 | 1.48 (A) |
| 154 | F | OiPr | | H | H | H | H | H | F₃C—CO₂H | — | 431.22 | 1.54 (A) |

TABLE 1-continued
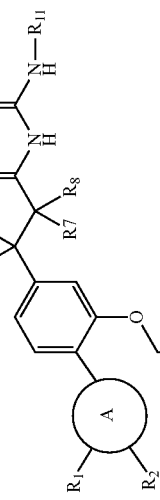
(I bis)
| N° | R1 | R2 | A | R5 | R6 | R7 | R8 | R11 | salt | m.p. (° C.) | MS peak | LC (method) |
|---|---|---|---|---|---|---|---|---|---|---|---|---|
| 155 | CH₃ | CH₃ | R₂–⌬–* / R₁ | H | H | H | H | H | F₃C—CO₂H | — | 383.22 | 1.55 (A) |
| 156 | F | CH₃ | R₂–⌬–* / R₁ | H | H | H | H | H | F₃C—CO₂H | — | 387.20 | 1.53 (A) |
| 157 | H | H | thiazole-* | H | H | H | H | H | F₃C—CO₂H | — | 363.20 (M + 1) | 0.98 (C) |
| 158 | F | H | *–⌬–* | H | H | H | H | nBu | 1 HCl | 115 | 430.30 (M + H) | 8.90 (D) |
| 159 | 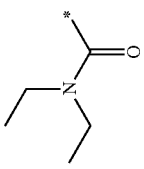 | H | *–⌬–* | H | H | H | H | H | 1.1 HCl | 67 | 455 (M + H) | 6.70 (D) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 160 | 1H-imidazol-1-ylmethyl | H | 1,4-phenylene | H | H | H | H | H | 1.1 HCl | 91.4 | 437 | 4.70 (D) |
| 161 | (3-methyl-2-oxoimidazolidin-1-yl)methyl | H | 1,4-phenylene | H | H | H | H | H | 1.1 HCl | 109.8 | 468 | 5.10 (D) |
| 162 | H | H | pyridazin-3,6-diyl | H | H | H | H | H | 2.1 HCl | 66.5 | 357 | 4.48 (D) |
| 163 | (2-oxopiperidin-1-yl) | H | 1,4-phenylene | H | H | H | H | H | HCl | 133-134 | 453 (M + H) | 5.27 (A) |
| 164 | (2-oxopyrrolidin-1-yl)methyl | H | 1,4-phenylene | H | H | H | H | H | HCl | 80 (decomp) | 453 (M + H) | 3.23 (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 165 | N,N'-dimethyl-2,5-dioxopiperazinyl-CH2- | H | 1,4-phenylene | H | H | H | H | H | HCl | 100 (decomp) | 496 (M + H) | 3.06 (A) |
| 166 | H | H | pyrimidine (R1 at 5) | H | H | H | H | H | F3C—CO2H | — | 357 (M + H) | 0.86 (D) |
| 167 | cyclopropylmethyl-SO2- | H | 1,4-phenylene | H | H | H | H | H | HCl | 49 | 474 (M + H) | 6.35 (A) |
| 168 | cyclopentyl-SO2- | H | 1,4-phenylene | H | H | H | H | H | HCl | 74 | 488 (M + H) | 6.93 (A) |
| 169 | tert-butyl-CH2-SO2- | H | 1,4-phenylene | H | H | H | H | CH3 | HCl | 35 | 504 (M + H) | 6.93 (A) |

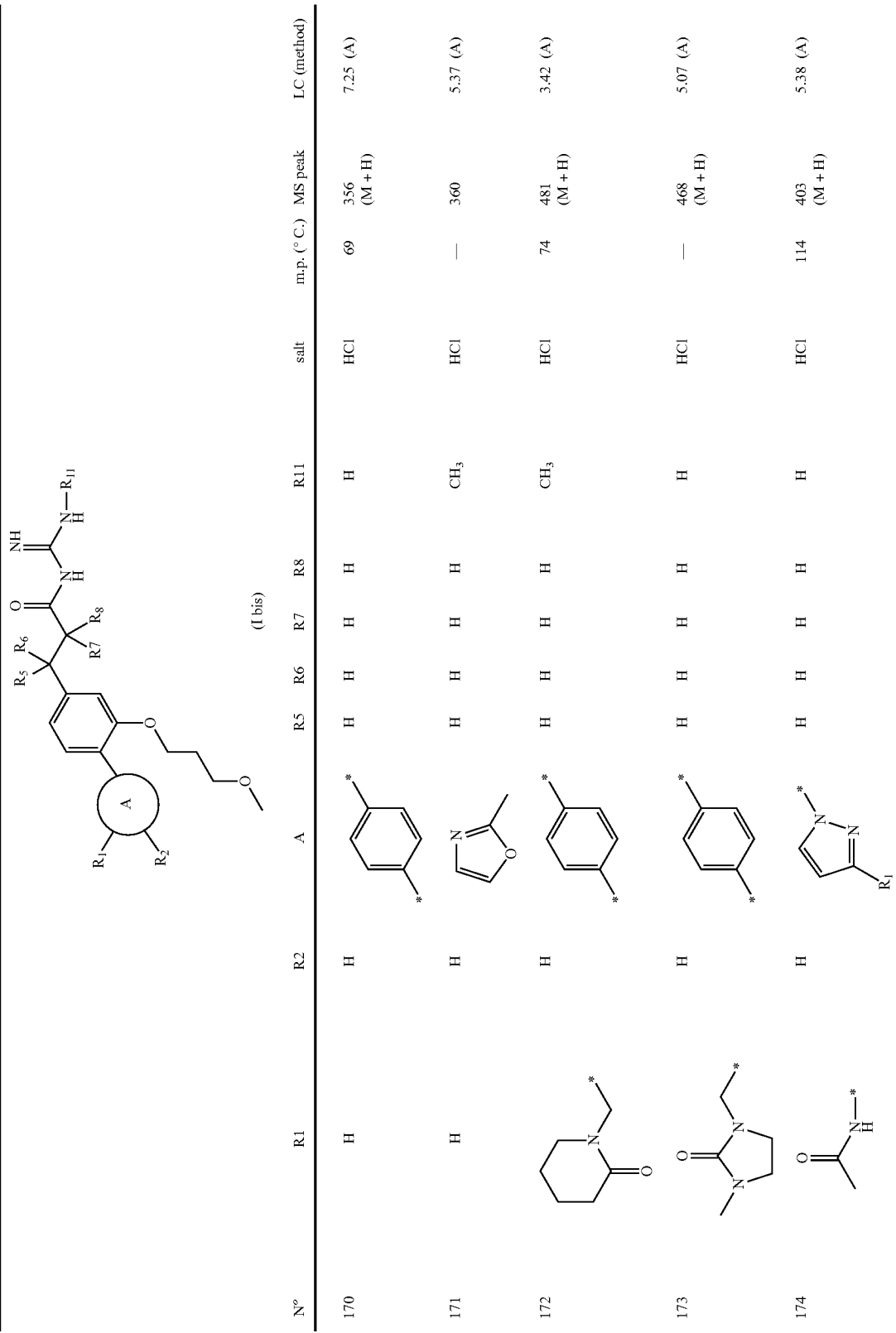

TABLE 1-continued (I bis)

| Nº | R1 | R2 | A | R5 | R6 | R7 | R8 | R11 | salt | m.p. (°C.) | MS peak | LC (method) |
|---|---|---|---|---|---|---|---|---|---|---|---|---|
| 175 | 1H-imidazol-1-ylmethyl | H | 1,4-phenylene | H | H | H | H | $CH_3$ | HCl | 209-210 | 451 (M + H) | 4.77 (A) |
| 176 | tert-butylsulfonylethyl | H | 1,4-phenylene | H | H | H | H | $CH_3$ | HCl | 40-41 | 518 (M) | 5.41 (A) |
| 177 | 1H-1,2,4-triazol-1-ylmethyl | H | 1,4-phenylene | H | H | H | H | $CH_3$ | HCl | 68 | 450 (M + H) | 6.85 (A) |
| 178 | 1H-imidazol-1-ylmethyl | H | 1,3-phenylene | H | H | H | H | H | HCl | 170 | 437 (M + H) | 5.87 (A) |
| 179 | (2-oxopiperidin-1-yl)methyl | H | 1,3-phenylene | H | H | H | H | H | HCl | — | 467 (M + H) | 6.45 (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 180 | H | H | 3,5-dimethylisoxazol-4-yl | H | H | H | H | CH₃ | HCl | — | 389 (M + H) | 5.93 (A) |
| 181 | (piperidin-2-one-1-yl)methyl | H | 1,4-phenylene | H | H | H | H | CH₃ | HCl | 50 | 495 (M + H) | 3.99 (A) |
| 182 | (piperidin-2-one-1-yl)methyl | H | 1,3-phenylene | H | H | H | H | CH₃ | HCl | 68-69 | 481 (M + H) | 6.47 (A) |
| 183 | tert-butylsulfonylmethyl | H | 1,3-phenylene | H | H | H | H | H | HCl | 54 | 490 (M + H) | 6.95 (A) |
| 184 | 1,3-dihydroxypropan-2-yl | H | 1,3-phenylene | H | H | H | H | CH₃ | HCl | — | 444 (M + H) | 5.37 (A) |

TABLE 1-continued

| N° | R1 | R2 | A | R5 | R6 | R7 | R8 | R11 | salt | m.p. (° C.) | MS peak | LC (method) |
|---|---|---|---|---|---|---|---|---|---|---|---|---|
| 185 | tert-butylsulfonyl | H | tetrahydroisoquinoline | H | H | H | H | CH₃ | HCl | 175 | 545 (M + H) | 7.87 (A) |
| 186 | cyclopentylcarboxamide | H | phenyl (meta) | H | H | H | H | CH₃ | HCl | 52 | 481 (M + H) | 3.86 (A) |
| 187 | tert-butylcarboxamide | H | phenyl (para) | H | H | H | H | CH₃ | HCl | 139 | 483 (M + H) | 5.30 (A) |
| 188 | 2-oxopiperidinyl | H | phenyl (meta) | H | H | H | H | CH₃ | HCl | 83 | 467 (M + H) | 6.47 (A) |
| 189 | piperidinylcarbonyl | H | phenyl (meta) | H | H | H | H | CH₃ | HCl | — | 495 (M + H) | 7.32 (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 190 | 1,3-dimethyl-2-oxoimidazolidinyl-CH2* | H | *-C6H4-* (meta) | H | H | H | H | *-CH2CH2CF3 | HCl | 73 | 564 (M + H) | 3.58 (A) |
| 191 | 3,4-dimethylpyrazol-1-yl-CH2* | H | *-C6H4-* (meta) | H | H | H | H | H | HCl | 81 | 464 (M + H) | 3.51 (A) |
| 192 | morpholin-4-yl-SO2-CH2* | H | *-C6H4-* (meta) | H | H | H | H | CH3 | HCl | 80 | 533 (M + H) | 3.37 (A) |
| 193 | piperidin-1-yl-SO2-CH2* | H | *-C6H4-* (meta) | H | H | H | H | CH3 | HCl | 69 | 517 (M + H) | 3.48 (A) |
| 194 | tBu-SO2-CH2* | Cl | *-C6H3(R1)(R2)- | H | H | H | H | CH3 | HCl | 44-45 | 538 (M + H) | 7.72 (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 195 | morpholine-N-C(O)-N(CH3)-* | H | 1,3-phenylene | H | H | H | H | CH3 | HCl | 54-55 | 512 (M + H) | 7,02 (A) |
| 196 | 1-methyl-3-(methylene*)-imidazolidin-2-one | H | 1,3-phenylene | H | H | H | H | CH2CH2OH | HCl | 99 | 512 (M + H) | 7,33 (A) |
| 197 | 1-methyl-3-(methylene*)-imidazolidin-2-one | H | thiazole | H | H | H | H | CH3 | HCl | 184-185 | 489 (M + H) | 3,62 (A) |
| 198 | 3-isopropyl-1-(ethylene*)-pyrazole | H | 1,3-phenylene | H | H | H | H | CH3 | HCl | 142-143 | 492 (M + H) | 3,75 (A) |

TABLE 1-continued (I bis)

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 199 | tert-butylmethylsulfonyl | H | 2-thiazolyl (R1 at 4) | H | H | H | H | CH₃ | HCl | 64 | 511 (M + H) | 6.39 (A) |
| 200 | 1-acetyl-4-(methylsulfonyl)piperidinyl | H | 1,4-phenylene | H | H | H | H | CH₃ | HCl | 96-97 | 559 (M + H) | 5.90 (A) |
| 201 | CH₃ | — | benzimidazolyl | H | H | H | H | CH₃ | 2HCl | 200 | 424 (M + H) | 4.57 (A) |
| 202 | CH₃ | — | benzothiazolyl | H | H | H | H | CH₃ | HCl | 126 | 441 (M + H) | 6.93 (A) |
| 203 | neopentyl | — | benzimidazolyl | H | H | H | H | CH₃ | 2HCl | 116-117 | 480 (M + H) | 3.38 (A) |

TABLE 1-continued

| N° | R1 | R2 | A | R5 | R6 | R7 | R8 | R11 | salt | m.p. (°C.) | MS peak | LC (method) |
|---|---|---|---|---|---|---|---|---|---|---|---|---|
| 204 | tBu-SO2-CH2-* | H | *-C6H4-* (meta) | H | H | CH3 | CH3 | CH3 | HCl | 79 | 532 (M+H) | 7.42 (A) |
| 205 | morpholino-SO2-CH2-* | H | *-C6H4-* (meta) | H | H | H | H | —(CH2)—CF3 | HCl | 185 | 739 (M+H) | 5.43 (A) |
| 206 | morpholino-SO2-CH2-* | H | *-C6H4-* (meta) | H | H | H | H | iPr | HCl | 206 | 561 (M+H) | 5.29 (A) |

TABLE 2

[Structure (1 ter): R1-A-C6H3(OR3)-CH2CH2-C(O)-NH-C(=NH)-NH-R11]

| N° | R1 | A | R11 | R3—Q | salt | m.p. (° C.) | MS peak | LC (method) |
|---|---|---|---|---|---|---|---|---|
| 207 | morpholine-N-C(O)—* | *-m-C6H4-* | CH3 | F3C-CH2-CH2-O—* | HCl | 93 | 506 (M) | 6.62 (A) |
| 208 | (CH3)3C-CH2-C(O)-NH—* | *-m-C6H4-* | CH3 | F3C-CH2-CH2-O—* | HCl | 116 | 506 (M) | 8.36 (A) |
| 209 | morpholine-N-C(O)-N(CH3)—* | *-m-C6H4-* | CH3 | CH3O-CH2-CF2-CH2-O—* | HCl | | | |
| 210 | morpholine-N-C(O)-N(CH3)—* | *-m-C6H4-* | CH3 | CH3O—(CH2)4—* | HCl | | | |

TABLE 3

[Structure of compound (1 quater): Central benzene ring with substituent groups R1-A on one position, an OCH2CH2CH2OCH3 (methoxypropoxy) chain on adjacent position, and a CR5R6-CH2-C(=O)-NH-C(=N-R9)-N(R10)(R11) guanidine-containing chain]

(1 quater)

| N° | R1 | A | R5 | R6 | N(R9)=C-N(R10)(R11) group | salt | m.p. (° C.) | MS | LC (Method) |
|---|---|---|---|---|---|---|---|---|---|
| 211 | (CH3)2N-piperidinyl-CH2-* | *-phenyl-* | H | H | 5,5-dimethyl-4-oxo-tetrahydropyrimidin-2-yl | 1 HCl | 132 | 578 (M + 1) | 6.43 (D) |

The renin-inhibiting activity of the compounds of the present invention was demonstrated experimentally using in vitro tests such as the reduction of angiotensin I formation from the natural substrate angiotensinogen or by the inhibition of the renin-catalyzed cleavage of a non-endogenous substrate, both being measured in a purified system or in presence of human plasma.

The protocol for the determination in a purified system of the in vitro IC50s of the compounds of the invention is described hereafter.

Recombinant human renin (expressed as prorenin in Chinese Hamster Ovary and purified after activation in active renin using standard methods) at 10 nM concentration is incubated with test compounds at various concentrations and the synthetic substrate Dabcyl-gaba-IHPFHLVIHT-EDANS (Bachem) at 10 µM for 2 h at room temperature, in 0.05 M Tris buffer pH 8 containing 0.1 M NaCl, 2.5 mM EDTA and 1.25 mg/ml bovine serum albumin. Increase in fluorescence (due to the Fluorescence Resonance Energy Transfer) is recorded at an excitation wave-length of 330 nm and at an emission wave length of 485 nm in a microplate spectrofluorometer. IC50 values are calculated from the percentage of inhibition of renin activity as a function of test compound concentration. The compounds of the invention show IC50 values lower than 10 µM, and comprised between 0.001 and 10 µM for most of the compounds. For example, compounds no 2, 6, 11, 13, 21, 22, 25, 30, 48, 78, 157, 173, 179, 193, 194 and 205 display IC50s of 19, 100, 23, 79, 98, 10, 228, 70, 143, 42, 126, 53, 19, 16, 48, 40 nM, respectively.

The renin-inhibiting activity of the compounds of the present invention was also measured indirectly using an in vitro test such as a radioimmunoassay for the quantitative determination of angiotensin I in the presence of plasma. In the first step, the generation of angiotensin I in plasma samples is allowed by incubation at pH 5.5-6.0 at 37° C. for 1.5 hours in the presence, of enzymatic inhibitors. Next the radioimmunoassay is carried out, based on the competition between radio-labeled angiotensin I and the angiotensin I contained in the samples to be assayed. After the incubation, the amount of labeled angiotensin I bond to the antibody is inversely related to the amount of unlabelled angiotensin I present in the sample. Polyclonal antibodies anti-angiotensin I coated to tubes, $^{125}$I-angiotensin I ($\leq$4 µCi) in bovine albumin, buffer and sodium azide. Synthetic human angiotensin 1, buffer, calibrators and PMSF are all obtained from Cisbio-International, In vitro Diagnostics, France.

The assays are performed on plasma samples containing EDTA as anti-coagulant at 2-8° C. The samples are first centrifuged at 2000 g in a refrigerated centrifuge to recover the plasma fraction. The generation of angiotensin is carried out on 500 µl of sample, to which 10 µl of PMSF and 50 µl of buffer are added and vortexed. 200 µl of these blank samples are then incubated at 37° C. for 90 minutes then put in an ice bath. 50 µl of calibrators, controls, samples and blank samples are pipetted into labeled antibody-coated tubes. 500 µl of $^{125}$I-angiotensin are added to each tube. The tubes are vortexed then incubated at 20° C. for 90 minutes under orbital horizontal shaking. The liquid is next aspirated and the remaining radioactivity bound to the tubes was measured with a gamma scintillation counter.

Background counts are subtracted and calibration curves are generated by plotting the calibrator $B/B_0$ versus their corresponding angiotensin I concentration, using semi log coordinates. The sample values are read from the calibration curves. The value related to the corresponding blank samples are subtracted and the result is multiplied by a factor of 1.12 (initial sample dilution). The resulting concentration is divided by the angiotensin I production time (1.5 hours) and the plasma renin activity (PRA) is expressed as ng angiotensin I released per ml per hour as is calculated as follows:

PRA(ng/ml/h)=[{ng(Generated)−ng(Blank)}/1.5]× 1.12

$IC_{50}$ values are calculated from the percentage of inhibition of PRA as a function of test compound concentration. The compounds of the invention display $IC_{50}$ values between 0.001 and 10 µM.

The compounds according to the invention, displaying renin-inhibiting activity, can be useful for the preparation of medicaments, specifically of medicaments inhibiting renin. Therefore, another object of the invention is a medicament, which comprises a compound of formula (I) or an addition salt thereof with a pharmaceutically acceptable salt, or an hydrate or solvate of a compound of formula (I).

These medicaments are useful in therapeutics, in particular in the treatment and prevention of hypertension, heart failure, cardiac infarct, cardiac insufficiency, cardiac and vascular hypertrophy, left ventricular dysfunction after myocardial infarction, restenosis; glaucoma, various renal conditions such as renal fibrosis and failure, diabetic complications such as nephropathy and retinopathy, as well as end-organ damage such as kidney insufficiency. A further object of the present invention is therefore the use of a compound of formula (I) as defined above for the preparation of medicaments for the treatment or prevention of the above pathological states.

Another object of the invention is a pharmaceutical composition which comprises, as active principle, a compound of formula (I) according to the present invention. This pharmaceutical composition comprises an effective dose of at least one compound of formula (I) according to the invention, or an addition salt thereof with a pharmaceutically acceptable salt, or an hydrate or solvate thereof, and at least one pharmaceutically acceptable excipient. Said excipients are chosen according to the pharmaceutical form and the administration route desired, among usual excipients known to one of skill in the art.

In the pharmaceutical compositions according to the invention for the oral, sublingual, sub-cutaneous, intramuscular, intra-venous, topical, local, intratracheal, intranasal, transdermal or rectal administration, the active principle of formula (I) above or its salt, solvate or hydrate, can be administered as a unitary dosage form, in blend with usual pharmaceutical excipients, to animals and human beings for the prevention or for the treatment of pathological states mentioned above. The appropriate unitary dosage forms comprise the oral forms, such as tablets, hard or soft gelatin capsules, powders, granules and oral solutions or suspensions, the sublingual, buccal, intratracheal, intraocular, intranasal forms, the forms adapted to inhalation, topical, transdermal, sub-cutaneous, intramuscular or intra-venous delivery, the rectal forms and the implants. For the topical application, the compounds of the invention may be used as creams, gels, ointments or lotions.

As an example, a unitary dosage form for a compound according to the invention, in the form of a tablet, can comprise the following ingredients:

| | |
|---|---|
| Compound according to the invention | 50.0 mg |
| Mannitol | 223.75 mg |
| Croscarmellose sodique | 6.0 mg |
| Maize starch | 15.0 mg |
| Hydroxypropyl methylcellulose | 2.25 mg |
| Magnesium stearate | 3.0 mg |

In specific cases, higher or lower dosages may be appropriate; these dosages are comprised within the scope of the present invention. According to usual practice, the dosage suitable to each patient is determined by the physician according to the administration route, the weight and response of the patient.

The invention also relates to a pharmaceutical composition comprising a compound of formula (I) as defined above and one or more compounds active against restenosis, glaucoma, cardiac infarct, high blood pressure and end organ damage, e.g. cardiac insufficiency and kidney insufficiency. Examples for these additional compounds are angiotensin converting enzyme-inhibitors, angiotensin receptor antagonists, diuretics, endothelin receptor antagonists, endothelin converting enzyme inhibitors or neutral endopeptidase inhibitors, calcium channel blockers (antagonists), nitrates, isosorbiddinitrates, beta-receptor blockers, or alpha-1 adrenoreceptor antagonists.

The present invention, according to another of its aspects, also relates to a method for the treatment of the above pathological states, which comprises the administration to a patient of an effective dose of a compound according to the invention, or a salt with a pharmaceutically acceptable salt thereof, or an hydrate or a solvate thereof.

The invention claimed is:

1. A compound corresponding to the following formula (I):

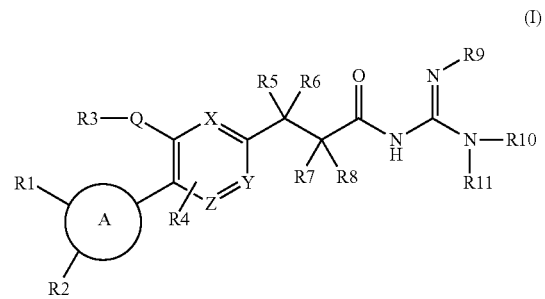

wherein:

A represents a phenyl group;

Q represents an oxygen atom or a —$CH_2$— link;

X, Y and Z represent carbon or nitrogen atoms, provided that:
  (i) X, Y, and Z each represent carbon atoms, whereby X, Y and Z form a phenyl ring; or
  (ii) one of X, Y and Z represents a nitrogen atom, whereby X, Y and Z form a pyridinyl ring; or
  (iii) X and Z represent nitrogen atoms, whereby X, Y and Z form a pyrazinyl ring; or
  (iv) Y and Z represent nitrogen atoms, whereby X, Y and Z form a pyridazinyl ring;

R1 and R2, identical or different, are chosen from among the list of atoms and groups consisting of: hydrogen, halogen, hydroxyl, cyano, oxo, —$CF_3$, (C1-C6)alkyl, Alk, (C1-C6)alkoxy, (C1-C6)alkyl-O—(C1-C6)alkyl, —O—(C1-C6)alkyl-O—(C1-C6)alkyl, (C3-C8)cycloalkyl, -O—(C3-C8)cycloalkyl, —$(CH_2)_m$—$SO_2$—(C1-C6)alkyl, benzyl, pyrazolyl, —$CH_2$-triazolyl optionally substituted by one to three (C1-C6)alkyl groups and -L-R12, wherein:
  m is equal to 0, 1 or 2;
  L represents a bond or a —$CH_2$- and/or —CO— and/or, —$SO_2$- linkage and R12 represents a (C3-C8)cycloalkyl or a group of formula (a), (b), (c'), (d) or (e):

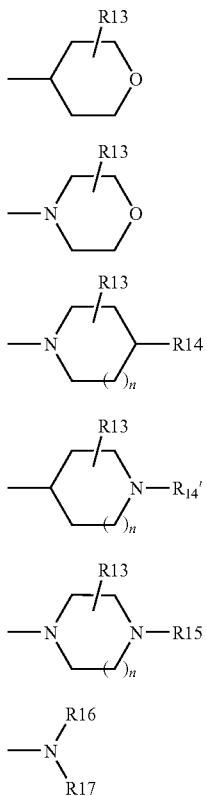

wherein:
n =0 or 1,
R13 represents one to three groups, identical or different, chosen from among the list of atoms and groups consisting of hydrogen, halogen, hydroxyl, (C1-C4)alkyl, oxo and phenyl,
R14 represents a hydrogen atom or is chosen from among the list of atoms and groups consisting of —NR18R19, —NR18—COOR19, —NR18-Alk-R20 and —R21 or R13 and R14 together form, with the same carbon atom to which they are attached, a (C3-C8)cycloalkyl group, which is therefore present in the spiro position on the ring of formula (c),
R14' represents a —CO—(C1-C6)alkyl group,
R15 is chosen from among the the list of groups consisting of —NR18R19, -Alk, —R20, -Alk-R20, -Alk- R21, —CO-Alk, —CO—R20, —CO—R21, -Alk-CO—NR18R19, (C3-C8)cycloalkyl and —CO—(C3-C8)cycloalkyl,
R16 represents a hydrogen atom or an Alk group,
R17 represents an -Alk, -Alk-R20, -Alk-R21, —CO—(C1-C6)alkyl, —CO—(C3-C8)cycloalkyl, or —CO-heterocycloalkyl,
R18 and R19, identical or different, represent a hydrogen atom or a (C1-C6)alkyl group,
R20 represents a phenyl or heteroaryl group, which is optionally substituted with one or more halogen atoms or (C1-C6)alkyl, hydroxyl or (C1-C4)alkoxy groups,
R21 represents a heterocycloalkyl group optionally substituted with one or more halogen atoms or (C1-C6)alkyl, hydroxyl or (C1-C4)alkoxy groups, and
Alk represents a (C1-C6)alkyl group which is linear or branched and which is optionally substituted with one to three groups, identical or different, chosen from among the list of atoms and groups consisting of halogen atoms, hydroxyl, phenyl, (C1-C4)alkoxy and —NR18R19,
R3 represents a linear (C1-C10)alkyl group which is optionally substituted by one to three groups, identical or different, chosen from among the list of atoms and groups consisting of halogen atoms and (C1-C4)alkoxy,
R4 represents a hydrogen or halogen atom or a hydroxyl, cyano, (C1-C6)alkyl or (C1-C6)alkoxy group,
R5 and R6 represent, independently one from the other, a hydrogen or halogen atom or a (C1-C5)alkyl group, or R5 and R6 together form, with the carbon atom to which they are attached, a (C3-C6)cycloalkyl group,
R7 and R8 represent, independently one from the other, a hydrogen atom or a (C1-C5)alkyl group, or R7 and R8 together form, with the carbon atom to which they are attached, a (C3-C6)cycloalkyl group,
R9 and R10 represent, independently one from the other, a hydrogen atom or a hydroxyl, —CO—(C1-C6)alkyl or —COO—(C1-C6)alkyl group, or R9 and R10 together form a linear (C2-C3)alkylene chain, thereby forming a 5 or 6-membered ring with the nitrogen atoms to which they are attached, said alkylene chain being optionally substituted by one to three groups chosen from among the list of atoms and groups consisting of: (C1-C4)alkyl, (C3-C6)cycloalkyl groups in the spiro position, oxo, hydroxyl and amino, and
R11 represents a hydrogen atom or a (C1-C8)alkyl or (C3-C6)cycloalkyl group, which is optionally substituted by one to three groups chosen from among list of atoms and groups consisting of: halogen atoms, hydroxyl, cyano, (C1-C6)alkoxy, —NR18R19, —COOR18, —CO—NR18R19 and pyridinyl;
in the form of a free base or of an addition salt with an acid or a base.

2. A compound of formula (I) as claimed in claim 1, wherein Q represents an oxygen atom;
in the form of a free base or of an addition salt with an acid or a base.

3. A compound of formula (I) as claimed in claim 1, wherein Q represents an —CH$_2$-link;
in the form of a free base or of an addition salt with an acid or a base.

4. A compound of formula (I) as claimed in claim 1, wherein X, Y and Z represent carbon atoms;
in the form of a free base or of an addition salt with an acid or a base.

5. A compound of formula (I) as claimed in claim 1, wherein:
R1 and R2, identical or different, are chosen from among the list of atoms and groups consisting of: hydrogen, halogen, hydroxyl, —CF$_3$, (C1-C6)alkyl, Alk, (C1-C6)alcoxy, (C1-C6)alkyl-O—(C1-C6)alkyl, (CH$_2$)$_m$—SO$_2$—(C1-C6)alkyl, benzyl, pyrazolyl or —CH$_2$-triazolyl group optionally substituted by one to three (C1-C6)alkyl groups and -L-R12;
R13 represents one to three groups, identical or different, chosen from among the list of atoms and groups consisting of hydrogen and halogen atoms and (C1-C4)alkyl, oxo and phenyl groups, and R15 is chosen from among the the list of groups consisting of -Alk, —R20, -Alk-R20, -Alk-R21, —CO-Alk, —CO—R20, —CO—R21, -Alk-CO—NR18R19, (C3-C8)cycloalkyl and —CO—(C3-C8)cycloalkyl in the form of a free base or of an addition salt with an acid or a base.

6. A compound of formula (I) as claimed in claim 1, wherein R3 represents a linear (C2-C8)alkyl group which is optionally substituted by one or two groups, identical or different, chosen from among the list of atoms and groups consisting of halogen atoms and the (C1-C4)alkoxy;

in the form of a free base or of an addition salt with an acid or a base.

7. A compound of formula (I) as claimed in claim 4, wherein R4 represents a hydrogen or halogen atom or a hydroxyl, cyano, (C1-C6)alkyl or (C1-C6)alkoxy group;

in the form of a free base or of an addition salt with an acid or a base.

8. A compound of formula (I) as claimed claim 1, wherein R5 and R6 represent, independently one from the other, a hydrogen or halogen atom or a (C1-C5)alkyl group;

in the form of a free base or of an addition salt with an acid or a base.

9. A compound of formula (I) as claimed in claim 4, wherein R7 and R8 represent, independently one from the other, a hydrogen atom or a (C1-C5)alkyl group or R7 and R8 together form, with the carbon to which they are attached, a (C3-C6)cycloalkyl group;

in the form of a free base or of an addition salt with an acid or a base.

10. A compound of formula (I) as claimed in claim 1, wherein R9 and R10 represent hydrogen atoms or, when R11=H, R9 and R10 together form a linear (C2-C3)alkylene chain being optionally substituted by one to three groups chosen from among the list of atoms and groups consisting of: (C1-C4)alkyl, (C3-C6)cycloalkyl groups in the spiro position, oxo, hydroxyl and amino groups;

in the form of a free base or of an addition salt with an acid or a base.

11. A compound of formula (I) as claimed in claim 1, wherein R1 represents a hydrogen or halogen atom or a —CF$_3$, (C1-C6)alkyl, (C1-C6) alkoxy or Alk group;

in the form of a free base or of an addition salt with an acid or a base.

12. A compound of formula (I) as claimed in claim 1, wherein R1 represents a group of formula -L-R12, wherein L represents a bond or a —CH$_2$—, —CO— or —SO$_2$— linkage and R12 represents a group of formula (b):

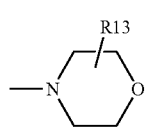
(b)

wherein R13 represents a hydrogen atom;

in the form of a free base or of an addition salt with an acid or a base.

13. A compound of formula (I) as claimed in claim 1, wherein R1 represents a group of formula -L-R12, wherein L represents a bond or a -CH$_2$—and/or —CO— and/or —SO$_2$— linkage and R12 represents a group of formula (c):

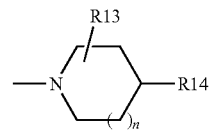
(c)

wherein:

R13 represents one to three groups, identical or different, chosen from among the list of atoms and groups consisting of hydrogen, hydroxyl, (C1-C4)alkyl, and oxo, R14 represents a hydrogen atom or is chosen from among the list of groups consisting of —NR18R19, —NR18—COOR19, —NR18-Alk-R20 and —R21, R20 represents a phenyl group, R21 represents a heterocycloalkyl group chosen from among the the list of groups consisting of morpholinyl, piperidinyl and pyrrolidinyl groups, which is optionally substituted with one or more (C1-C6)alkyl groups, and Alk represents a (C1-C6)alkyl group which is linear or branched;

in the form of a free base or of an addition salt with an acid or a base.

14. A compound of formula (I) as claimed in claim 1, wherein R1 represents a group of formula -L-R12, wherein L represents a bond or a —CH$_2$— or —CO—or —SO$_2$— or -SO$_2$—CH$_2$— linkage and R12 represents a group of formula (c):

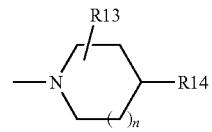
(c)

wherein:

R13 represents one to three groups, identical or different, chosen from among the list of atoms and groups consisting of hydrogen, hydroxyl, (C1-C4)alkyl, and oxo, R14 represents a hydrogen atom or is chosen from among the the list of groups consisting of —NR18R19, —NR18—COOR19, —NR18-Alk-R20 and —R21, R20 represents a phenyl group, R21 represents a heterocycloalkyl group chosen from among the the list of groups consisting of morpholinyl, piperidinyl and pyrrolidinyl groups, which is optionally substituted with one or more (C1-C6)alkyl groups, and Alk represents a (C1-C6)alkyl group which is linear or branched;

in the form of a free base or of an addition salt with an acid or a base.

15. A compound of formula (I) as claimed in claim 1, wherein R1 represents a group of formula -L-R12, wherein L represents a —CH$_2$— or —CO—linkage and R12 represents a group of formula (d):

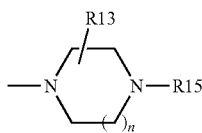
(d)

wherein:
R13 represents one to three groups, identical or different, chosen from among the list of atoms and groups consisting of hydrogen, (C1-C4)alkyl, oxo and phenyl,
R15 represents an hydrogen atom or is chosen from among the the list of groups consisting of -Alk, -Alk-R20, -Alk-R20—CO-Alk, -Alk-R21, —CO—R20, —CO—R21, -Alk—CO—NR18R19, (C3-C6)cycloalkyle, —CO—(C3-C6)cycloalkyl and (C1-C6)alkyl-O—(C1-C6)alkyl groups,
R20 represents a phenyl or heteroaryl group, which is optionally substituted with one or more (C1-C6)alkyl groups,
R21 represents a heterocycloalkyl group chosen from among the the list of groups consisting of morpholinyl and piperidinyl groups, and
Alk represents a (C1-C6)alkyl group which is linear or branched and which is optionally substituted with one to three hydroxyl groups;
in the form of a free base or of an addition salt with an acid or a base.

16. A compound of formula (I) as claimed in claim 1, wherein R1 represents a group of formula -L-R12, wherein L represents a bond or a —CH$_2$— or —CO— linkage and R12 represents a group of formula (e):

(e)

wherein:
R20 represents a heteroaryl group,
R21 represents a heterocycloalkyl group chosen from among the the list of groups consisting of piperidinyl and pyrrolidinyl, which is optionally substituted with one or more (C1-C6)alkyl or hydroxyl groups, and
Alk represents a (C1-C6)alkyl group which is linear or branched and which is optionally substituted with one to three groups, identical or different, chosen from among the the list of groups consisting of phenyl and —NR18R19, wherein R18 and R19, identical or different, represent (C1-C6)alkyl;
in the form of a free base or of an addition salt with an acid or a base.

17. A compound of formula (I) as claimed in claim 1, wherein R2 represents hydrogen, halogen atom, (C1-C6)alkoxy, or (C1-C6)alkyl;
in the form of a free base or of an addition salt with an acid or a base.

18. A compound of formula (I) as claimed in claim 1, wherein R3-Q- represents —CH$_3$—O—(CH$_2$)$_3$—O— or CF$_3$—(CH$_2$)$_2$—O— or CH$_3$O—CH$_2$—CF$_2$—CH$_2$—O— or CH$_3$O—(CH$_2$)$_4$;
in the form of a free base or of an addition salt with an acid or a base.

19. A compound of formula (I) as claimed in claim 1, wherein R4 represents a hydrogen atom;
in the form of a free base or of an addition salt with an acid or a base.

20. A compound of formula (I) as claimed in claim 1, wherein R7 and R8 represent hydrogen atoms or (C1-C4) alkyl groups;
in the form of a free base or of an addition salt with an acid or a base.

21. A compound of formula (I) as claimed in claim 1, wherein R7 and R8 together form, with the carbon atom to which they are attached, a (C3-C6)cycloalkyl group.

22. A compound of formula (I) as claimed in claim 1, wherein R9 and R10 represent hydrogen atoms or, when R11=H, R9 and R10 together form a linear (C2-C3)alkylene chain being optionally substituted by one to three groups chosen from among the list of atoms and groups consisting of (C1-C4)alkyl and oxo;
in the form of a free base or of an addition salt with an acid or a base.

23. A compound of formula (I) as claimed in claim 1, wherein R11 represents a hydrogen atom or a (C1-C5)alkyl or (C3-C6)cycloalkyl group, which is optionally substituted by one to three groups chosen from among the list of atoms and groups consisting of: halogen, hydroxyl, cyano, (C1-C6) alkoxy, —NR18R19 and (C3-C6)cycloalkyl, wherein R18 and R19, identical or different, represent a hydrogen atom or (C1-C6)alkyl;
in the form of a free base or of an addition salt with an acid or a base.

24. A process for the preparation of a compound of formula (I) according to claim 1, said process comprising the step of reacting a bicyclic ester of general formula:

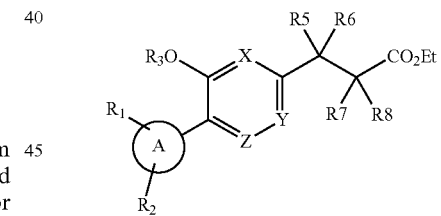

with a guanidine of formula (XXXVIII):

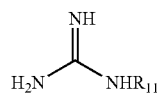
(XXXVIII)

in the presence of a base in a polar protic solvent;
wherein R1, R2, R3, R5, R6, R7, R8, R11, X, Y and Z are as defined in claim 1.

25. A process for the preparation of a compound of formula (I) according to claim 1, said process comprising the step of reacting a bicyclic ester of general formula (Xa):

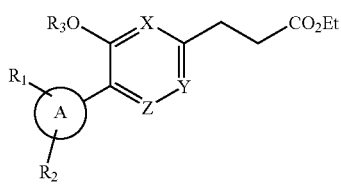

(Xa)

with a guanidine of formula (XXXVIII):

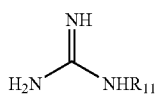

(XXXVIII)

in the presence of a base in a polar protic solvent;

wherein R1, R2, R3, R11, X, Y and Z are as defined in claim 1.

26. A process for the preparation of a compound of formula (I) according to claim 1, said process comprising the step of reacting a bicyclic carboxylic acid of general formula (XI'):

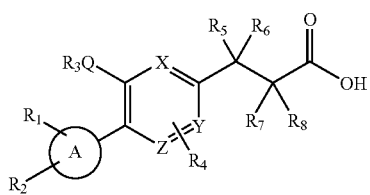

(XI')

with a guanidine of formula (XXXVIII'):

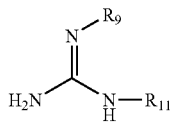

(XXXVIII')

in the presence of a carboxyl-activating coupling agent and a base;

wherein R1, R2, R3, R5, R6, R7, R8, R11, X, Y and Z are as defined in claim 1.

27. A process for the preparation of a compound of formula (I) according to claims 1, said process comprising the step of reacting a bicyclic carboxylic acid of general formula (XI):

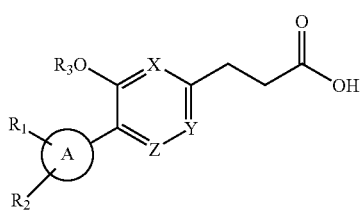

(XI)

with a guanidine of formula (XXXVIII):

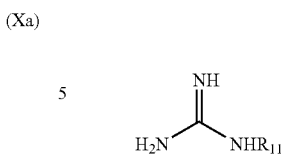

(XXXVIII)

in the presence of a carboxyl-activating coupling agent and a base;

wherein R1, R2, R3, R11, X, Y and Z are as defined in claim 1.

28. A process for the preparation of a compound of formula (I) according to claim 1, said process comprising the steps of:
(i) reacting a bicyclic carboxylic acid of general formula (XI'):

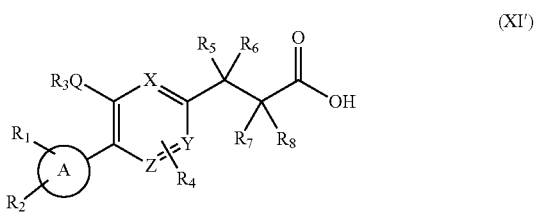

(XI')

with a compound of formula:

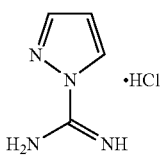

in the presence of a peptide coupling reagent and a base in DCM or THF at room temperature; and
(ii) treating the resulting intermediate with an amine R11—NH$_2$;

wherein R1, R2, R3, R5, R6, R7, R8, R11, X, Y and Z are as defined in claim 1.

29. A process for the preparation of a compound of formula (I) according to claim 1 wherein R9 and R10 together form a linear (C2-C3)alkylene chain, said process comprising the step of cyclizing a bicyclic compound of general formula (XXXIX):

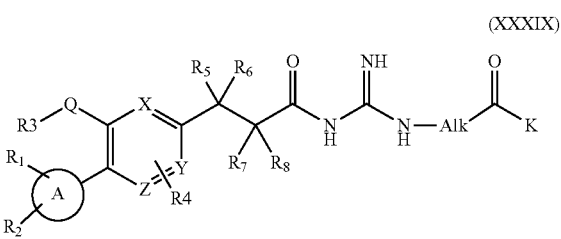

(XXXIX)

under basic conditions,
wherein:
R1, R2, R3, R4, R5, R6, R7 R8, A, X, Y and Z are as defined in claim 1;
Alk represents a substituted alkylene(C2-C3) chain; and
the group —CO—K represents an amide or an ester group.

30. A pharmaceutical composition comprising a compound of formula (I) according to any of claims 1 to 10, 11 to 17, or 18 to 23, or an addition salt of said compound to a pharmaceutically acceptable acid or base, or an hydrate or solvate of said compound, and at least one pharmaceutically acceptable excipient.

31. A compound according to claim 1, wherein R20 represents a pyridinyl, pyrazolyl, pyrimidinyl or benzimidazolyl group;

in the form of a free base or of an addition salt with an acid or a base, as well as in the form of an hydrate or of a solvate.

32. A compound according to claim 15, wherein R20 represents a pyridinyl, pyrazolyl, or pyrimidinyl group;

in the form of a free base or of an addition salt with an acid or a base, as well as in the form of an hydrate or of a solvate.

33. A compound according to claim 16, wherein R20 represents a benzimidazolyl group;

in the form of a free base or of an addition salt with an acid or a base, as well as in the form of an hydrate or of a solvate.

34. A process according to claim 28, wherein said peptide coupling reagent is DMAP and said base is TEA.

* * * * *